(12) United States Patent
Brown et al.

(10) Patent No.: US 10,549,248 B2
(45) Date of Patent: Feb. 4, 2020

(54) COMPOUNDING DEVICE SYSTEM, SOFTWARE AND METHOD FOR CONTROLLING THE PROCESS OF COMPOUNDING ADMIXTURES

(71) Applicant: B. Braun Medical Inc., Bethlehem, PA (US)

(72) Inventors: Michael Y. Brown, Bethlehem, PA (US); Jacob Albro Cowperthwaite, Bethlehem, PA (US); David Earl Hershey, II, Bethlehem, PA (US); Benjamin Richard Lane, Bethlehem, PA (US); Aaron S. Pearl, Bethlehem, PA (US); Mariano Mumpower, Bethlehem, PA (US); Jeffrey Manfred Gunnarsson, Bethlehem, PA (US); James Austin Kendall, Bethlehem, PA (US); Christopher Allen Gray, Bethlehem, PA (US); Stephanne Suzann Flint, Bethlehem, PA (US); Mark David Steenbarger, Bethlehem, PA (US); Alice Maria Weintraut, Bethlehem, PA (US)

(73) Assignee: B. BRAUN MEDICAL INC., Bethlehem, PA (US)

(*) Notice: Subject to any disclaimer, the term of this patent is extended or adjusted under 35 U.S.C. 154(b) by 183 days.

(21) Appl. No.: 15/668,122

(22) Filed: Aug. 3, 2017

(65) Prior Publication Data
US 2017/0354941 A1 Dec. 14, 2017

Related U.S. Application Data

(63) Continuation-in-part of application No. 15/490,372, filed on Apr. 18, 2017, which is a continuation of (Continued)

(51) Int. Cl.
*B01F 15/02* (2006.01)
*A61J 3/00* (2006.01)
(Continued)

(52) U.S. Cl.
CPC .......... *B01F 15/0243* (2013.01); *A61J 3/002* (2013.01); *B01F 3/0861* (2013.01); *B01F 5/008* (2013.01);
(Continued)

(58) Field of Classification Search
CPC ... A61J 3/002; A61M 39/223; B01F 13/1066; B01F 15/0243; B01F 15/0245; B65B 3/12
See application file for complete search history.

(56) References Cited

U.S. PATENT DOCUMENTS 4,696,671 A * 9/1987 Epstein ............. A61M 5/14224
128/DIG. 13
4,789,014 A * 12/1988 DiGianfilippo ......... A61J 3/002
141/1
(Continued)

FOREIGN PATENT DOCUMENTS

WO 2014152457 A2 9/2014

OTHER PUBLICATIONS

Brochure; "EXACTAMIX Compounding Systems for Specialty Pharmacies"; Baxter Healthcare Corporation; www.baxter.com; Oct. 2012.
(Continued)

*Primary Examiner* — Seth W. Mackay-Smith
(74) *Attorney, Agent, or Firm* — Kenealy Vaidya LLP

(57) ABSTRACT

An exemplary compounding method of controlling a compounding device to prepare an admixture of at least two distinct material sources can include examining material source solutions for incompatibility of the ingredients and operating a first and a second pump to prevent one of the
(Continued)

incompatible source solutions from entering a common flow path. The processing method can detect degradation of a fluid line by evaluating one or more of calibration error rate data, cumulative volumetric flow data, or cumulative pump operation data. The processing method can also selectively transfer a first group of source solutions using the first pump, receiving pump data from one or more sensors that sense actions of the pumps, applying fluid correction factors and calculating discrete pump movements, the pump movements being indicative of an amount of source solution displacement by a pump, and operating the pumps to selectively dispense the source solution amounts according to a preparation order.

24 Claims, 55 Drawing Sheets

Related U.S. Application Data application No. 14/797,000, filed on Jul. 10, 2015, now Pat. No. 9,623,389, application No. 15/668,122, which is a continuation-in-part of application No. 14/731,042, filed on Jun. 4, 2015, now Pat. No. 9,802,172, and a continuation-in-part of application No. 14/719,936, filed on May 22, 2015, now Pat. No. 10,143,985, and a continuation-in-part of application No. 14/700,779, filed on Apr. 30, 2015, now Pat. No. 9,802,171, and a continuation-in-part of application No. 14/693,867, filed on Apr. 23, 2015.

(51) Int. Cl.
| | |
|---|---|
| *B01F 13/00* | (2006.01) |
| *B65B 3/12* | (2006.01) |
| *F16K 11/22* | (2006.01) |
| *B01F 3/08* | (2006.01) |
| *B01F 5/00* | (2006.01) |
| *B01F 5/04* | (2006.01) |
| *F16K 5/04* | (2006.01) |
| *F16K 11/085* | (2006.01) |

(52) U.S. Cl.
CPC ............ *B01F 5/04* (2013.01); *B01F 5/0403* (2013.01); *B01F 13/0059* (2013.01); *B01F 15/026* (2013.01); *B65B 3/12* (2013.01); *F16K 5/04* (2013.01); *F16K 11/22* (2013.01); *A61J 2200/70* (2013.01); *F16K 11/0856* (2013.01)

(56) References Cited

U.S. PATENT DOCUMENTS

| | | | | |
|---|---|---|---|---|
| 4,925,444 | A * | 5/1990 | Orkin | A61M 5/16827 123/DIG. 13 |
| 5,040,699 | A * | 8/1991 | Gangemi | A61J 3/002 141/104 |
| 5,056,568 | A * | 10/1991 | DiGianfilippo | A61J 3/002 141/1 |
| 5,085,256 | A * | 2/1992 | Kircher | A61J 3/002 141/1 |
| 5,108,367 | A * | 4/1992 | Epstein | A61M 5/14224 128/DIG. 12 |
| 5,431,202 | A * | 7/1995 | Dikeman | A61J 3/002 137/606 |
| 5,609,572 | A * | 3/1997 | Lang | A61M 5/142 604/22 |
| 5,681,285 | A * | 10/1997 | Ford | A61M 5/172 604/151 |
| 5,927,349 | A * | 7/1999 | Martucci | G05D 11/131 141/83 |
| 6,975,924 | B2 * | 12/2005 | Kircher | B01F 13/1063 700/266 |
| 7,620,479 | B2 | 11/2009 | Kircher et al. | |
| 9,475,019 | B2 * | 10/2016 | Kaucky | A61J 3/002 |
| 10,058,694 | B2 * | 8/2018 | Norris | A61M 1/166 |
| 10,143,985 | B2 * | 12/2018 | Brown | F16K 5/04 |
| 2001/0017815 | A1 * | 8/2001 | Ackermann | B01F 3/088 366/152.2 |
| 2003/0010791 | A1 * | 1/2003 | Gentiluomo | A61J 3/002 221/92 |
| 2010/0057264 | A1 | 3/2010 | Kircher et al. | |
| 2013/0322201 | A1 * | 12/2013 | Hitchcock | B01F 15/00428 366/141 |
| 2015/0257974 | A1 * | 9/2015 | Demers | B01F 13/1066 206/438 |
| 2016/0045876 | A1 | 2/2016 | Kaucky et al. | |
| 2017/0035655 | A1 | 2/2017 | Kaucky et al. | |

OTHER PUBLICATIONS

Brochure; "Customize with Confidence EXACTAMIX Compounder"; Baxter Healthcare Corporation; www.baxter.com; Jun. 2013.

* cited by examiner

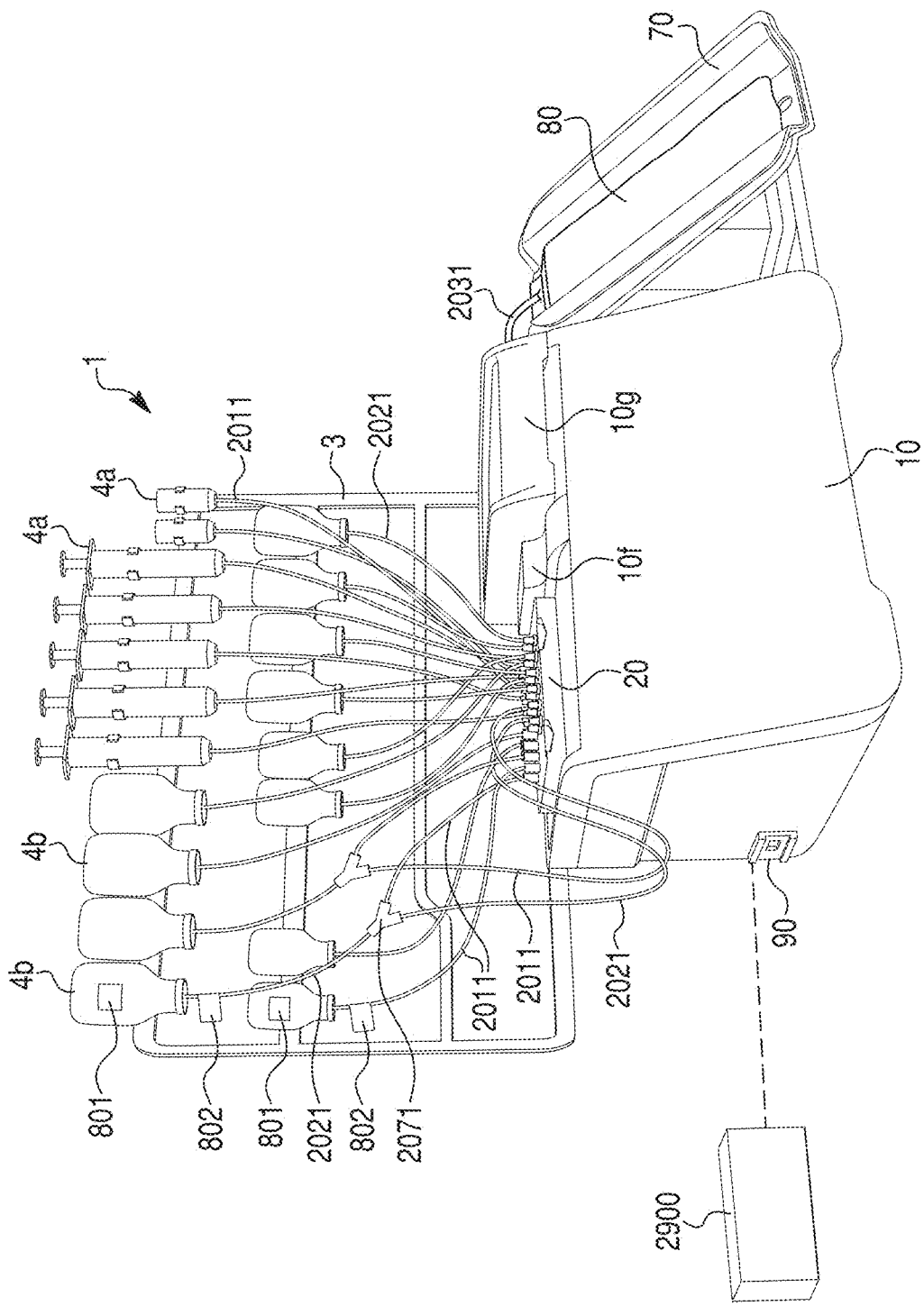

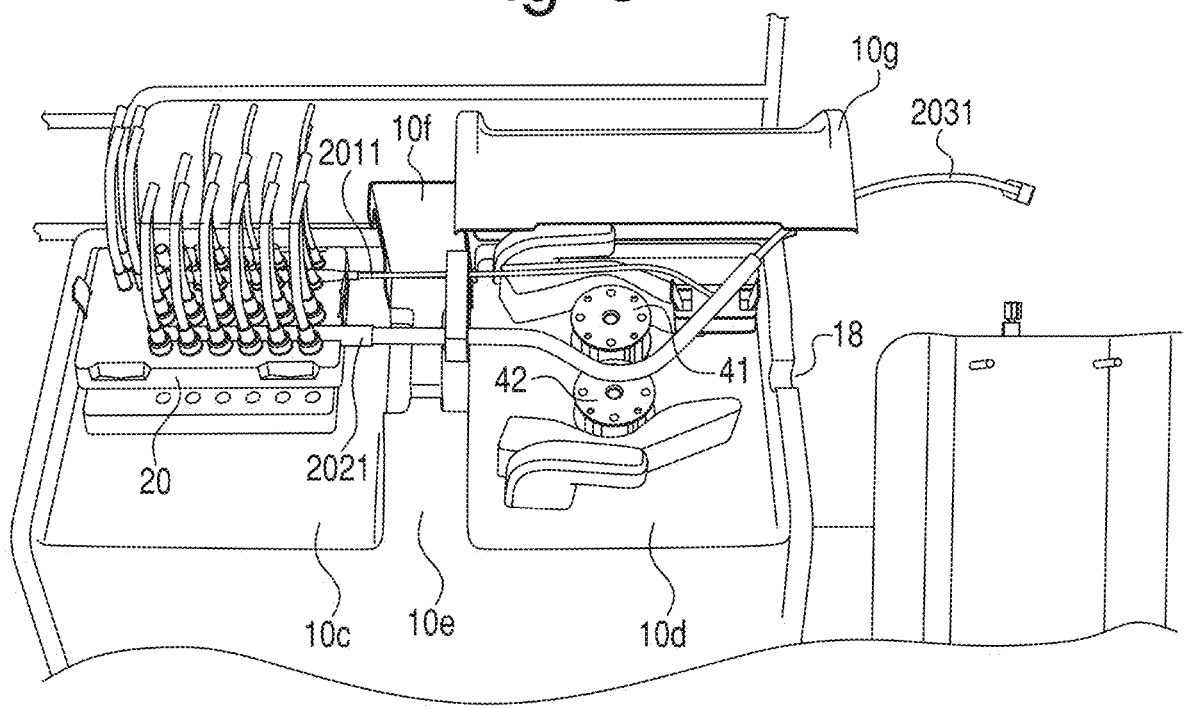
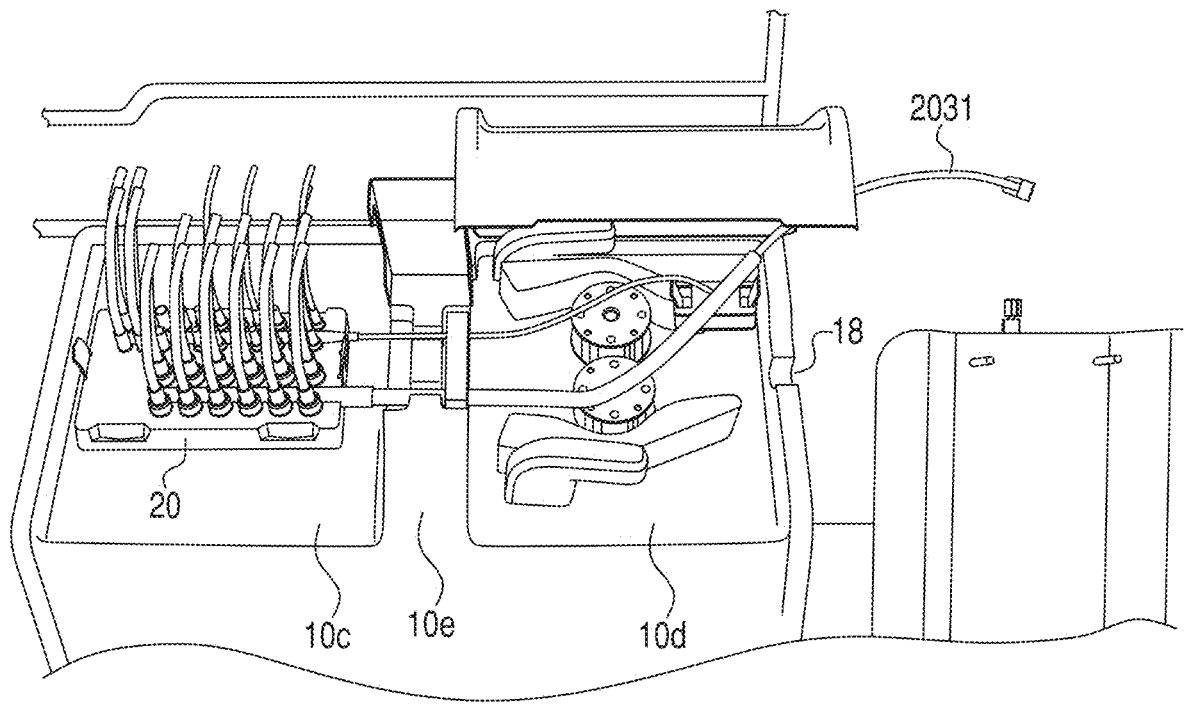

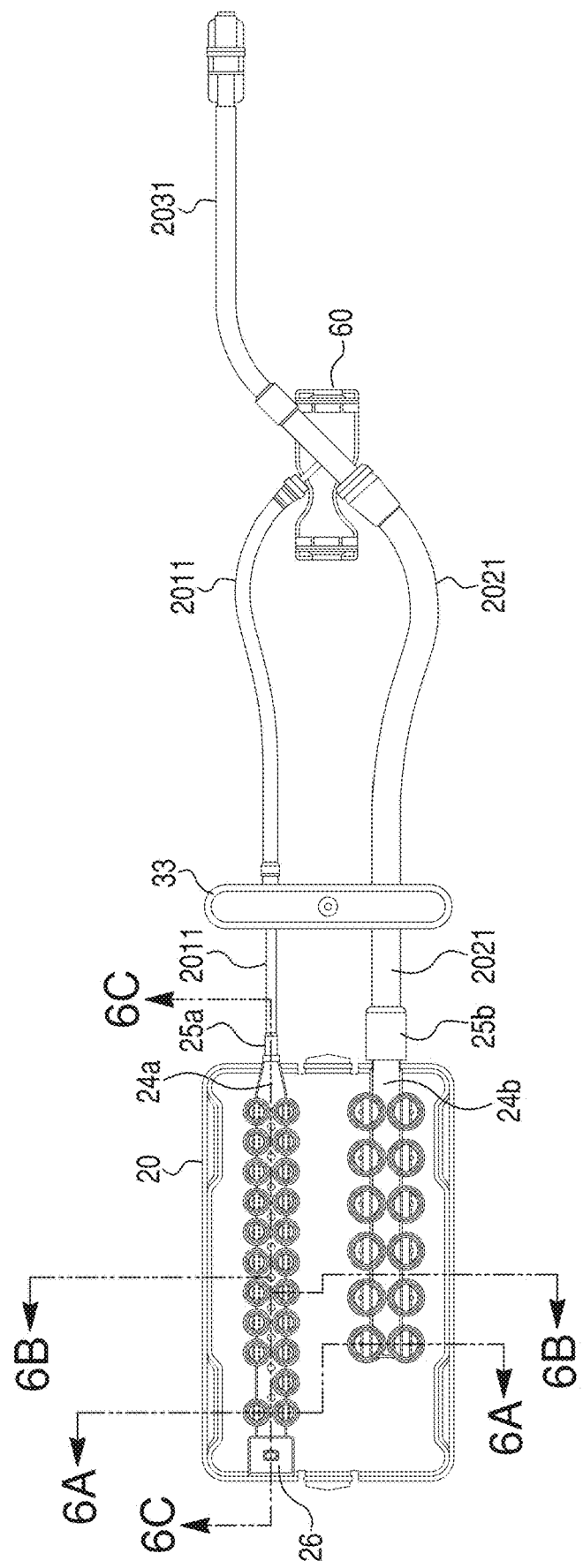

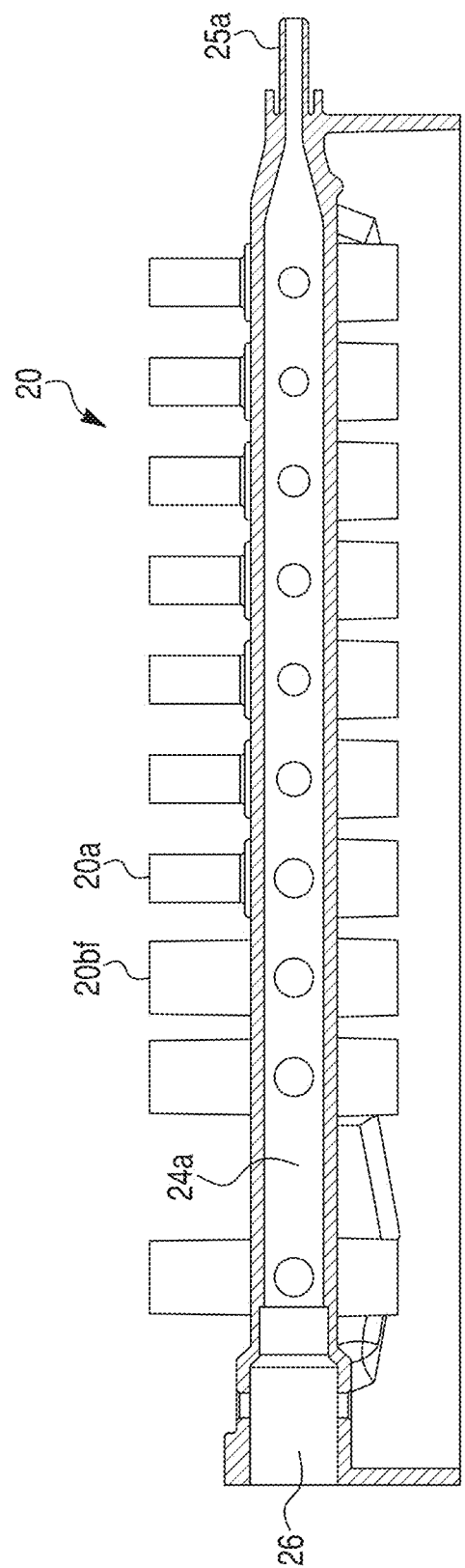

Transfer Set Installation
 Lot Number:
 Expiration Date:
1. Scan transfer set barcode.
Fig. 17

Load Cell Calibration

Note: Do not disturb load cell during calibration.

1. Ensure nothing is hanging on the load cell.

2. Add the 2000g calibration weight to the load cell for calibrating load cell.

3. Keep the 2000g calibration weight for verification of the load cell.

4. Remove the calibration weight and ensure nothing is hanging on the load cell.

Fig. 20

Load Cell Calibration

Note: Do not disturb load cell during calibration.

1. Ensure nothing is hanging on the load cell. 

2. Add the 2000g calibration weight to the load cell for calibrating load cell. 

3. Keep the 2000g calibration weight for verification of the load cell.
Result: Successful 

4. Remove the calibration weight and ensure nothing is hanging on the load cell.
Result: Successful 

✓ Calibration successful!

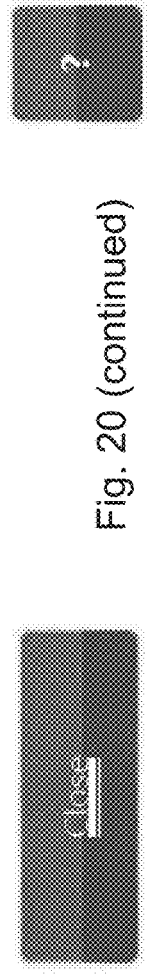

Fig. 20 (continued)

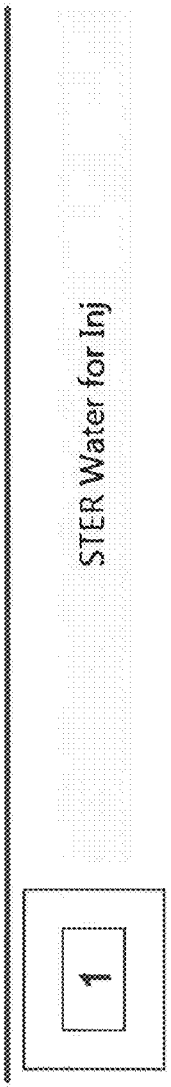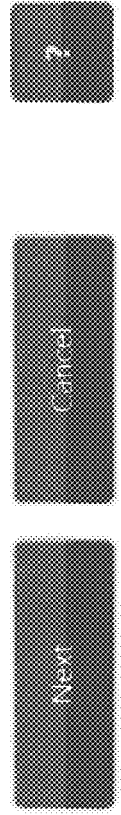
Fig. 23

Source Solution Information

Enter Solution Information

NDC:

Solution Name: STER Water for Inj

Lot Number:

Expiration Date:

Use Previous

Cancel

Fig. 23 (continued)

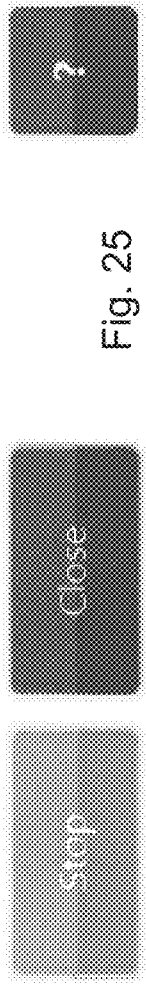
Fig. 25
Station 1 Prime - STER Water for Inj
1. Confirm the Calibration Container is attached and marked Not For Patient Use.
2. Review source container (optional). Reconfirm source container.
   NDC: 0264738550
   Lot Number: 1
   Expiration Date: 11/11/2017
   Spike: Universal - vent closed
3. Prime Source Container Lead.

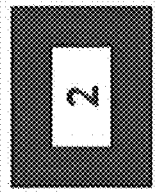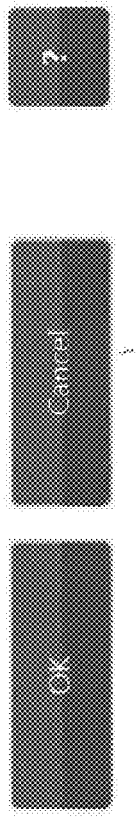
Fig. 33

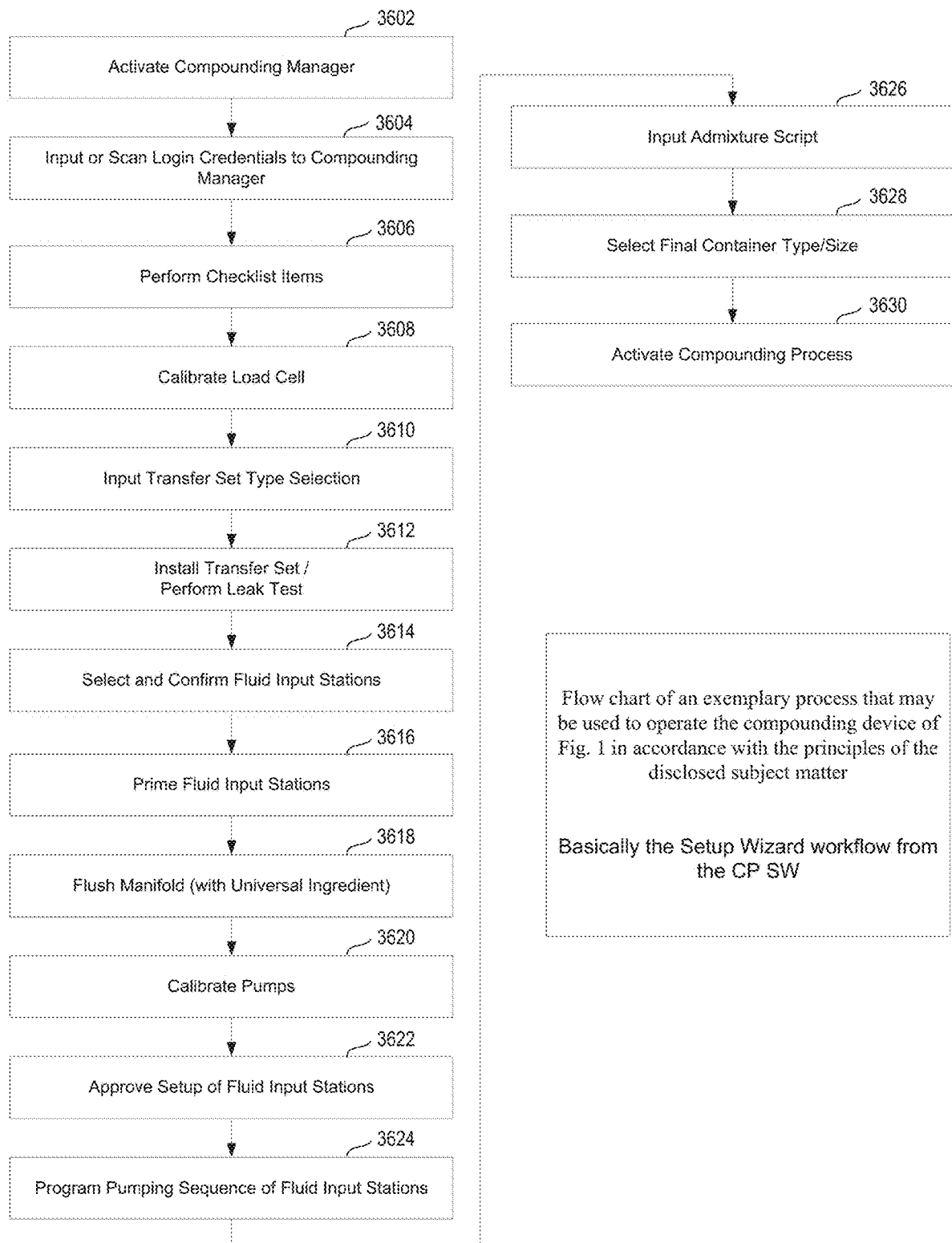

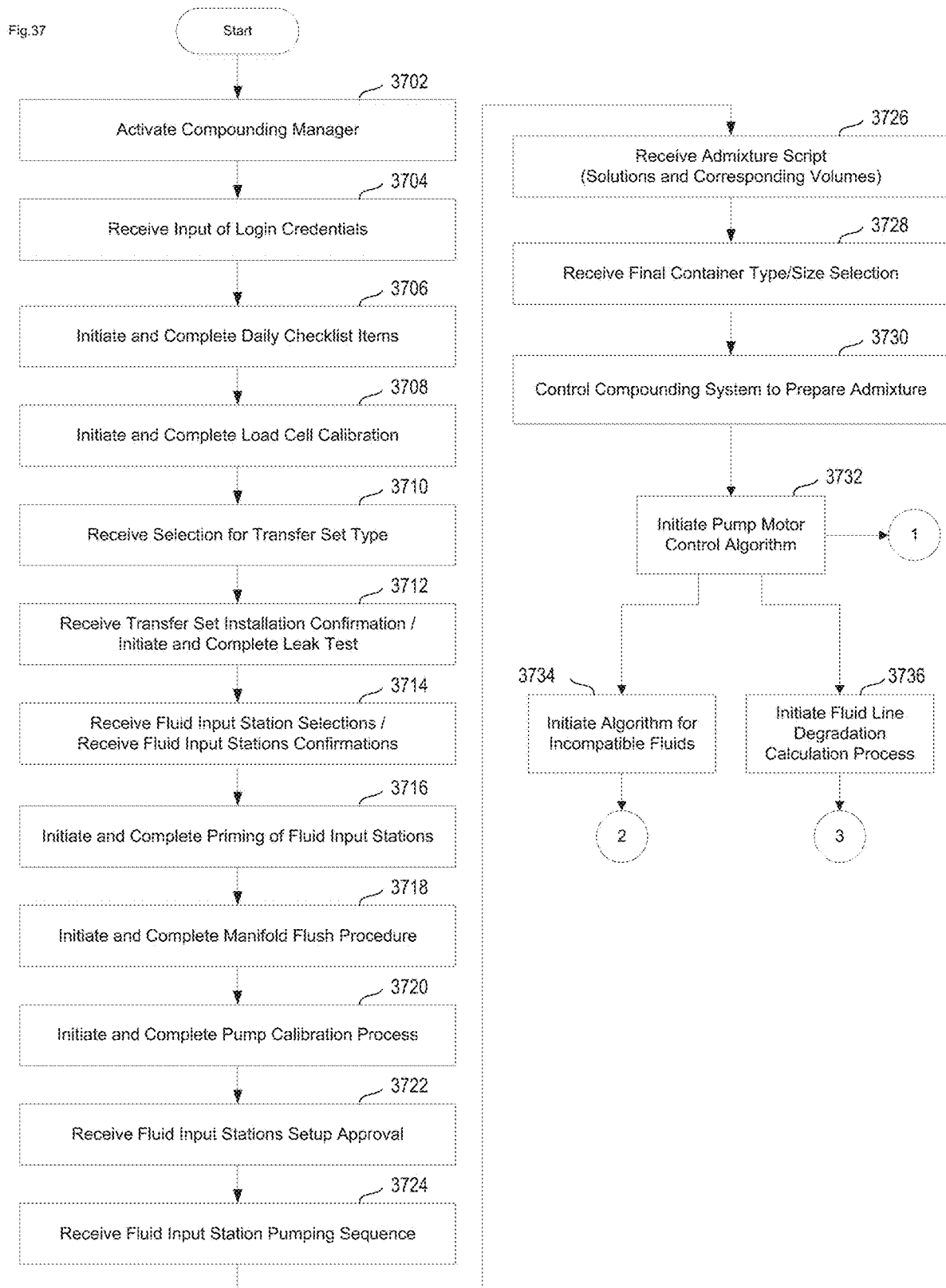

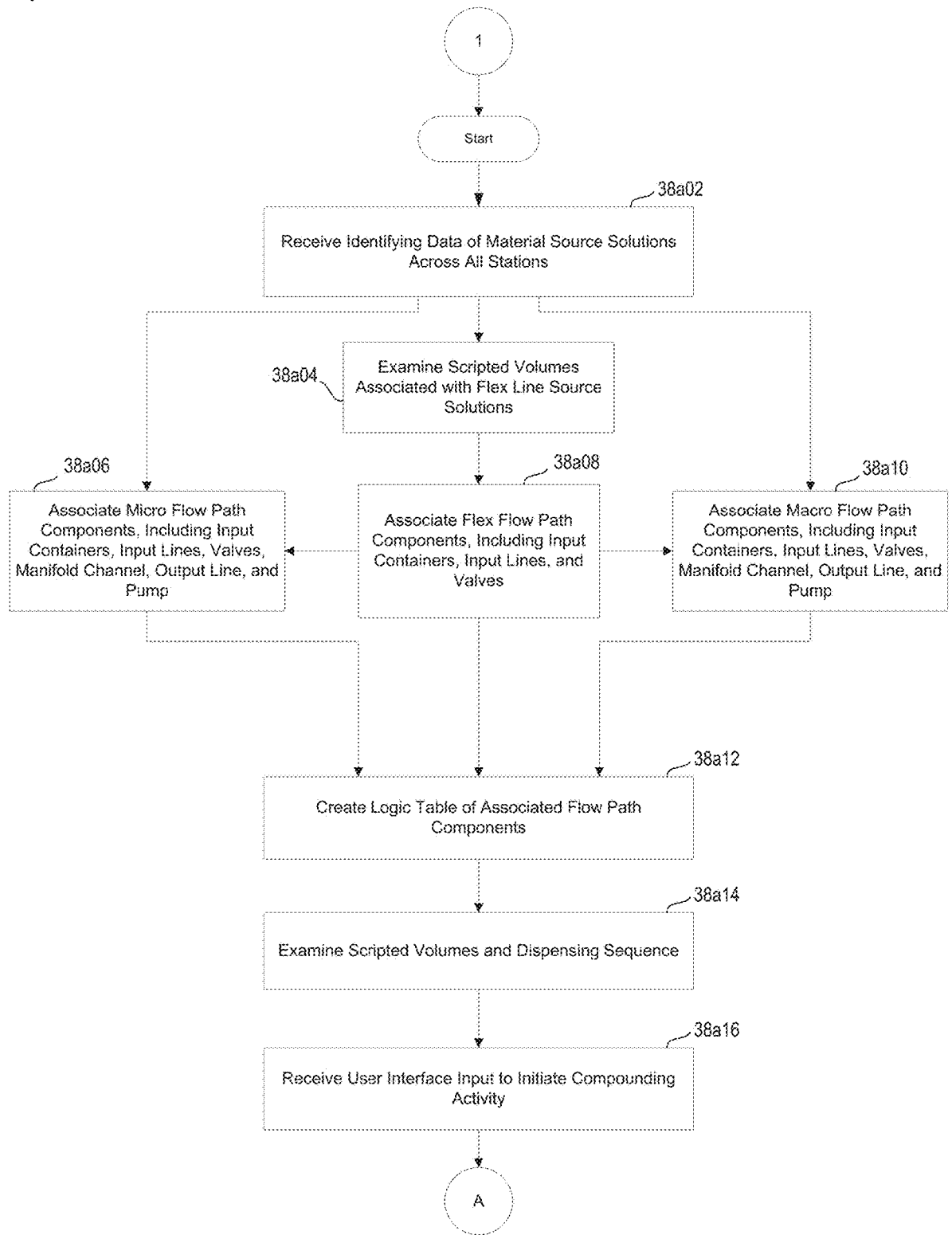

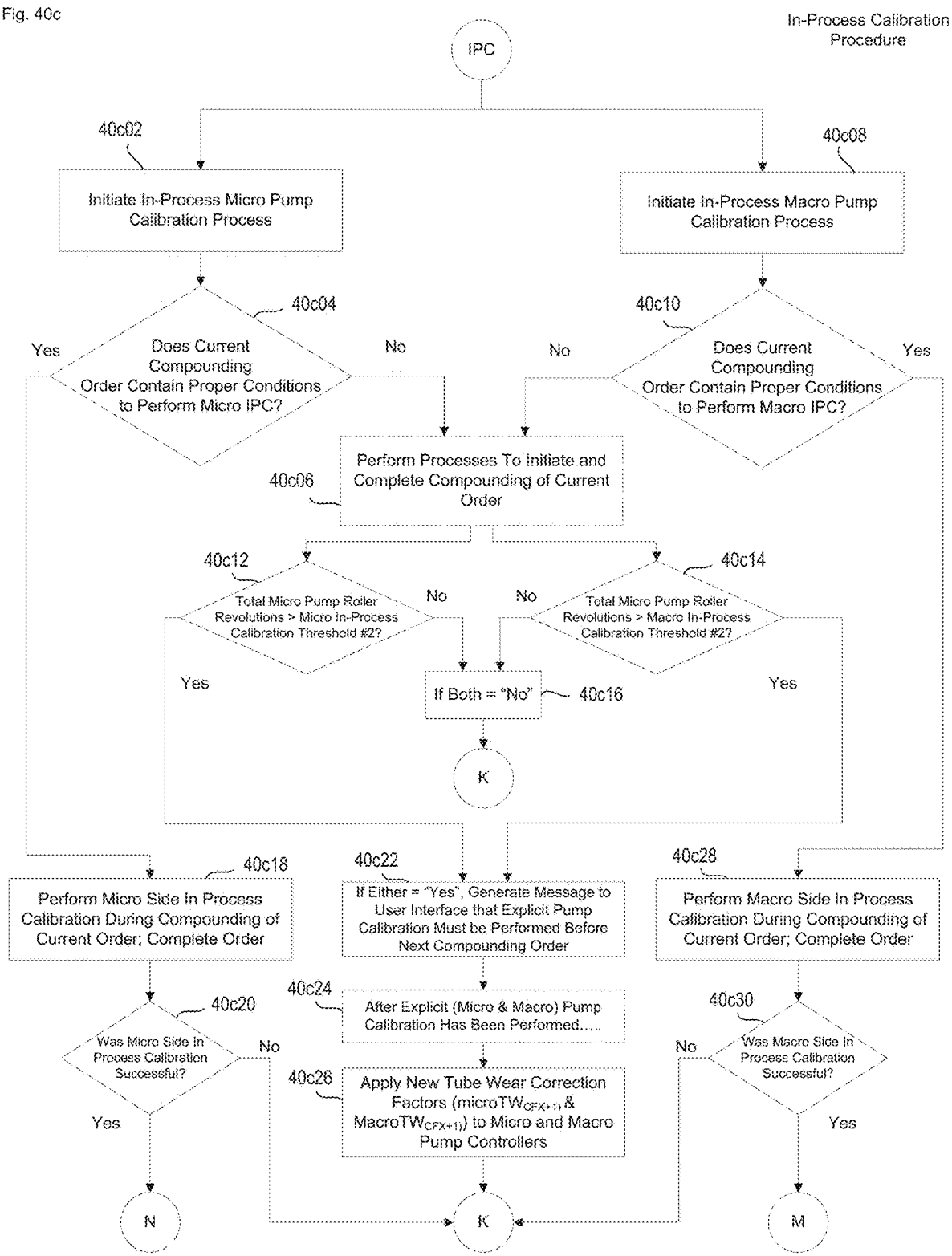

COMPOUNDING DEVICE SYSTEM, SOFTWARE AND METHOD FOR CONTROLLING THE PROCESS OF COMPOUNDING ADMIXTURES

This application is a continuation-in-part of and claims the priority benefit under 35 U.S.C. § 120 to U.S. patent application Ser. No. 14/693,867 filed on Apr. 23, 2015, U.S. patent application Ser. No. 14/700,779 filed Apr. 30, 2015, U.S. patent application Ser. No. 14/719,936 filed May 22, 2015, U.S. patent application Ser. No. 14/731,042 filed Jun. 4, 2015, and U.S. patent application Ser. No. 15/490,372 filed Apr. 18, 2017 which in turn claims priority to U.S. Pat. No. 9,623,389 filed on Jul. 10, 2015, the disclosures of which are hereby incorporated in their entirety by reference.

BACKGROUND

1. Field

The embodiments are directed to a compounding device system, software and method for controlling the process of compounding admixtures. More specifically, the presently disclosed subject matter relates generally to devices, systems, software, kits, and methods for controlling a process of compounding admixtures of various fluids, such as pharmaceuticals, assays, nutritional fluids, chemicals, and other fluids, for administration to human, animal, plant, mechanical/electrical/chemical/nuclear systems, or other users. In one exemplary embodiment, the disclosed subject matter can relate to devices, systems, software, kits and methods in which a controller controls a process wherein a plurality of parenteral ingredients are mixed or compounded together for delivery to a patient or user via an infusion or intravenous bag (e.g., for intravenous, intra-arterial, subcutaneous, epidural, or other transmission).

2. Description of the Related Art

Compounding involves the preparation of customized fluid ingredients including medications, nutritional liquids, and/or pharmaceuticals, on a patient-by-patient basis. Compounded medications and solutions can be made on an as needed basis whereby individual components are mixed together to form a unique solution having the strength and dosage needed by the patient. This method allows the compounding pharmacist to work with the patient and/or the prescriber to customize a medication to meet the patient's specific needs. Alternatively, compounding can involve the use of a compounding device to produce compounds in an anticipatory fashion, such as when a future or imminent demand for a particular combination of medicaments or pharmaceuticals or other compound components is known. Further, compounding devices can be used to produce pooled bags, for example, that include certain fluids that are needed for either a number of patients or for the same patient for a number of days or a number of administrations. Thus, the pooled bag(s) can be used by including further specific compounding components, if any, either for a specific patient or for a specific timing for the same patient.

Compounding devices typically use three types of measuring methods: gravimetric (e.g., additive gravimetric (weight final container) or subtractive gravimetric (weight the source containers as the pump delivers)), volumetric, or a combination of gravimetric and volumetric where each type can be used to check the other type. Compounders can be further broken down into three categories based on the minimum volumes they can deliver and the number of components they can accommodate: macro, micro, or macro/micro. Compounders typically have a stated minimum measurable volume and accuracy range. When compounding, higher volumes usually have larger absolute deviations, but lower percentage deviations. Operating software has been used to maximize the effectiveness and efficiency of compounding devices.

Gravimetric devices generally use a peristaltic pump mechanism combined with a weight scale or load cell to measure volume delivered. The volume delivered is calculated by dividing the weight delivered by the specific gravity of the ingredient. Gravimetric devices are not typically affected by running the source containers empty and delivering air into the final bag. These devices can be calibrated by using a reference weight for each ingredient. For example, the device's load cell can be calibrated using a reference mass on the load cell, and individual amounts of fluid dispensed measured by the load cell can be corrected based on the specific gravity of the fluid being dispensed.

Volumetric devices generally use both a peristaltic pump mechanism and a "stepper" motor to turn the pump mechanism in precisely measurable increments. The device calculates the volume delivered by the precision of the delivery mechanism, internal diameter of the pump tubing, viscosity of the solution, and the diameter and length of the distal and proximal tubing. Delivery from these devices can be affected by many factors including: variances in the pump tubing's material, length, elasticity, and diameter; temperature, which affects solution viscosity and tubing size; total volume pumped; ingredient head height; final bag height; position (e.g., initial and final positions) of the pump rollers relative to the pump platens; and empty source components. Thickness of the pump tubing can significantly affect delivery accuracy, and wear on the pumps over time can also cause diminishing accuracy.

Monitoring and replacing source containers before they are empty can prevent the volumetric devices from delivering air in lieu of the ingredient to the final container.

In some cases, due to injury, disease, or trauma, a patient may need to receive all or some of his or her nutritional requirements intravenously. In this situation, the patient will typically receive a basic solution containing a mixture of amino acids, dextrose, and fat emulsions, which can provide a major portion of the patient's nutritional needs. These mixtures are commonly referred to as parenteral mixtures ("PN"). Parenteral mixtures that do not include lipids are commonly referred to as total parenteral nutritional mixtures ("TPN"), while parenteral mixtures containing lipids are referred to as total nutritional admixtures ("TNA"). Often, to maintain a patient for an extended period of time on a PN, smaller volumes of additional additives, such as vitamins, minerals, electrolytes, etc., are also prescribed for inclusion in the mix.

Compounding devices facilitate the preparation of PN mixtures in accordance with the instructions provided by a medical professional, such as a doctor, nurse, pharmacist, veterinarian, nutritionist, engineer, or other. Compounding devices typically provide an interface that allows the medical professional to input, view, and verify the dosage and composition of the PN to be prepared and afterward confirm what had been compounded. The compounding device also typically includes source containers (i.e., bottles, bags, syringes, vials, etc.) that contain various solutions that can be part of the prescribed PN. The source containers can be hung from a framework that is part of the compounding device or can be mounted to a hood bar that is either part of or separate from the compounding device. A single pump or a plurality of pumps may be provided which, under the control of a controller, pump the selected solutions into a final container, for example, a receiving bag. The receiving bag is typically set on a load cell while being filled so that it can be weighed to ensure that the correct amount of solution is prepared. Once the bag has been filled, it can be released from the compounding device and, in this exemplary embodiment, can be used as a reservoir for intravenous infusion to a patient. Compounding devices are typically designed for operation in aseptic conditions when compounding pharmaceutical or neutraceutical ingredients.

When pharmaceuticals are used, a pharmacist can review instructions that are sent to the compounding device to ensure an improper mixture does not occur. The pharmacist can also ensure the specific sequencing of fluids/liquids is appropriate.

In the medical field, compounding devices can be used to compound fluids and/or drugs in support of chemotherapy, cardioplegia, therapies involving the administration of antibiotics and/or blood products therapies, and in biotechnology processing, including diagnostic solution preparation and solution preparation for cellular and molecular process development. Furthermore, compounding devices can be used to compound fluids outside the medical field.

Recently, there have been efforts to provide a compounding device that can operate more efficiently, with less downtime during source container replacement, and with increased usability features promoting more intuitive use of the system, as well as bubble and/or occlusion sensor mechanisms that cause fewer nuisance alarms.

SUMMARY

Accordingly, it may be beneficial to provide a compounding device, system, method, kit or software that operates more efficiently, improves set up time, and reduces downtime when an ingredient runs out and needs replacement, and which provides an aesthetically pleasing and intuitively operational structure, method of set up and use, and an associated usable, efficient and aesthetically pleasing computer interface. Certain embodiments of the disclosed subject matter also increase accuracy at small dispensed volumes, provide a form factor that promotes easier cleaning/disinfecting to maintain aseptic conditions, and also prevent errors, especially in transfer set/fluid path connections.

The disclosed embodiments also provide methods and apparatuses for controlling pumps, including control of the pump motors that are used to govern the starting, stopping and rates at which the pumps operate. The disclosed embodiments further provide methods and apparatuses that prevent incompatible ingredients from being combined under prescribed conditions. As an example, it may be beneficial to prevent use of one material source if another incompatible material source is selected for simultaneous use. The ability to prevent the drawing and/or mixing of incompatible ingredients becomes more significant when there are multiple pumps operating on the same fluid path. Thus, the disclosed methods and apparatuses can prevent the negative effects of combining incompatible materials during the fluid mixing process. The disclosed embodiments also provide methods and apparatuses for detecting fluid line degradation.

According to one aspect of the disclosure, a compounding apparatus is provided for controlling a compounding device to prepare an admixture from distinct material sources, the compounding apparatus including a delivery device that is configured to deliver the at least three selected materials from the material containers to the admixture container to facilitate formation of the admixture, the delivery device including a first pump and a second pump as well as a first line and a second line, the first pump being configured such that actuation thereof delivers a selected first of the at least three materials from its associated material container to the admixture container via the first line, the second pump being configured such that actuation thereof delivers a selected second material and third material of the at least three materials from a second material container and a third material container, respectively, to the admixture container via the second line, and a processor including a memory that is configured to store admixture data representing amounts of the at least three selected materials required to form the admixture, and line supply data that identifies either the first line or the second line as being appropriate to supply each of the at least three selected materials, the processor also including a controller that is configured to selectively actuate the first pump and second pump to supply the amounts of the at least three selected materials to the admixture container so as to facilitate formation of the admixture, the controller also being configured to selectively actuate the first pump and second pump so as to supply each of the at least three selected materials via the identified first line or second line.

According to another aspect of the disclosed embodiments, a process for controlling a compounding device to prepare an admixture from distinct material sources is provided and includes facilitating formation of an admixture by mixing at least three materials selected among multiple distinct materials using a compounding apparatus that includes a processor, the compounding apparatus being usable with an admixture container that is configured to contain the admixture, and also being usable with multiple material containers that are each configured to contain one of the at least three materials, the process including causing a delivery device to deliver the at least three selected materials from the material containers to the admixture container to facilitate formation of the admixture, the delivery device including a first pump and a second pump as well as a first line and a second line, the first pump being configured such that actuation thereof delivers a selected first of the at least three materials from its associated material container to the admixture container via the first line, the second pump being configured such that actuation thereof delivers a selected second material and third material of the at least three materials from a second material container and a third material container, respectively, to the admixture container via the second line, where the processor includes a memory that stores admixture data representing amounts of the at least three selected materials required to form the admixture, and line supply data that identifies either the first line or the second line as being appropriate to supply each of the at least three selected materials, selectively actuating the first pump and second pump to supply the amounts of the at least three selected materials to the admixture container so as to facilitate formation of the admixture, and selectively actuating the first pump and second pump so as to supply each of the at least three selected materials via the identified first line or second line.

According to another aspect of the disclosure, a compounding apparatus for facilitating formation of an admixture that involves mixing at least two materials selected among multiple distinct materials, whereby one material of the multiple distinct materials is incompatible with another material of the multiple distinct materials is provided. In this embodiment, the compounding apparatus is usable with an admixture container that is configured to contain the admixture, and is also usable with multiple material containers that are each configured to contain one of the materials and the compounding apparatus includes a delivery device that is configured to deliver the at least two selected materials from the material containers to the admixture container to facilitate formation of the admixture, the delivery device including first and second pumps, the first pump being configured such that actuation thereof delivers a selected one of the at least two materials from its associated material container to the admixture container, the second pump being configured such that actuation thereof delivers a selected other of the at least two materials from its associated material container to the admixture container, and a processor including a memory that is configured to store admixture data representing amounts of the at least two selected materials required to form the admixture, and incompatibility data identifying the one material that is incompatible with the other material, the processor also including a controller that is configured to selectively actuate the first and second pumps to supply the amounts of the at least two selected materials to the admixture container pursuant to the stored admixture data so as to facilitate formation of the admixture, the controller also being configured to prevent delivery of the at least two selected materials if the one material and other material that are incompatible with each other are both included in the at least two selected materials, wherein the controller prevents delivery of the at least two selected materials by causing one of the first pump and the second pump to deliver a third material of the multiple distinct materials to the admixture container.

According to another aspect of the disclosure, a process for facilitating formation of an admixture using a compounding apparatus, wherein the admixture involves mixing at least two materials selected among multiple distinct materials, whereby, one material of the multiple distinct materials is incompatible with another material of the multiple distinct materials is provided. The compounding apparatus includes a processor and is usable with an admixture container that is configured to contain the admixture, and the compounding apparatus is also usable with multiple material containers that are each configured to contain one of the materials. The process according to this embodiment includes causing a delivery device to deliver the at least two selected materials from the material containers to the admixture container to facilitate formation of the admixture, the delivery device including first and second pumps, the first pump being configured such that actuation thereof delivers a selected one of the at least two materials from its associated material container to the admixture container, the second pump being configured such that actuation thereof delivers a selected other of the at least two materials from its associated material container to the admixture container, wherein the processor includes a memory that stores admixture data representing amounts of the at least two selected materials required to form the admixture, and incompatibility data identifying the one material that is incompatible with the other material, selectively actuating the first and second pumps to supply the amounts of the at least two selected materials to the admixture container pursuant to the stored admixture data so as to facilitate formation of the admixture, preventing delivery of the at least two selected materials if the one material and other material that are incompatible with each other are both included in the at least two selected materials, wherein preventing delivery of the at least two selected materials includes causing one of the first pump and the second pump to deliver a third material of the multiple distinct materials to the admixture container.

The disclosed embodiments also provide methods and apparatuses for detecting and/or predicting degradation of fluid transfer lines (also referred to interchangeably as "transfer tubing" or "pump tubing" or "transfer set" or "transfer set tubing.") based upon various criteria. It is within the scope of the disclosed embodiments to incorporate mechanisms, including, but not limited to, the detection of: variations in the weight of a filled IV bag as compared to a baseline IV bag weight, variations in the number of rotor cycles as compared to a baseline number of rotor rotations and/or variations in the volume of fluid flowing through the fluid lines compared to a baseline volume of fluid that flows through the fluid lines for a known fluid admixture. Wear detection is another mechanism that is contemplated for detecting and/or predicting degradation of fluid transfer lines.

According to another aspect of the disclosed embodiment, a compounding apparatus is provided for facilitating formation of an admixture that involves mixing at least two materials selected among multiple distinct materials, the compounding apparatus being usable with an admixture container that is configured to contain the admixture, and also being usable with multiple material containers that are each configured to contain one of the materials, the compounding apparatus including a delivery device that is configured to deliver the at least two selected materials from the material containers to the admixture container to facilitate formation of the admixture, the delivery device including first and second pumps as well as first and second tubes, the first pump being configured such that actuation thereof delivers a selected one of the at least two materials from its associated material container to the admixture container via the first tube, the second pump being configured such that actuation thereof delivers a selected other of the at least two materials from its associated material container to the admixture container via the second tube, and a processor including a memory that is configured to store admixture data representing amounts of the selected at least two materials required to form the admixture, the memory storing a wear correction factor that is applied when a tube wear is detected, the processor determining the occurrence of tube wear through the steps of determining a current position of a roller associated with the first pump, monitoring revolutions of the roller in comparison to the current position, performing an in process calibration process if the number of revolutions of the roller exceeds the wear correction factor; an determining a tube wear correction factor based upon the number of revolutions of the roller, wherein the processor is configured to apply the tube wear correction factor to a pump roller controller.

According to another embodiment, a processing method for controlling a compounding device to detect degradation of a fluid line is provided which includes a processor for use with a compounding apparatus for facilitating formation of an admixture that involves mixing at least two materials selected among multiple distinct materials, an admixture container that is configured to contain the admixture, and multiple material containers that are each configured to contain one of the materials, the compounding apparatus including a delivery device that is configured to deliver the at least two selected materials from the material containers to the admixture container to facilitate formation of the admixture, the delivery device including first and second pumps as well as first and second tubes, the first pump being configured such that actuation thereof delivers a selected one of the at least two materials from its associated material container to the admixture container via the first tube, the second pump being configured such that actuation thereof delivers a selected other of the at least two materials from its associated material container to the admixture container via the second tube, the processor including a memory that is configured to store admixture data representing amounts of the selected at least two materials required to form the admixture, and the memory storing a wear correction factor that is applied when a tube wear is detected, the processor configured to determine the occurrence of tube wear through the steps of determining a current position of a roller associated with the first pump, monitoring revolutions of the roller in comparison to the current position, performing an in process calibration process if the number of revolutions of the roller exceeds the wear correction factor, and determining a tube wear correction factor based upon the number of revolutions of the roller, wherein the processor is configured to apply the tube wear correction factor to a pump roller controller.

BRIEF DESCRIPTION OF THE DRAWINGS

The disclosed subject matter of the present application will now be described in more detail with reference to exemplary embodiments of the apparatus and method, given by way of example, and with reference to the accompanying drawings, in which:

FIG. 1 is a perspective view of an exemplary embodiment of a compounding system made in accordance with principles of the disclosed subject matter.

FIGS. 3A-G are partial perspective views of the exemplary embodiment of FIG. 1 in sequential positions in which an exemplary transfer set including manifold and output lines are aligned and connected to exemplary valve actuators, sensor block and pumps.

FIG. 4A is a top view of an exemplary manifold, strain relief, union junction, and output line made in accordance with principles of the disclosed subject matter.

FIGS. 6A-C are cross section views taken along lines 6A, 6B, and 6C of FIG. 4A, respectively.

FIGS. 16-34 are screen shots of an exemplary controller interface for use with a compounding device or system made in accordance with principles of the disclosed subject matter.

FIG. 36 is a flow chart of an exemplary process that can be used to operate the compounding device of FIG. 1 in accordance with the principles of the disclosed subject matter.

FIG. 37 is a flow chart illustrating logic for controlling a compounding process of the compounding device in accordance with the principles of the disclosed subject matter.

FIGS. 38a-38d together comprise a flow chart illustrating logic for controlling pumps or the compounding process in accordance with the principles of the disclosed subject matter.

FIGS. 40a-40c together comprise a flow chart illustrating logic for controlling the compounding process to detect fluid line degradation in accordance with the principles of the disclosed subject matter.

DETAILED DESCRIPTION OF EXEMPLARY EMBODIMENTS

Methods and systems for admixture compounding are described. In the following description, for purposes of explanation, numerous specific details are set forth in order to provide a thorough understanding of example embodiments. It will be evident, however, to one of ordinary skill in the art that these embodiments may be practiced without these specific details.

The flow chart blocks in the figures and the description depict logical steps and/or reason code from a reason code module to operate a processor, computer system, controller, compounding system, etc. to perform logical operations and control hardware components and devices of the embodiments using any appropriate software or hardware programming language. In one embodiment, object code in a processor can generate reason codes during execution of the associated logical blocks or steps.

Figure 2A:
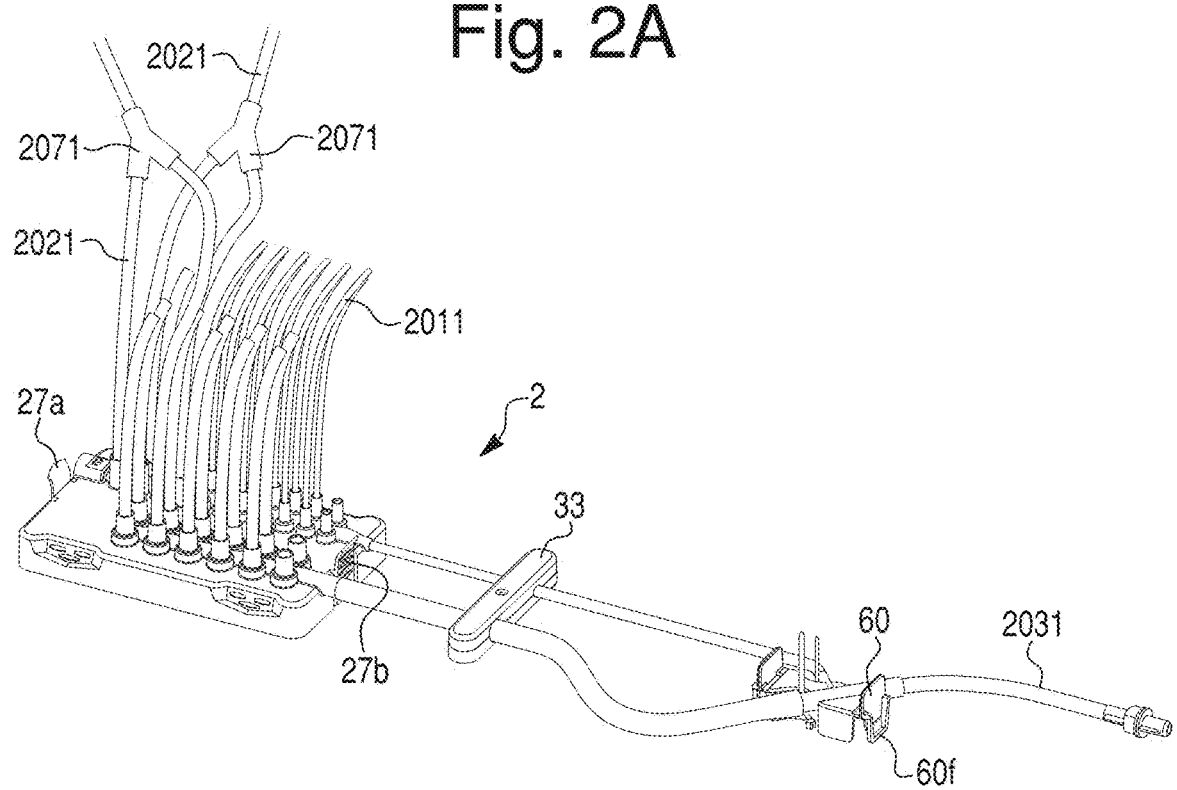
FIG. 2A is a perspective view of the exemplary transfer set of FIG. 1.
Figure 2B:
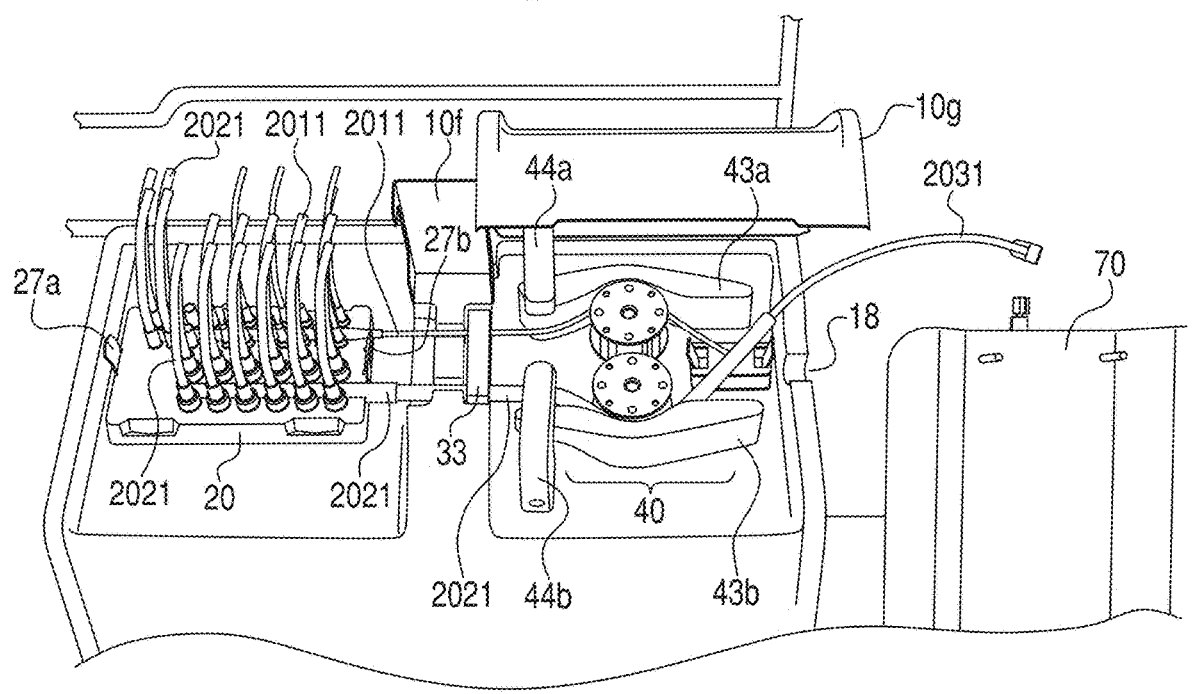
FIG. 2B is a partial perspective view of the exemplary embodiment of FIG. 1.

FIGS. 1 and 2B are two different perspective views of an exemplary embodiment of a compounding system 1 made in accordance with principles of the disclosed subject matter, with safety lids which are also hereinafter referred to as a sensor bridge cover 10f and a pump cover 10g in a closed position and opened position, respectively. The system 1 can be used to compound or combine various fluids from small or large containers 4a, 4b and consolidate the fluids into a single/final container, such as an intravenous fluid bag 80, for delivery to a human or animal patient, or to a lab for diagnostics, or to a storage facility for later sales or use. In one example, the system 1 can include a plurality of small supply containers 4a and large supply containers 4b each attached to an ingredient frame 3, a housing 10 having at least one pump (41, 42) (See FIG. 3A), a transfer set 2 (See FIG. 2A) that is selectively connectable to the housing 10 and that includes a manifold 20 attached to a plurality of micro input lines 2011, macro lines 2021, a controller connection 90, a controller 2900, and a discharge tray 70 in which a final container, such as IV fluid bag 80, can rest while connected to an output line(s) of the transfer set 2. In the embodiments, the pumps 41, 42 can include, but are not limited to peristaltic pumps, gear pumps, vacuum pumps, syringe pumps, reciprocating pumps, constant pressure pumps, or any other appropriate pump that can accomplish the functions of the system 1. The pumps in the current disclosure can be referred to individually as first pump 41 and second pump 42, and in some embodiments as a micro pump 41 and a macro pump 42 when the pumps are connected to the respective micro and macro flow paths in the system 1. In some embodiments, the first and second pumps 41, 42 are reciprocating pumps, and the rotors for the reciprocating pumps can be referred to herein as first, or micro pump, rotor 41 and second, or macro, pump rotor 42. The identification of the pumps 41,42 are exemplary, and could be substituted for one another such that the macro pump is the second pump and the micro pump is the second pump, depending on the flow path to which each pump connects. Further, the embodiments intend to include, or otherwise cover, a multi-channel pump, where a first channel can function as the first pump 41 and a second channel can function as the second pump 42. The transfer set 2 is intended to be a sterile, disposable item. In particular, the transfer set 2 can be configured to create or compound many different mixtures or prescriptions into appropriate receiving bags 80 for a predetermined time or predetermined volume limit. Once the transfer set 2 reaches its predetermined time and/or volume limit, the set 2 can be disposed of and replaced by a new transfer set 2. In other words, the transfer set 2 is a pharmacy tool that is to be used for a full compounding campaign, for example, for a 24 hour compounding run in which prescriptions for multiple patients are filled during that time period. Before beginning a given compounding procedure, the operator loads the various components of the transfer set 2 to the housing 10 of the compounding system 1.

As shown in FIG. 1, the transfer set 2 (See FIG. 2A) can be connected (or connectable) between the at least one input container (such as micro container(s) 4a and/or macro container(s) 4b) and the output container (such as an IV fluid bag 80) via a plurality of lines (for example, micro input line(s) 2011 and/or macro line(s) 2021). The transfer set 2 can include a plurality of micro and macro lines 2011, 2021 extending therethrough, a manifold 20, a strain relief clip 33, a union junction 60 and an output line 2031. The micro and macro lines 2011, 2021 run through at least one manifold 20 such that fluids from each of the separate supply containers 4a, 4b can be at least partially mixed in the manifold 20 prior to further mixing at junction 60 located downstream of pump 40. The transfer set 2 is connectable to the main housing 10 of the system 1 and provides the connection between the input supply container(s) 4a, 4b and the output container. The housing 10 provides (among other features) pumping and control functionality to safely and efficiently select and deliver exact quantities of various fluids from containers 4a, 4b through the transfer set 2 to the output container. The manifold 20 can include two separate flow paths such that compounding can continue along a first flow path while the second flow path is interrupted.

The transfer set 2 macro lines 2021 and micro lines 2011 are all attached to specific inlet tubing ports (i.e., 20a and 20b) of the manifold 20. The free or upstream ends of these lines are each uniquely marked with a permanent identification tag 802. In this exemplary embodiment, the identification tag 802 is a bar coded flag or sticker. The identification tag 802 provides one-to-one traceability and corresponds to a specific instance of the inlet tubing port (20a or 20b) to which it is attached. The source containers 4a and 4b possess unique data identifying the type and kind of fluids contained therein. This data can also be formatted in bar code format and placed onto tag 801. During use, the attached source containers (i.e., 4a and 4b) can be linked in the controlling software to the specific lines 2011 or 2021 by linking the source container data on the bar code format located on tag 801 to the bar code (or other identification information) located on the attached line identification tag 802. Once connected, correlated and linked in this way, when the compounding device requires the specific ingredient, the software links established above determines which valve actuator 102a' or 102b' must be turned in order to introduce the required or intended source fluid into the compounded receiving bag 80.

Connection of the transfer set 2 to the main housing 10 can be initiated by connecting the manifold 20 to the housing 10. The manifold 20 can include a plurality of ports, such as micro input line port(s) 20a and/or macro input line port(s) 20b. The lines of the transfer set 2 can include a plurality of lines, such as micro lines 2011 and/or macro lines 2021 and/or combination micro/macro line(s) referred to as flex line(s). The plurality of lines can correspondingly connect to the above-referenced micro container(s) 4a and/or macro container(s) 4b at an input end of respective micro and macro line(s) 2011, 2021. An output end of each of the micro and macro line(s) 2011, 2021 can be connected to the manifold 20. The manifold 20 can be selectively connected to the housing 10 such that at least one valve 21a, 21b located in the manifold 20 can be aligned with a valve actuator 102a' and 102b' that can be incorporated in a stepper motor 102a, 102b located in the housing 10 (which will be described in more detail below).

In this exemplary embodiment, as shown in FIGS. 3A and 3B, when installing the transfer set 2 onto housing 10, the manifold 20 is connected to a top left side of housing 10 within a shallow tray indent 10c in the upper surface of the housing 10. The shallow tray 10c allows spilled fluids or leaks to run off the pump housing 10 in order to prevent ingress of the fluids to the internal electronics and mechanisms of the compounding system 1. In FIG. 3A, transfer set 2 and manifold 20 are not yet in position and are located above the housing 10 as if a user is starting the process of placing the transfer set 2 onto the housing 10 and preparing for use of the compounding system 1. The transfer set 2 includes a manifold 20 that has two distinct channels: a first channel 24a that connects to a plurality of micro lines 2011 and/or macro lines 2021, and a second channel 24b that connects to a plurality of macro lines 2021. Of course, in other embodiments the first and second channels could each be connected solely to micro, macro, flex, or other types of lines, respectively, or could be connected to combinations of micro, macro, or other types of lines. The first channel 24a and the second channel 24b are located in the manifold 20 and can be completely separate from each other (i.e., in fluid isolation from each other), such that no fluid from the first channel 24a mixes with fluid from the second channel 24b. The channel is considered that portion or area in the manifold through which fluid can flow. In this embodiment, a micro outlet 25a and a macro outlet 25b can be located on a downstream side of manifold 20 and connected to micro line 2011 and macro line 2021, respectively. It should be noted that the lines downstream of the manifold (e.g., outlet lines, or micro line 2011 and macro line 2021) can incorporate different tubing as compared to the inlet lines 2011, 2021 that supply fluid to the manifold 20. For example, the inlet lines can include tubing made of more or less rigid material as compared to the outlet lines, and can also include tubing made with larger or smaller diameter openings, or made of larger or smaller side wall thicknesses. In addition, the color of the inlet lines can be different from the color of the outlet lines, and the lines can also have different surface textures either inside or outside of the tubing. For example, the texture on the inside could be configured to promote or prevent turbulence, depending on the application and location of the line.

A sensor structure 29 can be located in the manifold (See FIGS. 7A and 7B) and is configured to trip a sensor 2901 (See FIG. 15) located in the housing 10 that tells the system that the manifold 20 is in a correct/operational position. Alternatively, the sensor 2901 can be configured to confirm the presence and gross positional information for the manifold 20, but not necessarily configured to confirm that the position is fully operational. The sensor structure 29 can include a magnet 29m that goes into a housing 29h and provides a signal to (or actuates) the sensor 2901 in the housing 10 which indicates that manifold 20 and transfer set 2 are properly (i.e., securely) in place (See FIG. 7A). Software used with the system can be configured such that the compounder 1 will not operate/function when sensor 2901 does not sense or is not actuated by the magnet 29m (i.e., when the manifold 20 is not in proper position with respect to the housing 10). After the manifold 20 is secured to the housing by clips 27a, 27b located on opposing ends of the manifold 20 (See FIG. 2B), a strain relief clip 33 can be seated onto the housing. The strain relief clip can be pre-assembled and attached to both the micro line 2011 and macro line 2021. When installed, the strain relief can be placed to the right and immediately adjacent a sensor bridge 10e that forms a right wall of the shallow manifold tray indent 10c in which the manifold 20 is seated. The strain relief clip 33 can be pre-assembled to the transfer set 2 to ensure ease of use by the end user.

Figure 3C:
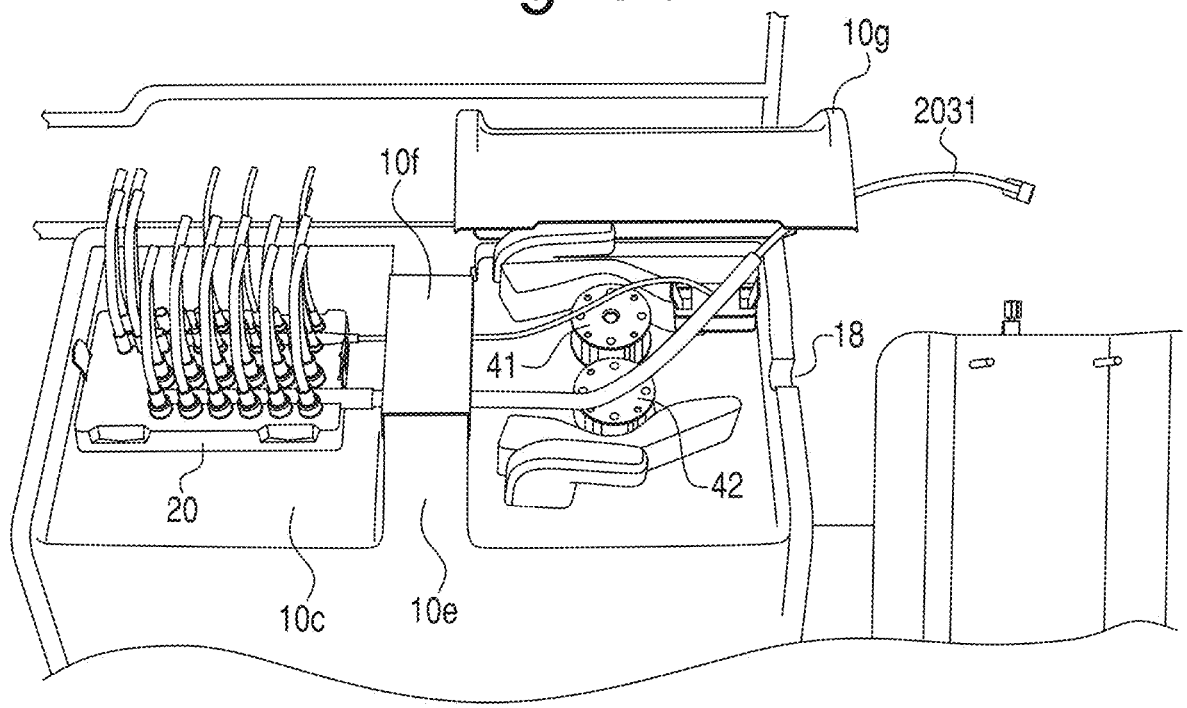

As shown in FIG. 3C, once the manifold 20 is attached to the housing 10 and the strain relief clip 33 is in place, the sensor bridge cover 10f can be closed over the sensor bridge 10e in order to protect the sensors and strain relief clip 33 from inadvertent contact and/or contamination from dust, liquids or other contaminants. The sensor bridge 10e can include a sensor or sensors (for example, an ultrasonic sensor, photo sensor, or other sensor) acting as a bubble detector and/or occlusion detector.

Figure 3D:
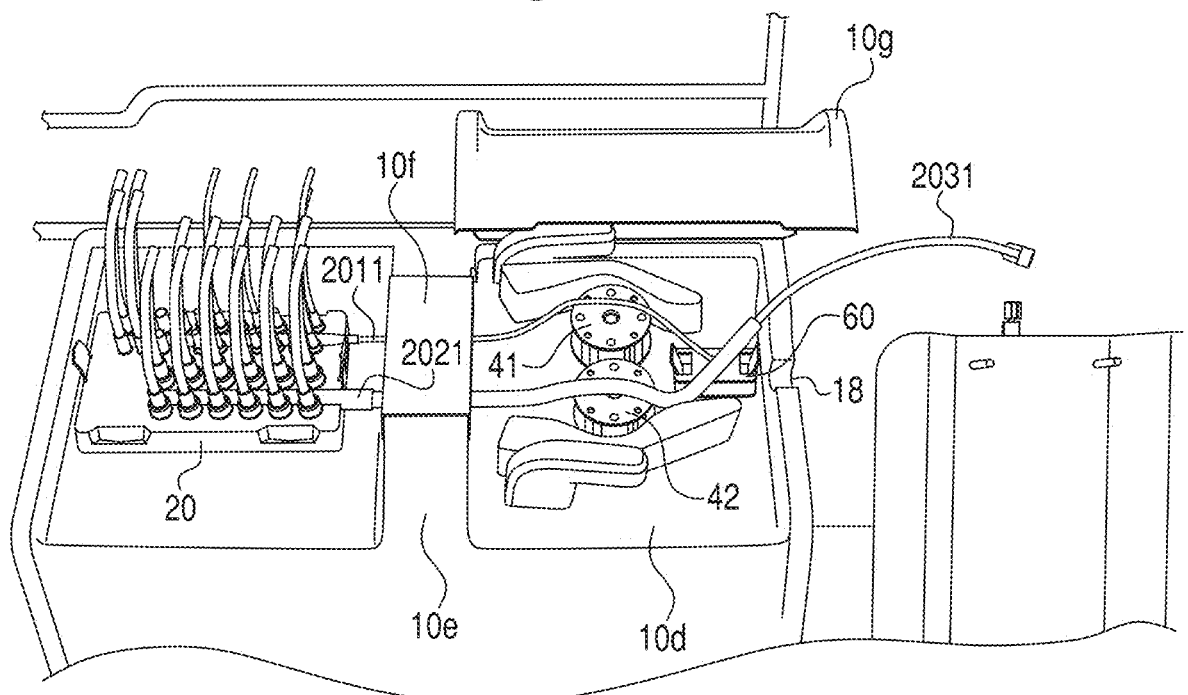

FIG. 3D shows an exemplary next step of installing the transfer set 2, which includes connecting the union junction 60 to the housing by snapping clip locks 60f (see FIGS. 10 and 11) located on the junction 60 to mating locks formed on an upper surface of the housing 10 and to the right of the pump 40. The output line 2031 can be set within an output guide 18 (See FIG. 3A) formed in an outer wall that defines a second shallow pump tray indent 10d in the upper surface of the housing in which the pump 40 is located.

Figure 3E:
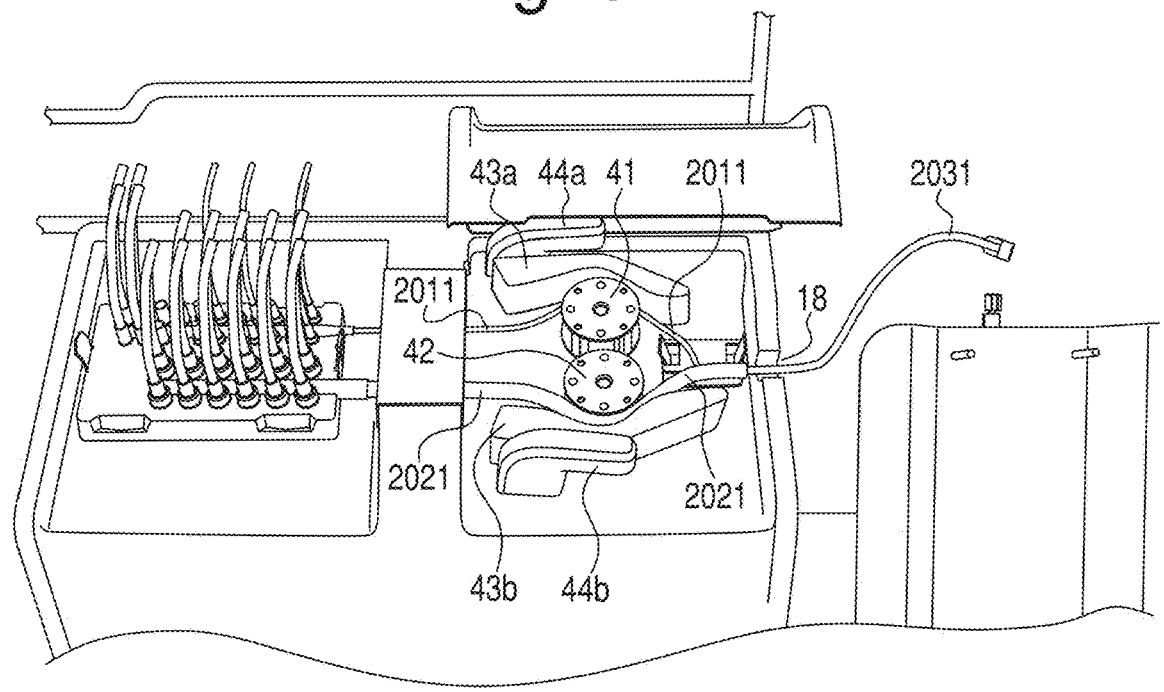

As shown in FIG. 3E, once the junction 60 and output line 2031 are in place, the micro line 2011 and macro line 2021 can be seated within the peristaltic pump 40. Alternatively, the union junction 60 can also be snapped into place after installing the pump tubing around a rotor for each pump 41, 42. In particular, micro line 2011 can be placed about the outer periphery of first rotor 41 and macro line 2021 can be placed about the outer periphery of second rotor 42. In this position, the micro line 2011 will be located between the first/micro rotor 41 and the first/micro platen 43a, and the macro line 2021 will be located between the second/macro rotor 42 and the second/macro platen 43b.

Figure 3F:
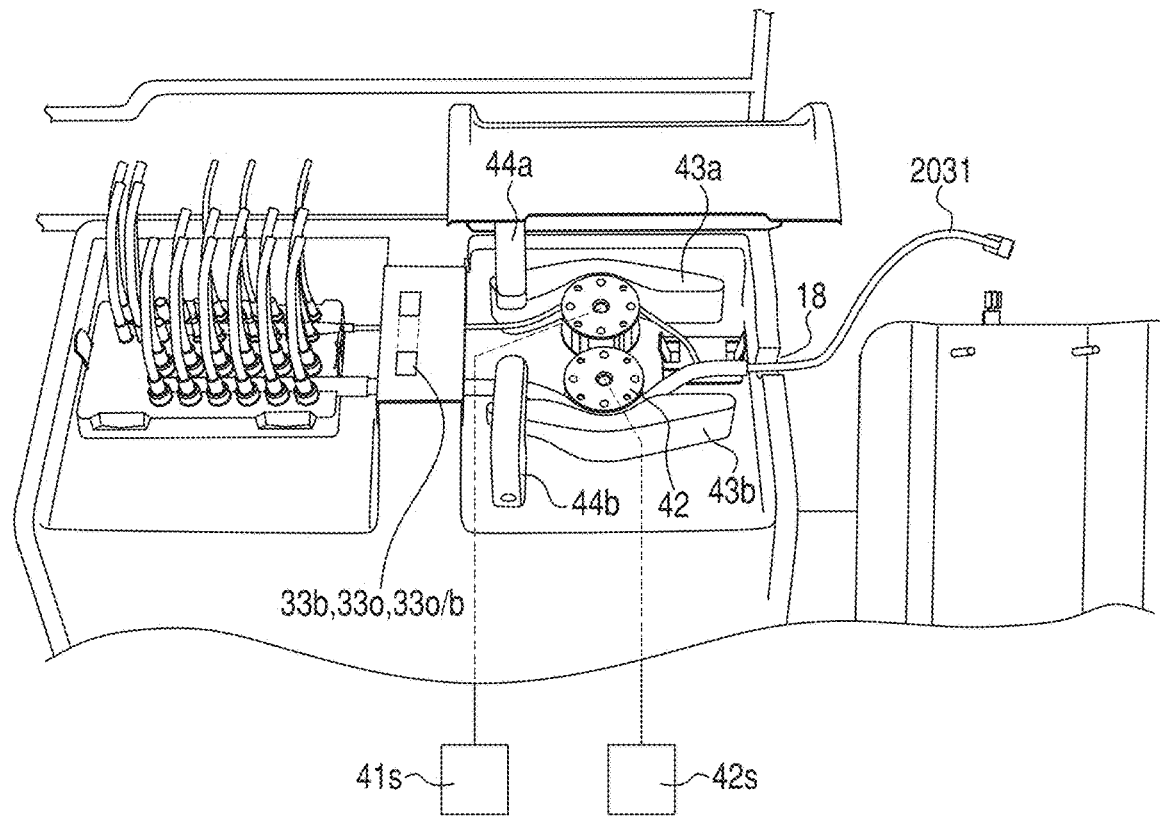

FIG. 3F shows an exemplary next step for connecting the transfer set 2 to the housing 10, which includes rotating the first/micro platen lock 44a clockwise to lock the platen 43a at its closed position relative to the first rotor 41, and rotating the second/macro platen lock 44b counter-clockwise to lock the second platen 43b at its closed position relative to the second rotor 42. In this position, when the rotors 41 and 42 are actuated and when any one of the valves 21a, 21b are rotated to the open position, each of the rotors will draw fluid(s) through respective lines 2011, 2021 through peristaltic forces/actions. If one of the valves 21a or 21b is not opened and the pump rotor operates, the peristaltic forces will create a vacuum between the manifold channels 24a, 24b inside the micro lines 2011 or macro lines 2021 between the manifold 20 and the pump rotors 41, 42 possibly resulting in an occlusion of the affected line. The occlusion will be detected as the wall of the micro lines 2011 and macro lines 2021 will partially collapse and this will be measured by the occlusion sensor within the sensor bridge 10e. The occlusion sensor 33o can be an optical sensor, a force based sensor, pressure sensor, an ultrasonic sensor or other known sensor for determining whether an occlusion has occurred in the line. In another embodiment, an occlusion sensor 33o and a bubble sensor 33b can be incorporated into the sensor bridge 10e. Alternatively, a combined sensor 33o/b or sensors 33o, 33b can be incorporated into the strain relief 33, or at other locations along the system 1, and can be integrated into the strain relief 33 or bridge 10e or can be separate and independent structures that are attached to the system 1.

Figure 3G:
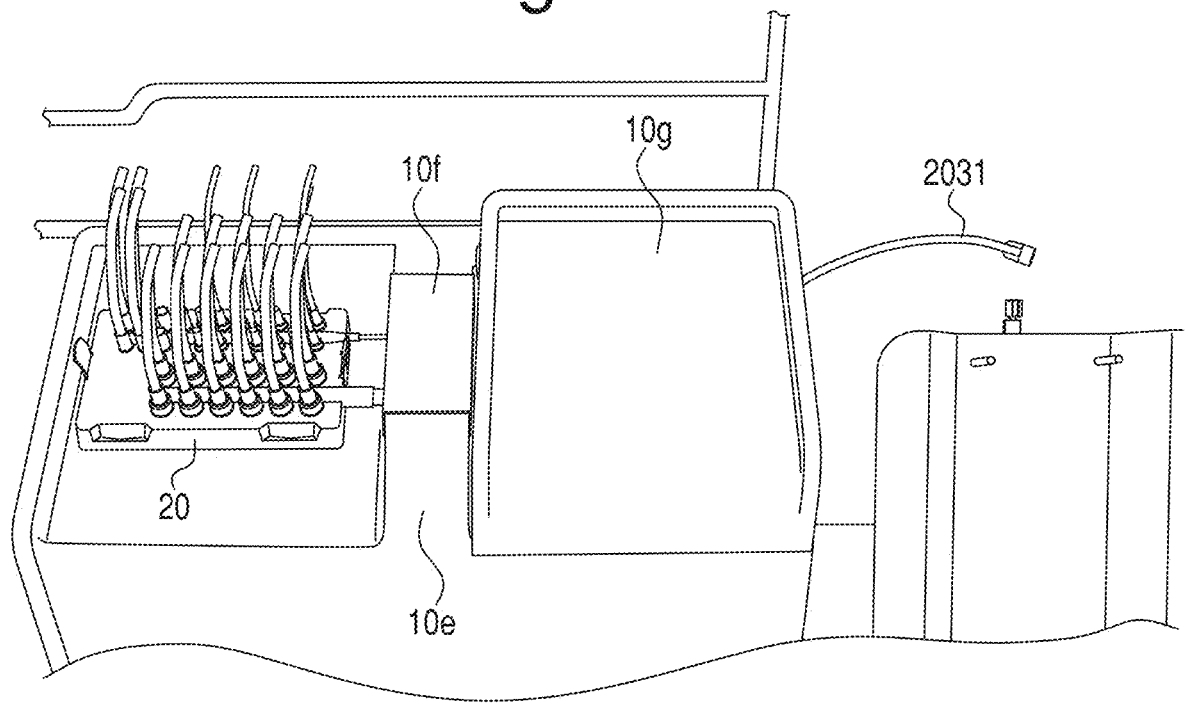

FIG. 3G shows an exemplary final step in the setup of the system 1, in which the pump cover 10g is closed over the pump 40 to protect the pump 40 from contact with other devices/structures/persons and to protect the pump 40 and associated lines 2011, 2021 from contamination from dust, liquids, or other contaminants. Each of the sensor cover 10f and pump cover 10g can include a magnet or other type of sensor or locking mechanism to ensure the covers are in place during operation of the system 1.

Once the transfer set 2 is correctly connected to the housing 10, input/storage containers 4a, 4b, and receiving bag 80, and the covers 10f and 10g are closed, calibration of the system 1 and then processing and compounding of various fluids can take place.

Figure 3H:
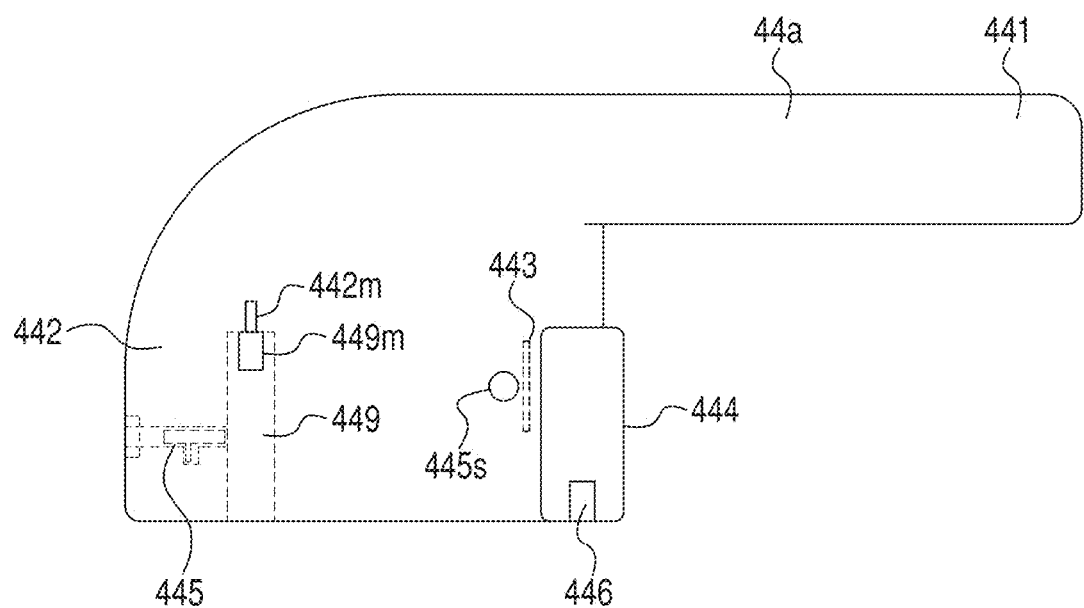
FIG. 3H is a side view of the platen lock shown in FIGS. 3A-3F.

FIG. 3H depicts an exemplary embodiment of a platen lock 44a. The platen lock 44a can be configured to rotate about a rotational axis and cause a cam 444 to come into resilient contact with the platen 43a. The cam 444 can include a biasing member, such as, for example, a spring 443, including, but not limited to, a plate spring, coil spring, or other type of spring to cause the cam 444 to keep in constant contact with and apply a preset and constant force to the platen 43a, which in turn keeps a constant or preset force on the micro line 2011 located between the platen and the rotor 41 to ensure accurate and predictable volumetric output by the pump 40 over the life of the transfer set. The spring 443 can be an important factor in the wear of the tubing lines during compounding, which can also impact the output of the pump 40.

Accuracy can also be a function of pump tubing inner diameter, tubing wall thickness, and the spacing between rollers and platen. Accuracy is also affected by the speed of rotation, but both motors can have the same accuracy.

The platen lock 44a can have a streamlined appearance, being configured substantially as a simple, L-shaped structure with an overhang upper extension 441 and a rotational lower extension 442. The lower extension having a longitudinal axis about which the platen lock 44a rotates. The platen lock 44a can be made from aluminum or other rigid material such as plastics, ceramics and/or other metals or alloys. The simple structure provides a user a sense of efficiency in the nature of operation of the platen lock structure 44a. The lower extension 442 can be configured with an opening to slide onto and attach to rotational post 449 extending from/within the housing 10. The platen lock 44a can lock onto the post 449 via a simple friction fit, a spline type relationship between the post 449 and the opening in the lower extension 442, or other structural configuration. In an alternate embodiment, a set screw structure 445 can be provided in the lower extension 442 for quick connection to the rotational post 449 that extends from the housing 10 of the compounding system 1. In the embodiment depicted in FIG. 3H, a set screw 445s can be used to set the preload on the spring 443 that is contained inside the platen lock 44a, 44b. This spring 443 applies force on the platen 43a, 43b and ultimately squeezes the platen 43a, 43b against the respective rotor 41, 42. A magnetic lock structure 449m and 442m can also (or alternative to the screw structure 445) be provided and can have multiple functions, including: locking the platen lock 44a to the housing 10 to prevent removal of the platen lock 44a from the housing 10 until the magnetic locks 449m and 442m are released. The location of platen lock 44a with respect to platen 43a can be achieved by a detent position on the backside of the platen 43a. As the platen lock 44a is rotated against the platen 43a towards the lock position, the cam 444 follows a profile on the back of the platen which includes a raised feature to compress the cam 444, which the user has to rotate past to reach the final lock position. The action of the cam over this feature provides feedback to the user that the lock point has been reached, and mechanically maintains this lock position due to the cam sitting in a cavity feature. Continued rotation past the desired lock point can be prevented by providing hard stop geometry in the platen profile such that the cam cannot get past the hard stop geometry. The location of the cam 444 when the platen lock 44a is in this lock position, is where sensor 2904a is tripped via a magnet 446 embedded in the bottom of cam 444. The coupling of lock arm 44a to the post 449 is achieved via a pair of magnets, the first 449m embedded in the top of post 449, the second 442m at the end of the receiving bore in the lower extension 442 of the lock arm 44a.

Another benefit of this exemplary embodiment of the system 1 is that the configuration allows the operator to easily remove the platens 43a, 43b and platen lock components 44a, 44b from the pump housing for cleaning without the use of tools. Both platens 43a, 43b can be removed by simply pulling them upward and away from the pump housing surface 10d.

In addition, both rotors 41, 42 can be removed without tools by simply unscrewing thumb screws that can be provided at a center/rotational axis of the rotors 41, 42. Because the rotors 41, 42 can be interchangeable, their life can be extended by swapping their positions after cleaning, e.g., macro to micro and micro to macro.

The pump 40 as a peristaltic pump can include first and second pump rotors 41, 42 that are each mounted upon and separately rotated by a respective stepper motor 41s, 42s (See FIG. 3F). Each of the stepper motors 41s, 42s can have a preset microsteps per revolution value that is relatively high (for example, on the order of $10^3$ greater than the microsteps per revolution value for the stepper motors 102a, 102b used to rotate valves 21a, 21b located in manifold 20, as described in more detail below). The high value of microsteps per revolution for the stepper motors 41s, 42s allows for greater accuracy or precision in fluid delivery for the system 1. Each of the stepper motors 41s, 42s can be connected to controller 2900 and can be separately, sequentially, serially, concurrently or otherwise controlled to cause each of the rotors 41, 42 to rotate a known and predetermined amount and possibly at a predetermined speed such that a highly accurate amount and timing of material flow through the compounding device can be achieved. In addition, steppers 41s, 42s can be provided with absolute encoders that are in communication with controller 2900 to provide explicit positioning control of the steppers 41s, 42s.

The first, or micro, and second, or macro, pump rotors 41, 42 can be substantially identical to each other such that they can be interchanged. For example, in one embodiment, the macro rotor 42 can be configured to rotate more than the micro rotor 41 and will thus be subject to higher wear. Thus, at some point during a break in operation of the compounding system 1, the macro rotor 42 can be interchanged with the micro rotor 41 such that the rotor 41 will act as the macro rotor and be subject to the heightened wear for a time period. In this manner, the life of both rotors 41, 42 can be extended.

The cam 444 and the spring 443 can also be configured to provide a known force to the platen 43a when the platen lock 44a is in a certain rotational position such that the platen lock 44a is effectively locked in place due to both resilient forces and frictional forces that occur when at the certain position relative to the platen 43a. In other words, once the platen lock 44a passes a predetermined rotational position, resilient force acting on the platen lock 44a by the platen 43a tends to cause the platen lock to continue its clockwise rotation. A sensor, such as a magnet 446, can be provided in the platen lock 44a and configured to trip a corresponding sensor 2904a in the housing 10 that tells the system the platen lock 44a is in the correct position. However, if there is a rotational stop located in either the post in the housing or the lower extension 442, the platen lock 44a will be unable to rotate further in the clockwise rotational direction and will simply maintain the above-referenced known resilient force (due to cam 444 and cam spring 443) with the resilient force also acting to prevent release of (counterclockwise rotation of) the platen lock 44a. Unlocking the platen lock 44a from the platen 43a in this case would simply require the operator to overcome the resilient and frictional forces of the cam in the detent position tending to hold the structures in place. It should also be noted that the platen lock 44b and platen 43b can be configured in a similar manner as described above with respect to the platen lock 44a and platen 43a, except that locking would occur in a counterclockwise rotational motion.

Figure 4B:
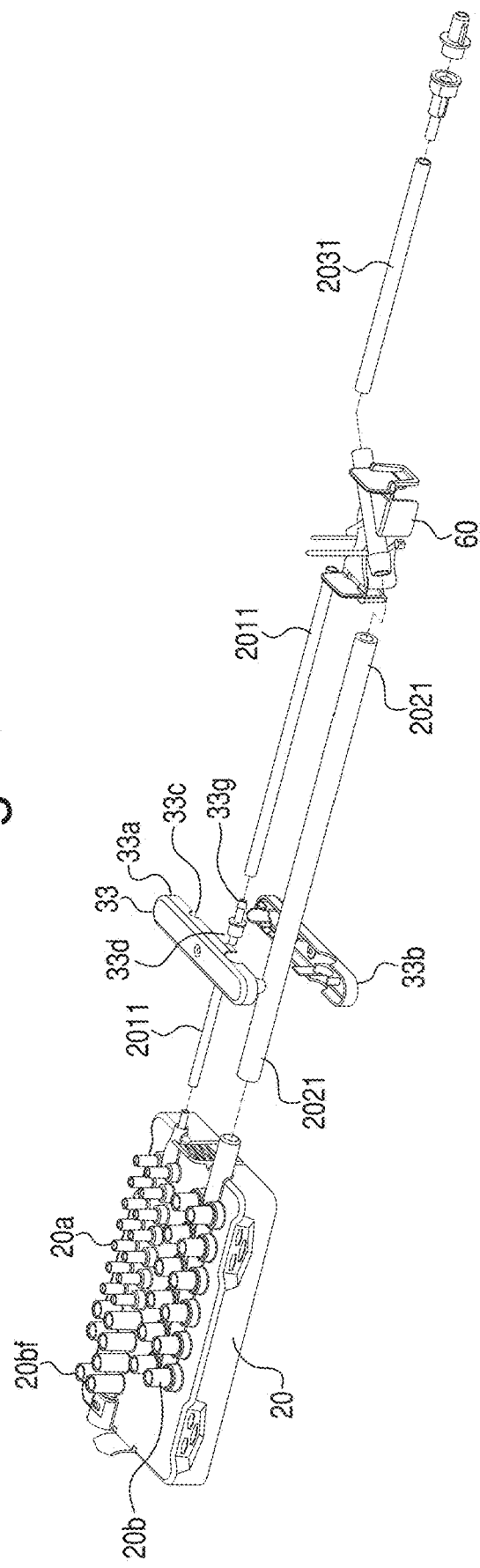
FIG. 4B is a perspective exploded view of the structures shown in FIG. 4A.

FIGS. 4A and 4B show a portion of an exemplary transfer set 2 that includes a manifold 20 connected via micro line 2011 and macro line 2021 to a strain relief clip 33. Micro line 2011 and macro line 2021 extend past the strain relief clip 33 and eventually combine or merge at the union junction 60, resulting in a single outlet line 2031 for the transfer set 2. The macro lines 2021 can be portions of the same continuous tubing structure. By contrast, in this example, micro lines 2011 are separate structures joined together by shunt 33g. The shunt 33g can be made from a material that is harder than the micro lines 2011. For example, the micro lines 2011 can be made from silicone tubing while the shunt 33g can be made from a relatively more rigid PVC material. The shunt 33g provides extra rigidity such that the strain relief clip 33 can connect securely thereto without causing the inner diameter of the shunt 33g to be squeezed or otherwise reduced. One or more collars 33d can be provided on the shunt 33g to lock to the clip 33 and prevent the shunt 33g from moving along a longitudinal axis of the micro lines 2011. Additional collars are contemplated so that manufacturing can be easier with respect to consistently locating/assembling of the manifold set structures. By contrast, the macro line 2021 can be sufficiently large enough in diameter and thickness such that its inner diameter is not squeezed or reduced when the clip 33 is attached thereto. Thus, when the strain relief clip 33 is attached to the micro lines 2011 and macro line 2021, the clip 33 does not significantly change the inner diameter characteristics for the lines while preventing forces acting along the longitudinal axes of the lines from being transmitted past the clip 33. Thus, when the micro line 2011 and macro line 2021 are connected about a respective rotor 41, 42 of the peristaltic pump 40, the rotary forces acting on the lines do not translate along the micro and macro input lines back towards the manifold 20 and the bubble and occlusion sensors. The strain relief clip 33 acts as a damper to minimize transmission of linear forces and vibrations from the pump 40 to the manifold 20. Minimizing these forces and vibrations optimizes the functionality of the bubble and occlusion sensors that would otherwise be impacted by changes in tubing tension as the tubing is pulled by the peristaltic action of the pump. Similarly, the strain relief provides a fixed position on the set 2 relative to the manifold 20 to facilitate installation of the tubing or line segments through the occlusion and bubble sensors 33o, 33b, 33o/b and maintains a repeatable tension on these line segments.

Figure 5:
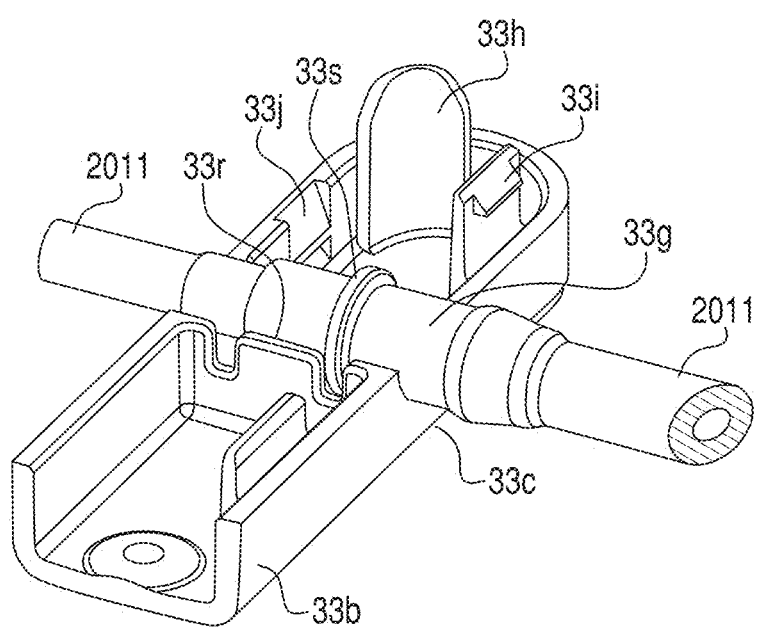
FIG. 5 is a partial perspective view of the strain relief shown in FIG. 4A.

The strain relief clip 33 can be of various shapes, and in the embodiment shown in FIG. 5 the clip 33 is configured as a two piece clam shell type design in which an upper portion 33a can be attached to a lower portion 33b by clips 33i that are integrally formed at locations about a perimeter of each portion 33a and 33b, and mate with snap latch receptacles 33j in an opposing portion 33a, 33b. Throughways 33c can be formed as half cylindrical cutouts in the upper portion 33a and lower portion 33b. A guide sleeve 33h can be provided at a corner of one of the clam shell portions 33a, 33b to guide the opposing claim shell portion 33a, 33b into engagement when coupling the clam shell portions 33a, 33b. The micro line 2011 and macro line 2021 can pass through these throughways 33c and be locked to the strain relief clip 33 by a series of ridges 33r that connect to mating ridge 33s in the shunt 33g and/or to the macro line 2021 itself. It is possible that the strain relief parts 33a and 33b are in fact identical so that the above described process and configuration is possible with the use of two instances of the same component.

Figure 6A:
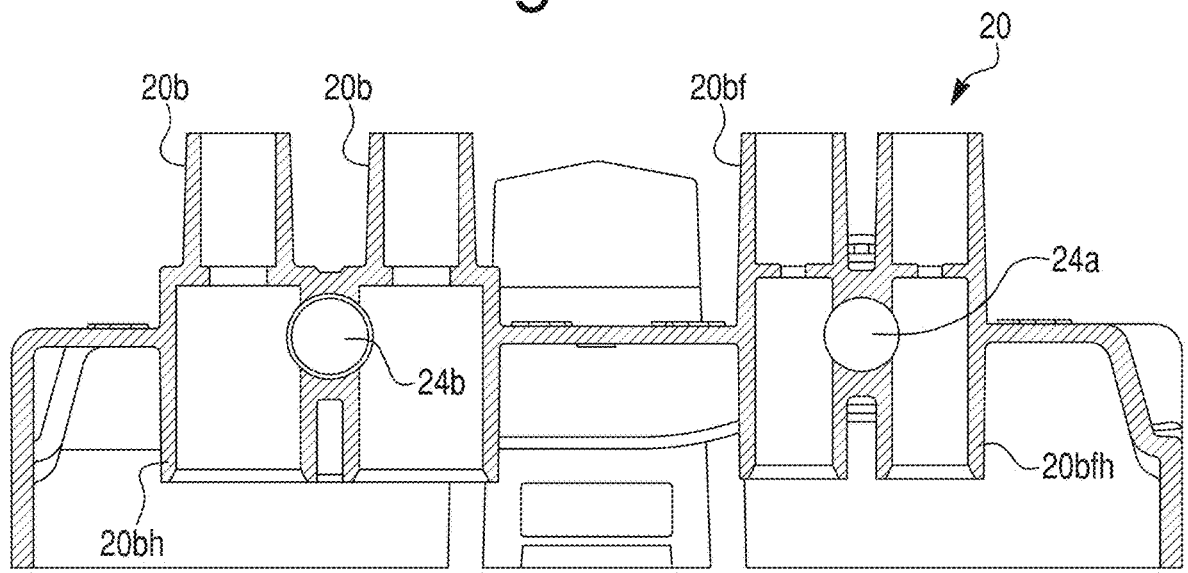
Figure 6B:
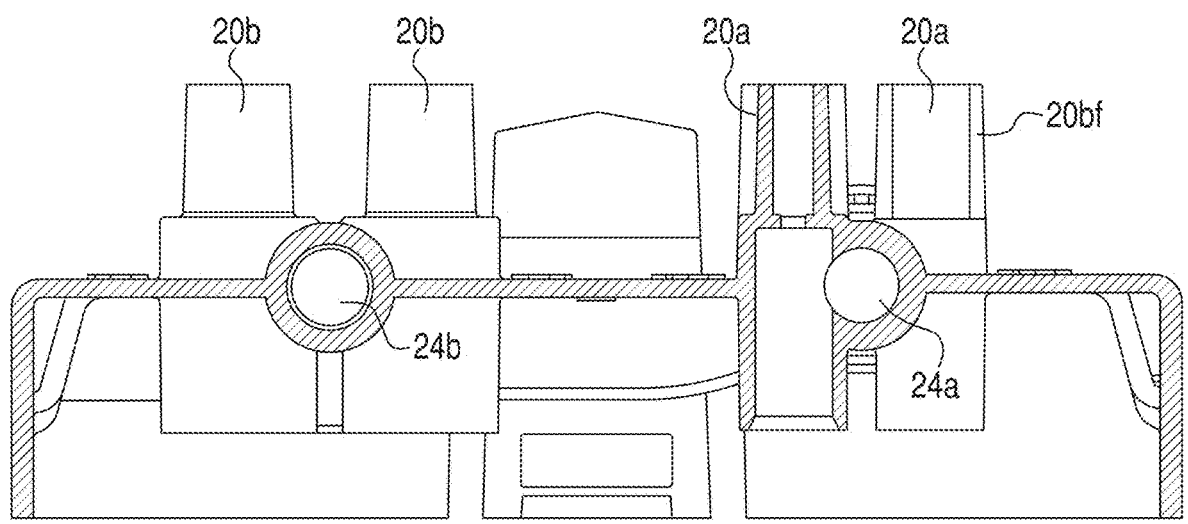

FIGS. 6A-6C show various cross-sections of the exemplary manifold 20 of FIG. 4A without valve structures located therein for clarity. The cross section shown in FIG. 6A depicts two sets of ports: two macro ports 20b and two flex ports 20b f that are each cylindrical in shape and are in fluid communication with a valve housing 20bh and 20bfh, respectively, located immediately underneath the ports 20b and 20bf. The ports 20b and 20bf are configured such that a macro line 2021 can be slid into the inner periphery of the upward and outward facing cylindrical opening in the ports 20b and 20bf for attachment thereto. Thus, the ports 20b and 20bf can be connected to various macro source containers 4b via the lines 2021 attached to the ports 20b and 20bf. A valve 21b, 21a (to be described in more detail below) can be located within the valve housing 20bh, 20bfh, respectively, located beneath the ports 20b, 20bf. When the valve 21b, 21a is located in the housing 20bh, 20bfh, the valve 21b, 21a selectively connects the fluid located in line 2021 with the fluid located in channel 24b, 24a of the manifold depending on the valve's rotational position within the housing 20bh, 20bfh.

The manifold described above can, in the exemplary embodiment, be formed (e.g., molded) as one unitary structure 20 including all of the features 20a, 20b, 20bf, 20ah, 20bh, 20bfh, 24a, 24b, 25b, 26, 27a, 27b, and 29. Also, it is possible to join any or all separate structures (components) 20a, 20b, 20bf, 20ah, 20bh, 20bfh, 24a, 24b, 25b, 26, 27a, 27b, and 29 in any combination into a manifold assembly 20 to achieve the same purpose.

Figure 7A:
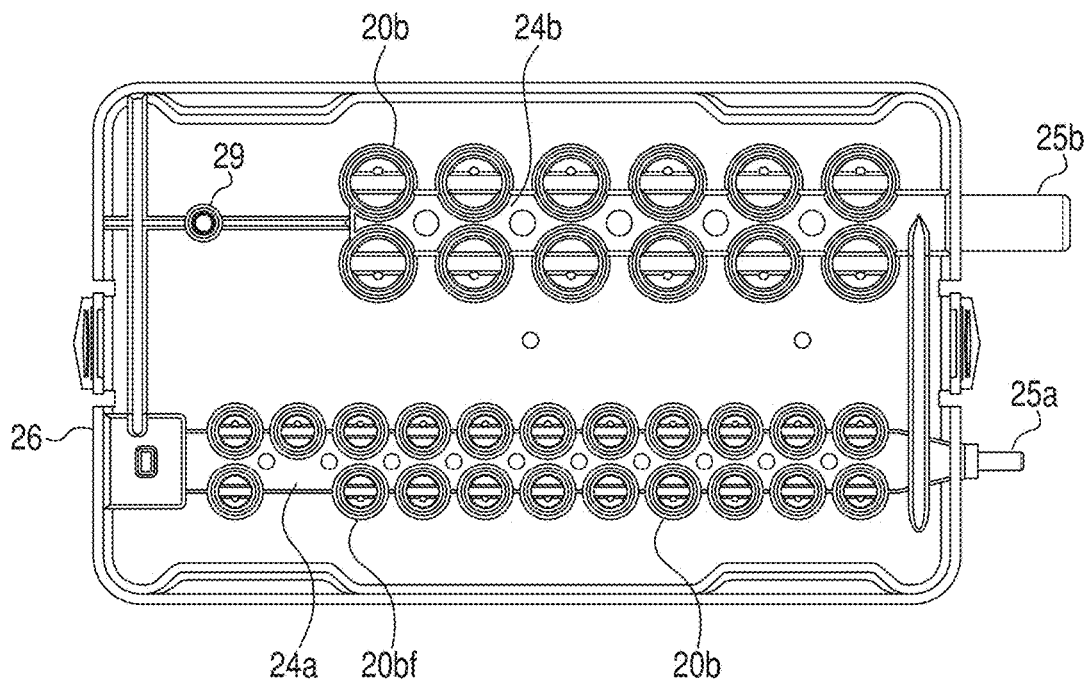
FIGS. 7A-C are a bottom, perspective exploded, and perspective assembled view, respectively, of the manifold of FIG. 1.
Figure 7B:
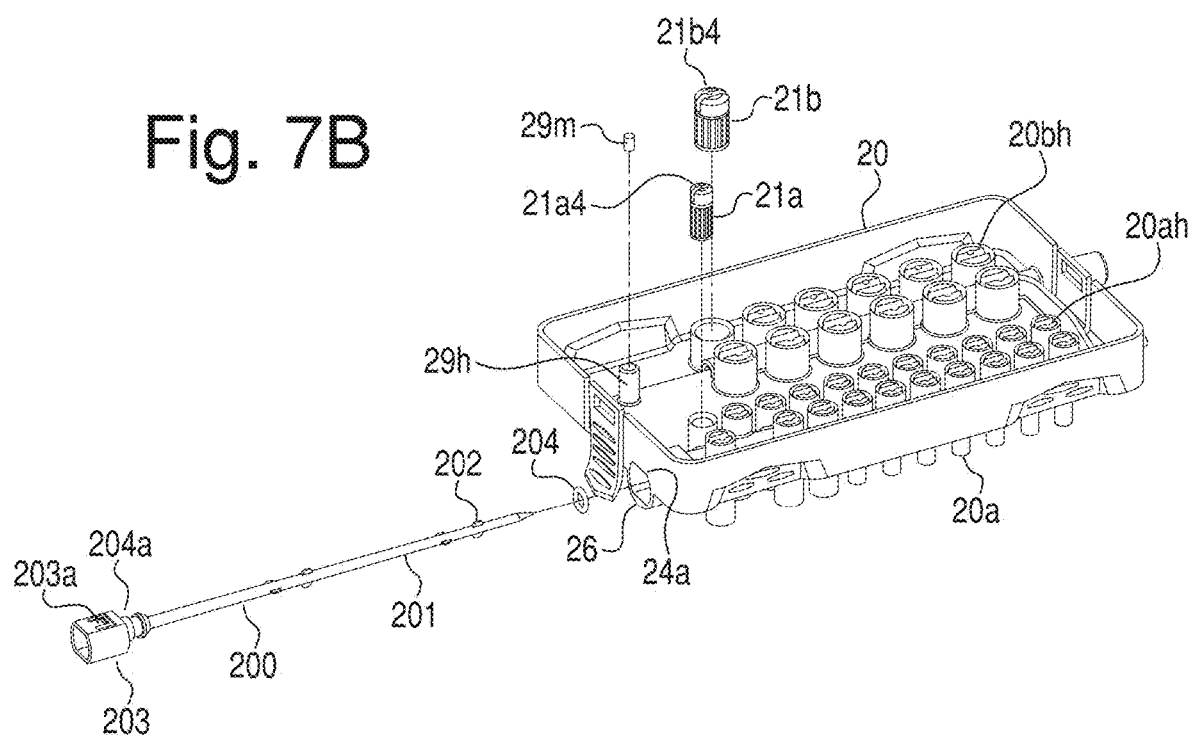
Figure 7C:
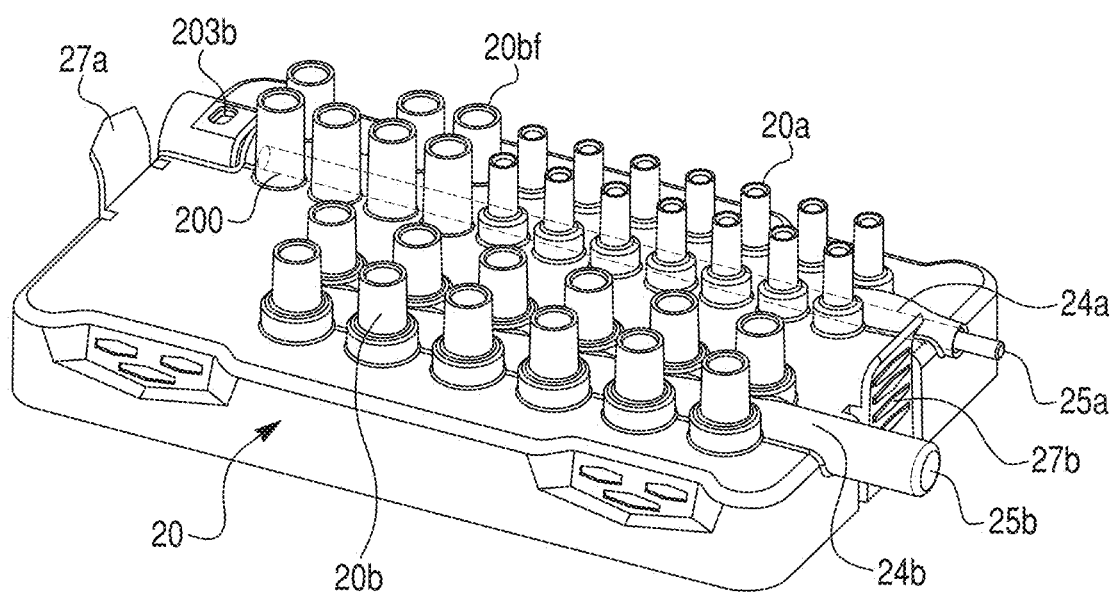

FIGS. 7A-C show a bottom view of the manifold 20, an exploded view, and an assembled view, respectively. The manifold 20 includes an array of macro ports 20b located in a linear fashion along either side of second channel 24b. The first channel 24a includes both flex ports 20b f and micro ports 20a located along the length thereof and provides fluid communication therebetween. Thus, the first channel 24a can be connected to both a macro flex line 2021 and a micro line 2011. In this embodiment, the flex line is configured as shown in FIG. 1 as a first macro line 2021 that is joined at a junction 2071 to two outgoing macro lines 2021 to allow fluid from macro container 4b to be supplied to both the first channel 24a and second channel 24b. In other words, a jumper branch connection in a macro line 2021 can be provided such that the macro line 2021 branches in two directions after leaving the macro storage container 4b, and can be connected to both the second channel 24b and the first channel 24a. The flex line conducts the same fluid/solution (e.g., nutritional ingredient) from container 4b to both channels 24a and 24b of the manifold 20 after passing through the valves 21b f and 21b, respectively. This facilitates the option of a singular or larger source container 4b being used for purposes of flushing/clearing the channels 24a and 24b as opposed to two separate containers 4b, wherein one container is connected to channel 24a and a separate other container is connected to channel 24b. A plurality of flex lines can be used since multiple types of flushing ingredients may be required during a compounding campaign depending on the varying clinical needs of the intended final contents of sequentially filled receiving containers (e.g. final bags 80). It should be noted that in this embodiment flex lines are terminated at flex ports 20bf (See FIG. 6B) farthest along the channels 24a and 24b from the outlets 25a and 25b, thereby allowing the entire channels 24a and 24b to be flushed with the flushing ingredient. In this embodiment, the micro line 2011 is not branched after leaving the micro storage container 4a, and therefore, there are no micro ports 20a that communicate with the second channel 24b. It is contemplated that an embodiment of the disclosed subject matter could include a manifold configured with valves adapted to allow micro lines to be attached to both the first and second channels 24a and 24b. Flex lines are designed to be used for any ingredient that may be requested across a wide range of volumes among different patient prescriptions. Hence, for some prescriptions where they are requested in small volumes, they can be delivered by the micro pump. Similarly, for prescriptions where they are requested in large volumes, they can be delivered by the macro pump. The y-connection fluid path of the flex line gives the ingredient access to both fluid paths (micro and macro) therefore the system can decide which pump to use to deliver that ingredient appropriately based on the requested volume.

In FIG. 7B, the valves 21a, 21b and filler 200 are disassembled to better show their relationship with the macro valve housing 20bh, micro valve housing 20ah, and first channel 24a in which each of these structures resides when assembled and ready for use. As can be seen, each of the valves 21a and 21b include a keyway 21a4 and 21b4, respectively, that allows for positive attachment to an actuator member 102a' and 102b' that extends from a manifold indent/surface 10c in the housing 10 of the compounding device.

The operational valve structures are in fact combinations of the rotating members (valves 21a and 21b) and the inner diameter (ID) of the socket in the manifold (20a h and 20bh) in which the valves 21a, 21b are located. The configuration of the operational valve structures was intended to create a more moldable elastomeric valve in which, under static fluid conditions, gravity based movement of fluids (like the motion caused by fluids of differing densities or different specific gravities settling or rising when the valve is left open) can be prevented or limited.

The actuator member is controlled by at least one stepper motor 102a, 102b such that rotation of the valves 21a and 21b can be precise. In one embodiment, the stepper motor 102a for the micro valves 21a can be of higher precision than the stepper motor 102b for the macro valves 21b (See FIG. 9). Higher precision stepper motors can be used to provide the positional accuracy of the micro valves 24a due to the inherent flexibility of the micro valves 24a. For example, a stepper that has a preset value of about 48 microsteps per revolution can be used (which preset value can be on the order of $10^3$ less than the microsteps per revolution value for the pump). Accuracy of the valves 21a, 21b (i.e., precise movement of the valves 21a, 21b) can be further controlled through the use of a tall gear box, which would result in large input rotations for the stepper motors 102a, 102b providing for small movement of each of the valves 21a, 21b, respectively. The flexibility of material that makes up each of the valves 21a, 21b can be configured or selected to enhance or provide improved sealing surfaces which withstand pressure differentials without leaking. Given this torsional flexibility and considering the friction opposing rotation of the micro valve 24a, it follows that during rotation, the upper features of the valve, i.e., those opposite the drive slots 24a4, angularly lag behind the lower features of the valve. Thus, in order to properly place the fluid opening between the valve 24a and the channel 21a, the higher precision stepper motors first rotate the valve 24a so that the top of the valve is properly positioned, and then reverse direction to bring the lower features also into proper position and therefore straightening the valve. The same action returns the valve to the closed position. The rotation of the steppers 102a and therefore the actuators 102a' and the valve 24a, can be clockwise, counter-clockwise, or any combination of these directions. Because, the micro valves 21a typically control the smaller volume ingredients, the volume should be measured and distributed with relatively higher accuracy as compared to that of the macro valves 21b, which typically distribute large volume ingredients in which high accuracy is easier to achieve. However, it should be understood that accuracy of delivery is not necessarily a direct function of valve operation. As long as the valves are properly opened and closed, the pumps 41, 42 can be used to provide accuracy of amount and control of fluid delivery.

In operation, the micro valves 21a and macro valves 21b can be described as being overdriven by the stepper motors past the 'open' position since the valves are flexible and the top of the valve lags behind the bottom of the valve when rotated. Thus, to properly open the valve, the bottom of the valve is overdriven from the target angular position. Once the top has achieved a proper location, the stepper reverses and brings the bottom of the valve into proper position. This operation effectively twists and then straightens the valve, and occurs in both the opening and closing process for the valves 21a, 21b.

Figure 9:
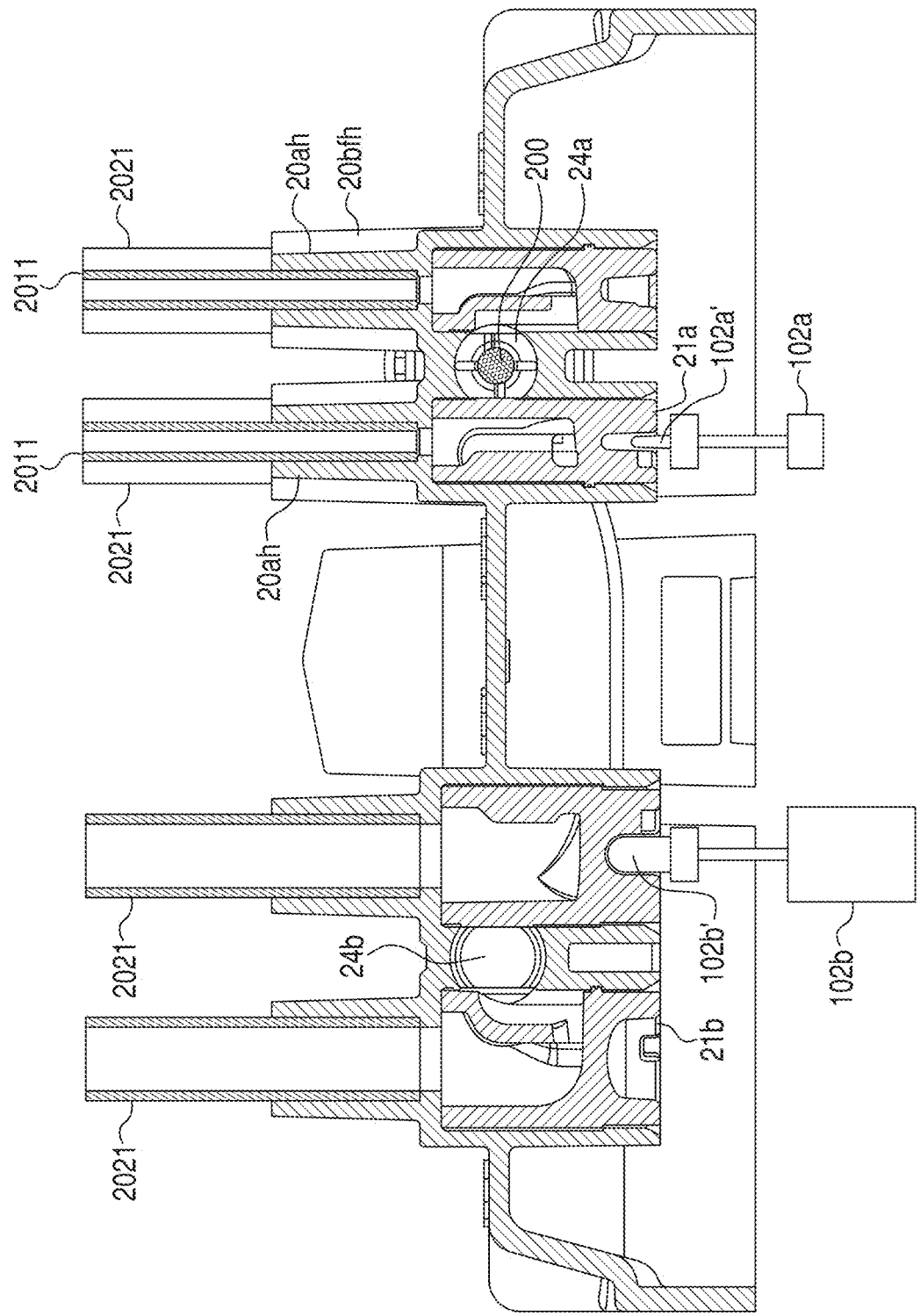
FIG. 9 is a cross-sectional view of two exemplary micro valves and two macro valves in open and closed positions and located in a valve housing in the manifold of FIG. 1.

FIGS. 7C and 9 show the valves 21a, 21b and filler 200 in place in the manifold 20. The filler 200 takes up volume within the first channel 24a such that the cross sectional area of the first channel 24a taken normal to a longitudinal axis of the channel 24a is smaller than the cross sectional area of the second channel 24b taken normal to a longitudinal axis of the channel 24b. Thus, the inner periphery of the first channel 24a and second channel 24b can be similarly shaped, allowing for certain architectural benefits in placement of the valves 21a, 21b and in fluid flow geometry of the channels 24a, 24b. The filler 200 can include a filler rod 201 that includes a plurality of spacers 202 located along the rod 201 so as to keep the rod 201 centered within the channel 24a. A clip lock 203 can be provided at a proximal location of the rod 201 and configured to lock with a mating clip lock indent in the manifold 20. In particular, a flexible tab 203a can be located on the lock 203 and configured to mate and lock with opening 203b in manifold 20 (See FIG. 7C). A sealing member 204, such as an O-ring 204, as shown in FIG. 7B, can seal the filler 200 in the socket 26 to prevent fluid such as air or liquids from leaking into or out of the channel 24a via the socket 26 when the filler 200 is located therein. The sealing member 204 can be located in an indent or receiving groove 204a on the rod 201 to lock the sealing member 204 in place with respect to the filler 200. One function of the filler 200 is to reduce common volume in channel 24a, which reduces priming volume and flushing volume. Because the micro pump only achieves limited flowrates, the large cross section of channel 24a without the filler would be difficult to be flushed of residuals.

Placement of the filler 200 in the channel 24a has the added benefit of increasing (or otherwise controlling and directing) turbulence within the channel 24a, and thus increases maximum fluid velocity within the channel 24a, permitting faster and more thorough flushing of residual fluids in the channel 24a to output 25a. The filler 200 can be conveniently loaded into the manifold via socket 26 during the time the manifold assembly 20 is being manufactured. The filler 200 geometry, particularly at the downstream end, is designed to promote flushing and to avoid areas where residual fluid can hide out and not flush properly.

Figure 8A:
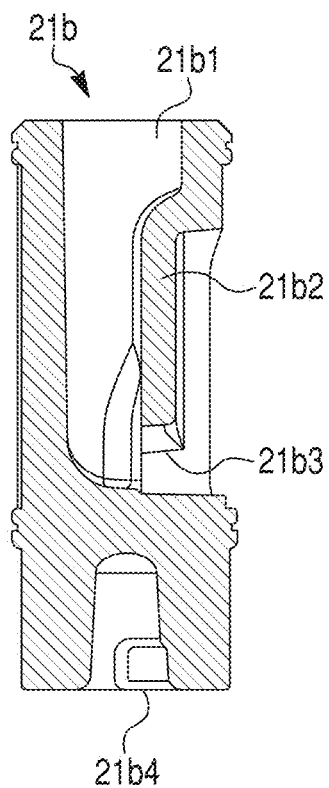
FIG. 8A is a cross-section taken along line 8A-8A of FIG. 8B.
Figure 8B:
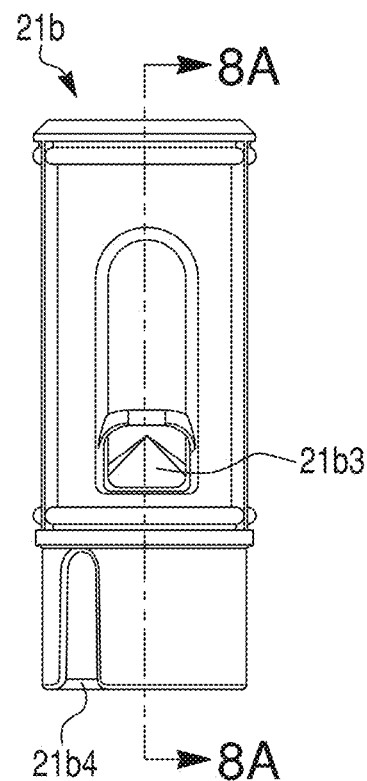
FIG. 8B is a side view of the valve shown in FIG. 7B.

Each of the micro and macro valves 21a and 21b can be configured as a rotational type valve that, when rotated a set amount, permits a corresponding or known amount of fluid to bypass the valve. In one embodiment, the valves 21a, 21b can be configured such that rotation of each of the valves does not move fluid, and only opens/closes a fluid path. The amount of fluid that bypasses the valve can, however, be ultimately determined by the pump speed, size and in conjunction with the tubing size when using a peristaltic pump. The valves can be configured to simply open or close the fluid lines. FIG. 8A shows a macro valve 21b that includes an inlet 21b1 at a top of the structure and an outlet 21b3 at a side wall of the structure. Thus, fluid enters the top of the valve 21b along a rotational axis of the valve 21b, and exits a side of the valve 21b in a direction substantially normal to the rotational axis of the valve 21b. Rotation of the valve 21b is accomplished by connection to a stepper motor 102b via actuator connection slot 21b4 located in a bottom surface of the valve 21b. The slot 21b4 acts as a keyway for a corresponding projection 102b' extending from the top of the stepper motor 102b. When the stepper motor 102b turns the projection 102b' a preset amount, the valve 21b is also caused to turn the same amount due to the connection between the projection 102b' and the keyway or slot 21b4. When the valve 21b is located in an open position or a semi open position, fluid can travel from the inlet 21b1 down through a center of the valve 21b until it passes wall 21b2, which can be configured as a gravity wall, or P-Trap, or similar structure. After passing the wall 21b2, the fluid then changes directions by approximately 180 degrees and moves up and over the outlet wall in the manifold 20 to be distributed into the second channel 24b. The wall 21b2 and geometry and configuration of surrounding manifold walls prevents fluid from inadvertent and uncontrolled mixing between lines 2011/2021 and the common volume of channel 24a on the micro side and between lines 2011 and the common volume of channel 24b on the macro side when 1) the valve is open, 2) the fluid is static (i.e., pump rotors 41 and 42 are not moving), and 3) there exists a differential in specific gravity between the respective fluids in the input lines and in the channels. The motivator for this backflow is specific gravity differences between the ingredient fluid and the fluid in the channel. This wall 21b2 is a technical feature of the valve that mechanically prevents this backflow from occurring without additional control mitigations, and requires no additional software/valve controls to limit the effect of this backflow tendency because the wall structure physically stops or prevents backflow from happening. Thus, the walls 21b2 and surrounding geometry of the valve housing 21bh prevents contamination of the ingredients in the supply lines and storage containers 4b and prevents uncontrollable flow/mixing into the channels 24a and 24b of the manifold 20 due to, for example, differences in specific gravity of the solutions or fluids running through the valves. The output of the micro and macro valves 21a, 21b (with respect to each respective opening into the common channels 24a, 24b located in manifold 20, shown in FIG. 9) is above the above-described "P-trap" thus not allowing flow that might otherwise enter into the manifold 20 due to specific gravity differences. Thus, the valves 21a, 21b work with the structure of the manifold 20 in this embodiment to form the specific gravity "P-trap" structures.

Although FIGS. 8A and B show a macro valve 21b, the micro valve 21a can be configured and will operate in the same manner, albeit using smaller dimensions.

The two motors that drive each of the rotors 41, 42 can be the same, and similarly the rotors 41, 42 can be identical. The tubing in each channel can be different, and the platen positions can be different because of the difference in the diameter and wall thickness of the tube sections.

Figure 10:
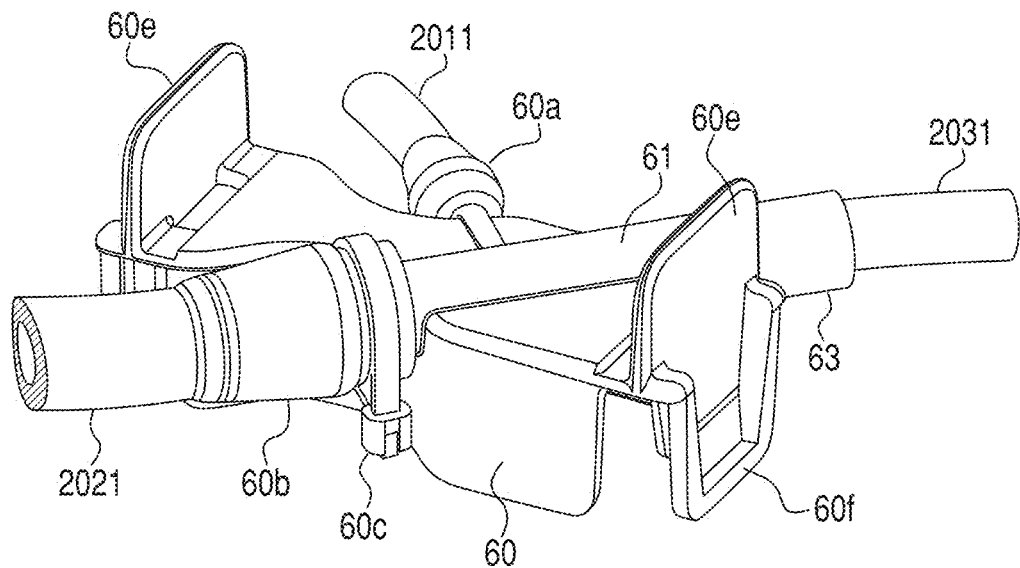
FIG. 10 is a top perspective view of an exemplary union junction.

FIG. 10 shows a perspective view of the union junction 60. The union junction 60 is configured to retain and/or receive a tubing structure that includes a micro input line inlet port 60a, a macro input line inlet port 60b, a union junction line 61 and an outlet port 63. The micro input line inlet port 60a is configured to receive the micro line 2011 which carries fluid from the micro channel, which can include fluid from one or both the micro fluid containers and macro fluid containers that were described earlier. The macro input line inlet port 60b is configured to receive the macro line 2021 that carries fluid from the macro fluid containers that were described earlier. The micro input line inlet port 60a and the macro input line inlet port 60b are both coupled to a junction line 61. Thus, fluid flowing from the micro line 2011 enters the micro input line inlet port 60a and flows through the junction line 61 and is combined with fluid received by the junction line 61 from the macro line 2021 via the macro line inlet port 60b. In this manner, fluid from micro line 2011 is combined with fluid from the macro line 2021 for delivery to the receiving/final container (e.g., IV bag 80). FIG. 10 also shows macro input line tie down 60c that maintains the macro input line inlet port 60b in place. A similar tie down 60c can be used to secure or maintain the micro input line inlet port 60a in place. The junction line 61 includes an outlet port 63 coupled to a output line 2031. As fluids from the micro line 2011 and the macro line 2021 combine in the junction line 61, they flow through the outlet port 63 to the output line 2031. The fluid flows from the output line 2031 to the final container or receiving bag filling station, which is described in greater detail below. FIG. 10 also shows that the union junction 60 includes handles 60e that can be used for the placement and removal of the union junction 60 onto mating receptacles on the housing 10. Locks, such as flexible spring locks 60f, can mate with receptacles on the housing 10 to further secure the junction 60 thereto.

Figure 11:
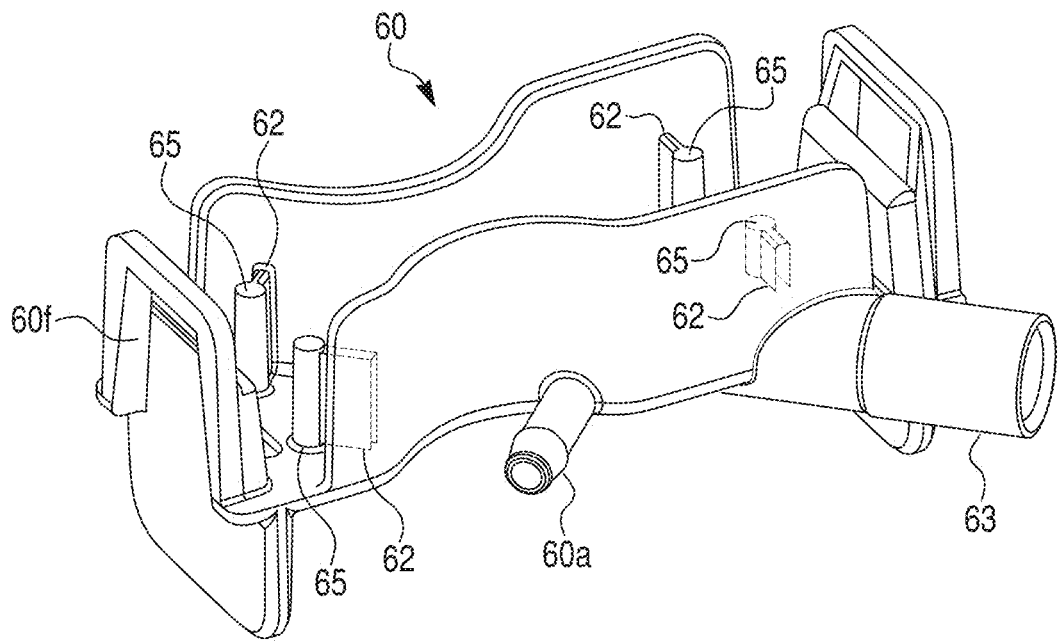
FIG. 11 is a bottom perspective view of the exemplary union junction of FIG. 10.

FIG. 11 shows a bottom side perspective view of the union junction 60. FIG. 11 shows that the union junction 60 includes a plurality of standoff ribs 62 and pin bosses 65 which are spaced apart from each other along an interior surface of the union junction 60. The standoff ribs 62 and pin bosses 65 are configured to provide an insertion spacing stop to retain the junction 60 at a predetermined distance/height relative to the housing surface. The standoff ribs 62 and pin bosses 65 can also provide structural integrity for the tubing structures described above, including the micro input line inlet port 60a, the macro input line inlet port 60b, the junction line 61 and the outlet port 63 so that those structures are maintained in place even as fluids are passed therethrough.

Figure 12:
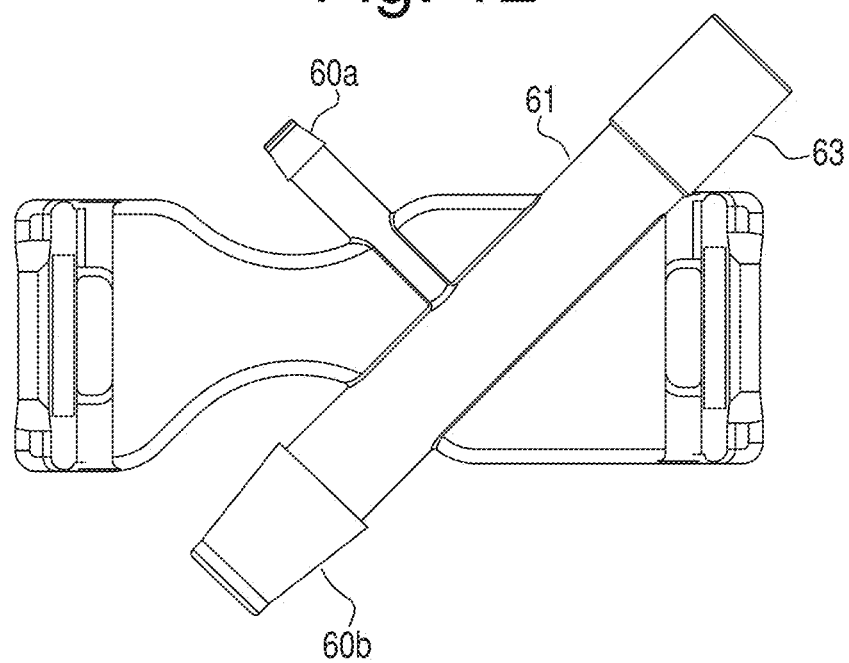
FIG. 12 is a top view of the exemplary union junction of FIG. 10.

FIG. 12 shows a top view of the union junction 60 with the tubing structures described above in place. As can be seen in FIG. 12, the union junction line 61 receives fluid via the micro input line inlet port 60a and the macro input line inlet port 60b. The fluids mix in the union junction line 61 and are carried to the outlet port 63 for eventual delivery to the receiving bag 80. As shown in the FIG. 12 and in this exemplary embodiment, the micro input line inlet port 60a joins the union junction line 61 in a direction perpendicular to a longitudinal direction of the union junction line 61, while the macro input line inlet port 60b causes fluid to flow into the union junction line 61 in the same direction as the longitudinal axis of the union junction line 61. In alternative embodiments, the micro input line inlet port 60a can join the union junction line 61 at any angle relative to the longitudinal direction of the union junction line 61 so as to optimize usability of loading onto the platform 10d and notch 18 and simultaneously ensure proper contact with pump rotors 41, 42 and optimize flushability of the union junction 61.

The tubing structure described above, including the micro line inlet port 60a, the macro line inlet port 60b, the union junction line 61 and the outlet port 63 can be formed, e.g., molded, into the union junction 60 so as to form a unitary structure. Alternately, the tubing structure can be formed as a separate unit that can be placed or snapped into the union junction 60 and retained in place using a mechanism such as the standoff ribs 62 and pin bosses 65 described above. In addition, it should be understood that the compounding system 1 can be configured without the presence of a union junction 60 as shown. Instead, the union structure can be the final container, such as the receiving bag 80 itself. For example, lines 2011 and 2021 can extend about rotors 41, 42 and continue all the way to two separate ports in the receiving bag 80 such that mixing of materials from lines 2011 and 2021 occurs only at the receiving bag 80. In this case, it may be beneficial, depending on the particular operating parameters, to secure lines 2011 and 2021 at locations downstream of the rotors 41, 42 to ensure proper and efficient operation of the pump 40.

Figure 13:
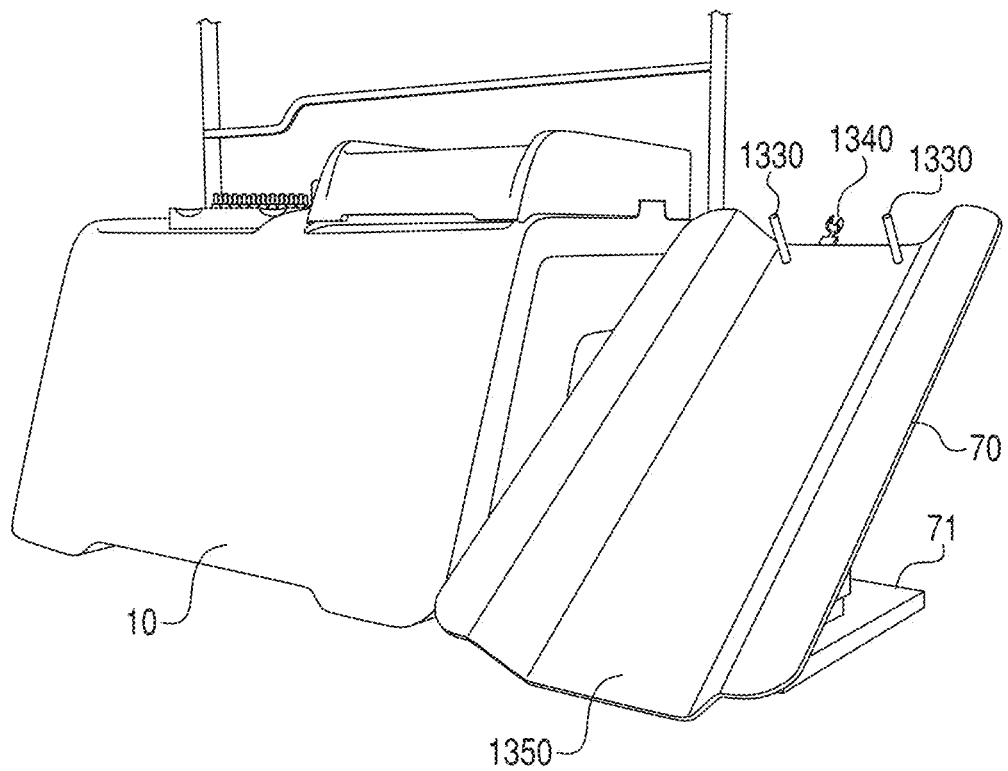
FIG. 13 is a partial perspective view of a compounding system made in accordance with principles of the presently disclosed subject matter.

FIG. 13 shows perspective view of the compounding system 1 in accordance with an exemplary embodiment. FIG. 13 shows housing 10 located adjacent a bag tray 70 for holding a receiving bag 80 during the filling process. A load cell 71 or other device, such as an analytical balance, can be integrated into the bag tray 70 to provide information relative to the weight and contents and to facilitate calibration as well as confirmation of operational functions for the compounding system 1. Protective devices and/or software can be incorporated into the device to protect the load cell 71 or other measuring device from damage due to accidental overload or other mishaps. As shown in FIG. 13, the bag tray 70 includes a bag tray receiving section 1350 that accommodates the shape of the receiving bag 80. The bag receiving section 1350 can be formed as a generally indented surface within the surface of the bag tray 70. The bag tray 70 also includes bag tray pins 1330 which are formed on an upper section of the bag tray 70. As shown in FIG. 13, the bag tray pins 1330 are formed perpendicular to the surface of the bag tray 70 so as to project in a direction away from the top surface of the bag tray 70. The bag tray pins 1330 are positioned to receive and hold a receiving bag 80 for filling. FIG. 13 also shows a bag tray clip 1340 that is formed along an upper section of the bag tray 70. The bag tray clip 1340 can be configured to keep a known tubing artifact constant with respect to the output fluid line(s) 2031 connected to the receiving bag 80 (i.e., can be configured to dampen vibration or other force transmission to the bag 80 and/or load cell 71). Depending on how the bag 80 is connected to the outlet of the transfer set, and how the tube is positioned, variances can occur. The clip 1340 prevents these variances.

Figure 14A:
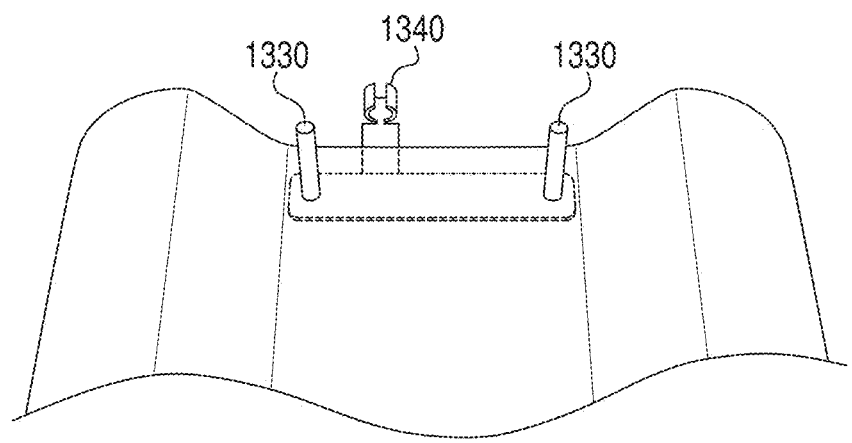
FIGS. 14A and 14B are partial perspective views of the bag tray and receiving bag.
Figure 14B:
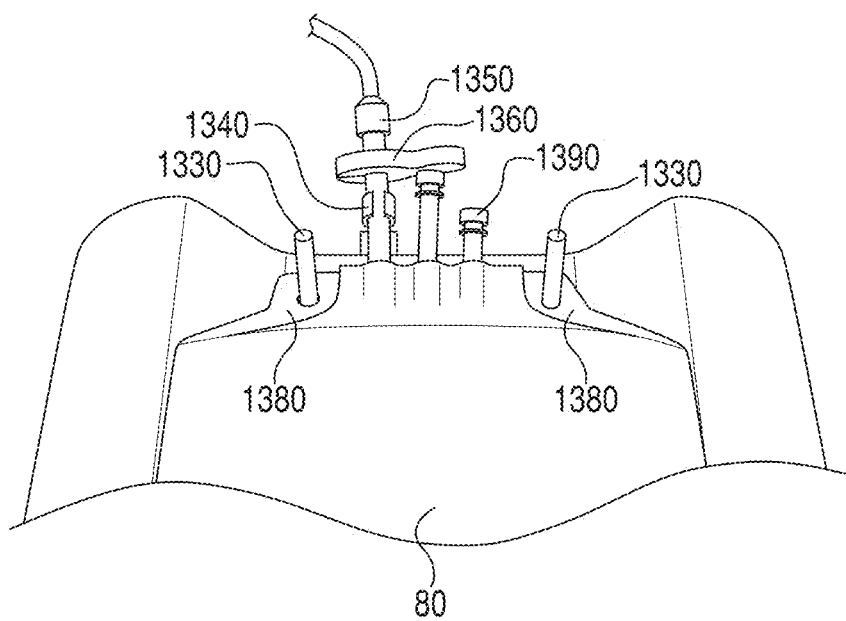

FIG. 14a shows a close up view the upper section of the bag tray 70 illustrating the placement of the bag tray pins 1330 that are positioned to receive and retain a receiving bag 80 for filling. FIG. 14a also shows the bag tray clip 1340 that is provided to secure the container input tubing, which includes the output line 2031. FIG. 14b shows a close up view of the upper section of the bag tray 70 including a receiving bag 80 placed in the bag tray 70. The exemplary receiving bag 80 includes two openings 1380 for receiving the bag tray pins 1330. Thus, when the bag tray pins 1330 are placed through respective openings 1380 of the receiving bag 80, the receiving bag 80 is maintained in place for filling. FIG. 14b also shows a twist lock 1350 formed on the end of the output line 2031. The twist lock 1350 is configured to connect to and lock with a port 1360 formed on a top surface of the receiving bag 80. The twist lock 1350 allows the output line 2031 to be securely coupled to the receiving bag 80 so that the receiving bag 80 can be filled. The bag tray clip 1340 can be configured to securely retain the port 1360 and twist lock 1350 that allows for quick placement, filling and removal of the receiving bag 80. The clip 1340 also secures the tubing to the bag tray to prevent unwanted artifacts in the load cell 71 measurement that could occur from excessive motion of the tubing segment that spans the gap between the bag tray and the pump module. This tubing motion could be caused by user interaction or pump vibration during compounding. Manual port 1390 can be provided at the top of the receiving bag 80 such that a user can inject an ingredient that is either not included in the compounding system 1 or has run out and is required to complete the receiving bag 80.

In similar fashion to the description above, a dual chamber bag may be filled using a slightly modified workflow, wherein the dual chamber bag keeps incompatible ingredients separate by two physical separated chambers that are kept separate from each other during compounding, but are combined just before infusion of the patient is started. All of the steps described above are followed for the 'primary' side of the receiving bag. Once complete on the primary side, the primary side port 1360a is disconnected from the twist lock 1350. The secondary bag port 1360b can then be connected to the twist lock 1350 and the secondary chamber thus filled.

Figure 15:
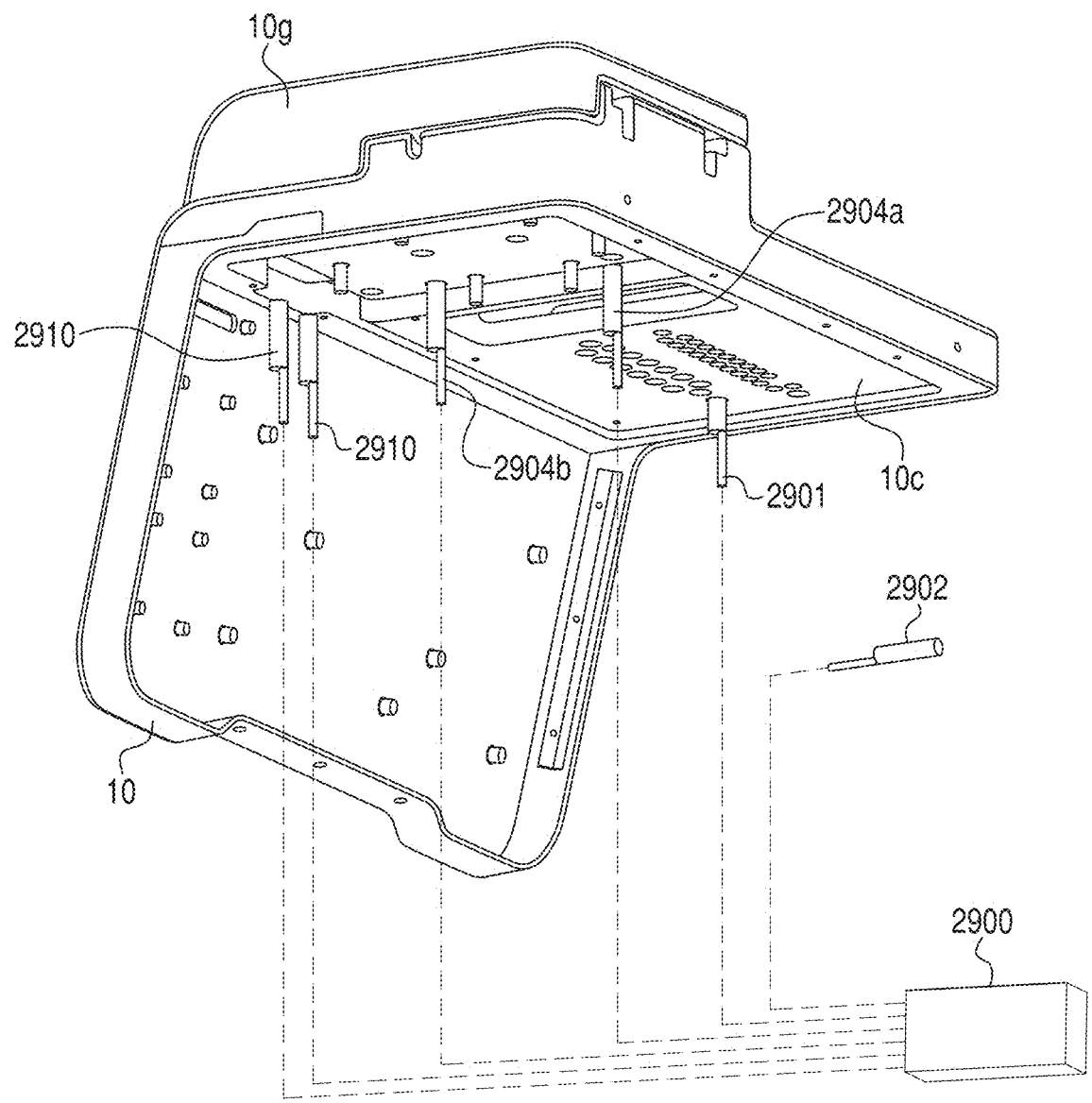
FIG. 15 is a right rear corner perspective view of a front/top panel and sensor array for the compounding system of FIG. 1.

FIG. 15 is a rear partial perspective view of the compounding system 1 that shows an exemplary sensor array used in conjunction with the system. Sensors 2910 can be configured to sense when the covers 10f and/or 10g are in place (See FIG. 3A). Alternatively, a reed switch sensor can be built into the combination sensor assembly to provide confirmation that 10f is closed. Sensors 2910 can be magnetic, such that they serve two purposes: 1) communication to a controller 2900 information indicating that the covers 10f and/or 10g are in a closed/operational position; and 2) securing, via magnetic force, the covers 10f and/or 10g in place in the closed/operational position. It should be understood that the sensors themselves may not provide enough force to provide a hold down function. Instead, a ferrous catch plate and lid magnet can be used in conjunction with the magnetic sensor. Sensors 2904a and 2904b can be configured to communicate to the controller 2900 that the platen locks 44a and 44b, respectively, are in a closed/operational position. Sensor 2901 can be provided in housing 10 and configured to communicate with the controller 2900 information that indicates that the manifold 20 has been properly affixed to the housing 10 and is ready for operation.

Sensor 2902 can be located adjacent a rear surface of the housing 10 and configured to communicate with the controller 2900 information that places the compounding system 1 in a service or firmware/programming mode when a maintenance operator or technician activates this sensor (for example, by placing a magnet adjacent the sensor 2902). The location of the sensor 2902 may be known only to service and technical maintenance personnel.

The exemplary compounding system 1 can also include a compounding control manager that resides in a central processing unit (e.g., controller 2900). The compounding control manager allows a clinician or other healthcare or compounding professional to enter, view, adjust and offload information pertaining to a given compounding protocol. In general, the compounding control manager is the program language that provides the operator with real time feedback and interaction with the compounding device through graphical user interface (GUI) elements. The GUI elements, created in a graphical format, display the various inputs and outputs generated by the compounding control manager and allow the user to input and adjust the information used by the compounding control manager to operate the compounding device. To develop the GUI elements, the compounding control manager can utilize certain third party, off-the-shelf components and tools. Once developed, the compounding control manager can reside as a standard software program on a memory device.

The controller 2900 can include firmware that provides several adjustment algorithms or hardware solutions to control the accuracy of the pump 40. For example, the pump output can be corrected for degradation of the pump tubing lines 2011, 2021 over the life of the transfer set or manifold 20. This adjustment is applied as a function of the number of pump rotations experienced by each tubing line. The controller 2900 can also include software or hardware such that pump output or "flow factor" can also be adjusted for the specific fluid being pumped. This "flow factor" can account for fluid viscosity, pump speed, line type, and source container/spike type. The controller 2900 can also be configured to correct pump output for the rotational location of the pump rotor 41, 42 rollers relative to the platens 43a, 43b. This adjustment can be significant for small volumes that are dispensed and which represent only a few rotations of the pump head or less. Note that absolute encoders can be included on both pump motors 41s, 42s (and valve steppers) to provide the firmware (e.g., controller 2900) with the information necessary to make the above-noted adjustment(s). The controller 2900 can include a bubble detection algorithm that attempts to minimize nuisance alarms. The system may include two bubble detectors for each channel so that the two measurements can be compared to determine whether there is a sensor failure.

Figure 19:
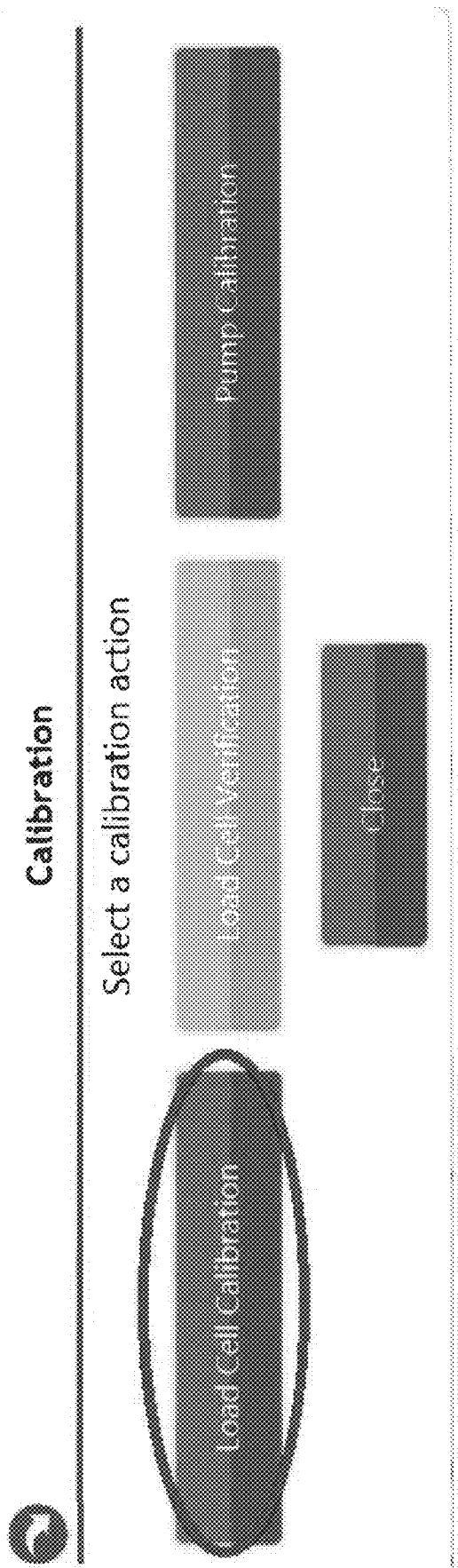

FIGS. 16-34 are a walk-through of display screens generated by a representative embodiment of the compounding control manager, which demonstrate various features of the compounding control manager, and FIG. 36 is a flow chart of an exemplary process that may be used to setup and manually prepare the system of FIG. 1 in accordance with the principles of the disclosed subject matter. The process initiates with the operator activating the compounding manager (step 3602 in FIG. 36). After an initial start-up mode of software initialization, a main work area is created on a display device, which initially opens a log-in screen. The operator first identifies him or herself, either by using the bar code scanner to scan an operator badge number and/or barcode, or by entry of a badge number or other selected form of identification on the graphical touch screen entry pad (step 3604 in FIG. 36). Thus, in step 3604, the operator has input or scanned his or her user credentials into the compounding manager. This identification procedure is required for logging-in and/or assessing the operator's level of security clearance. Desirably, a system administrator would have previously established a list of authorized users, against which the sign-in data is compared. At this point, the operator can be presented with a checklist of items to be performed before proceeding. These checklist items can be user programmable and may include, for example, a prompt to confirm that the compounding device has been cleaned (step 3606 in FIG. 36). The operator will then be prompted to initiate a process so that the load cell is calibrated (step 3608 in FIG. 36). The user can initiate calibration of the load cell 71 by selecting the "load cell calibration" button shown in FIG. 19. FIG. 20 shows a further interface that is presented to the user to ensure that the load cell 71 is properly calibrated. When the calibration is completed, the user can then select the "close" button.

Figure 16:
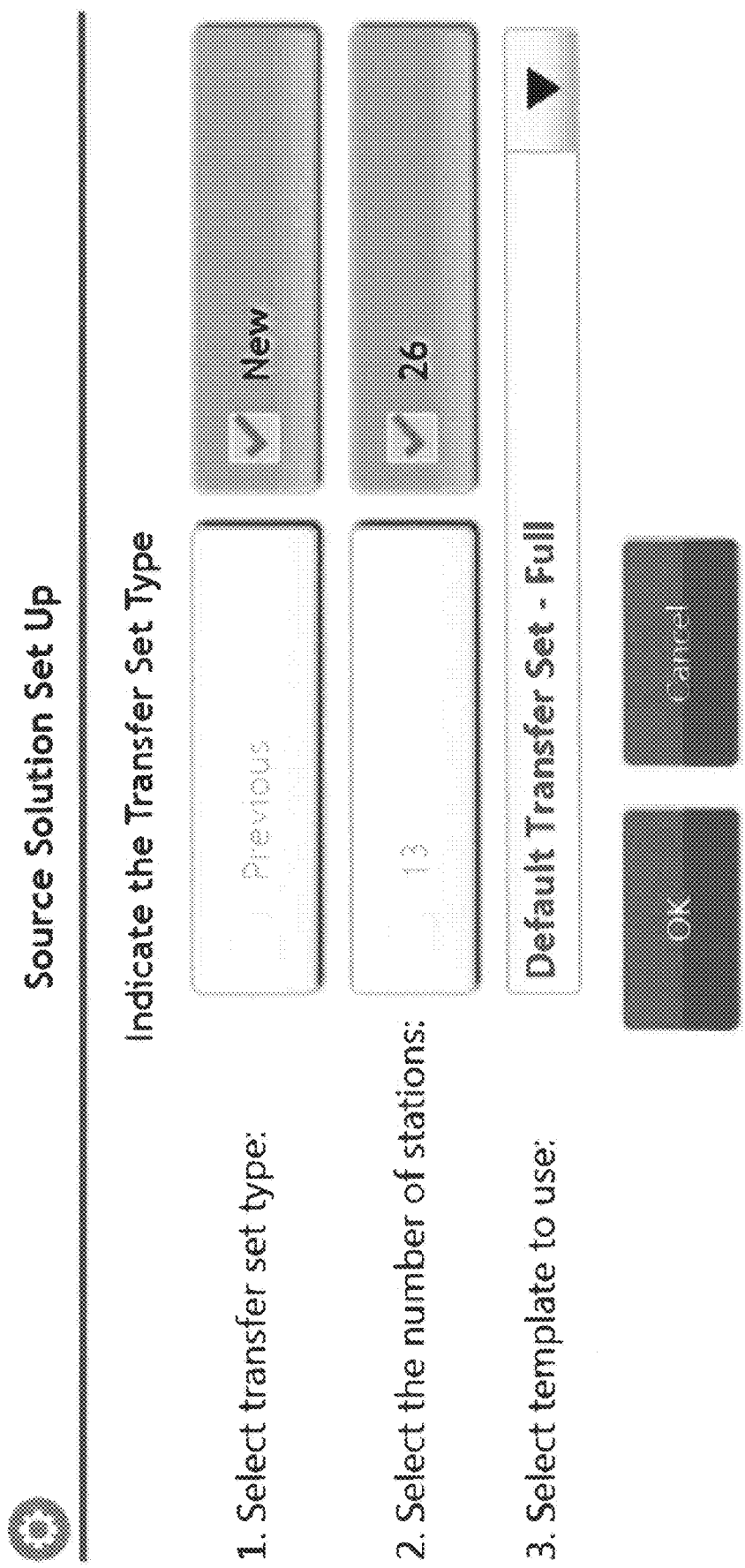
Figure 17:
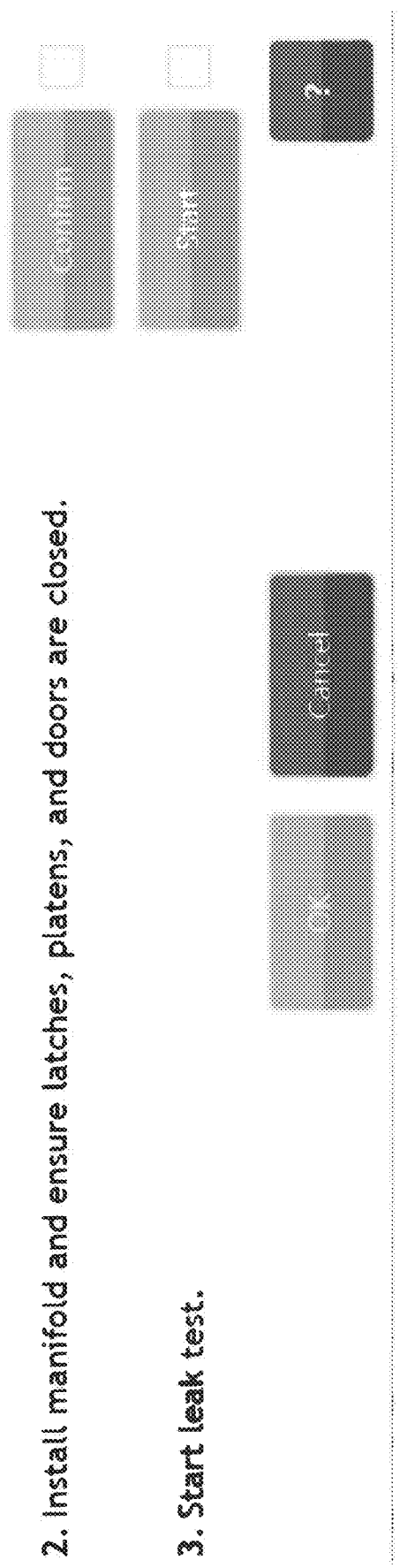
Figure 18:
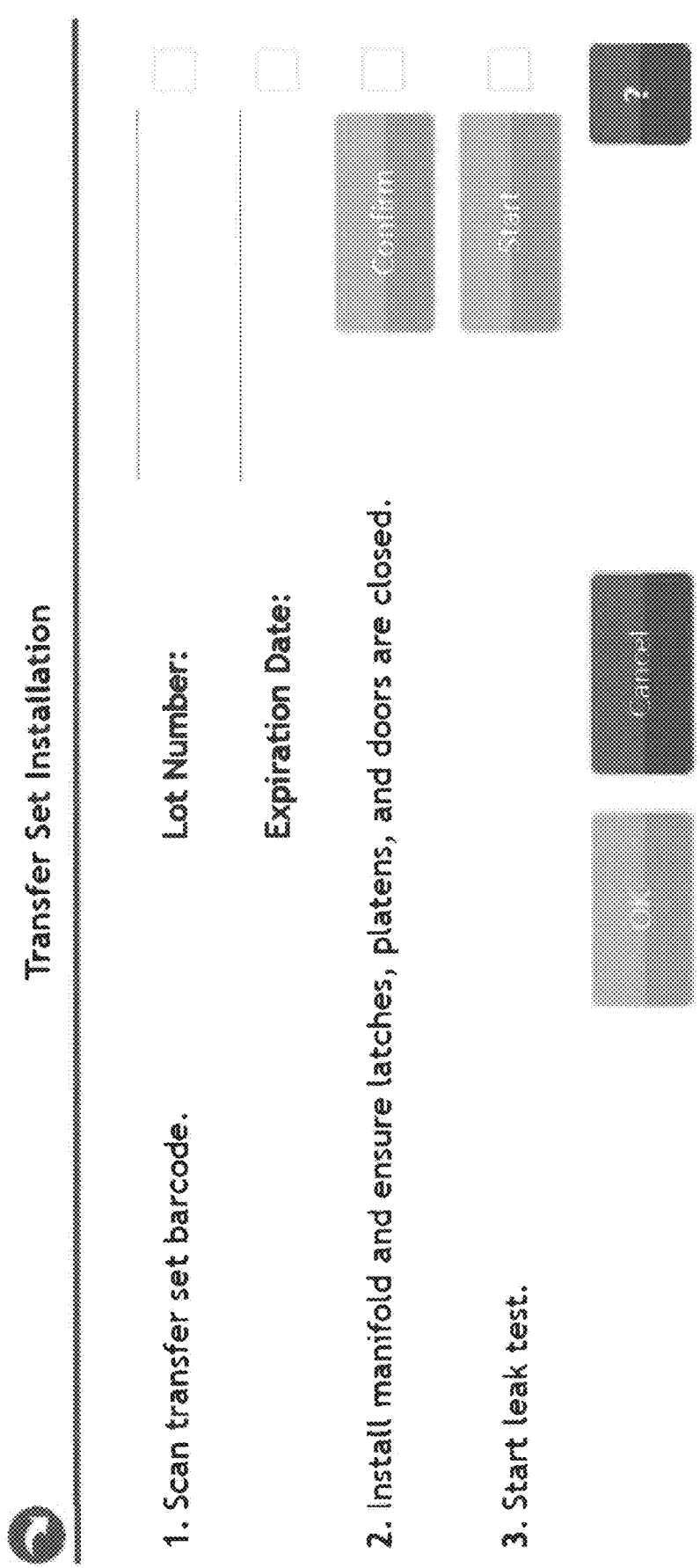

FIG. 16 depicts an interface that may be presented to a user after the user has logged in and been authenticated as an authorized user. FIG. 16 is a control panel that allows the user to indicate the type of transfer set to be used (step 3610 in FIG. 36). At this point, the operator may be prompted that the transfer set is ready to be installed and that a leak test should be performed (step 3612 in FIG. 36). In this step, a new transfer set. Thus, the fluid lines are capped and the transfer set is installed. The step of performing a leak test may include occlusion and bubble sensors that check for leakage in the tubing (for example, through the detection of an air leak). FIG. 17 shows an interface that the operator may be presented with to execute step 3612. The interface of FIG. 17 allows the user to scan a bar code located on a lid of a tray in which the transfer set 2 is provided. In this manner, the system knows the transfer set 2 that the user has chosen. The user can then remove the transfer set 2 from the packaging and install it. The process of installing the transfer set 2 includes opening the device doors and platens, placing and snapping the transfer set manifold 20 to the top of valve actuators 102a', 102b' and platform 10c and draping the leads of the transfer set over a rack that is disposed in the laminar flow hood. After the user snaps down the manifold 20 onto the device, the user may then route the tubing through a bubble and occlusion sensor followed by closing the sensor lid. Next, the user can route the tubing around the pump rotors and secure union junction to the pump module. Each of the rotors can include a bottom flange or guide member that is configured to prevent the tubing from being installed too low or slipping or being pinched between the pump surface and the rotor. Finally, the user can close the platen locks and then close the pump door or cover.

Figure 21:
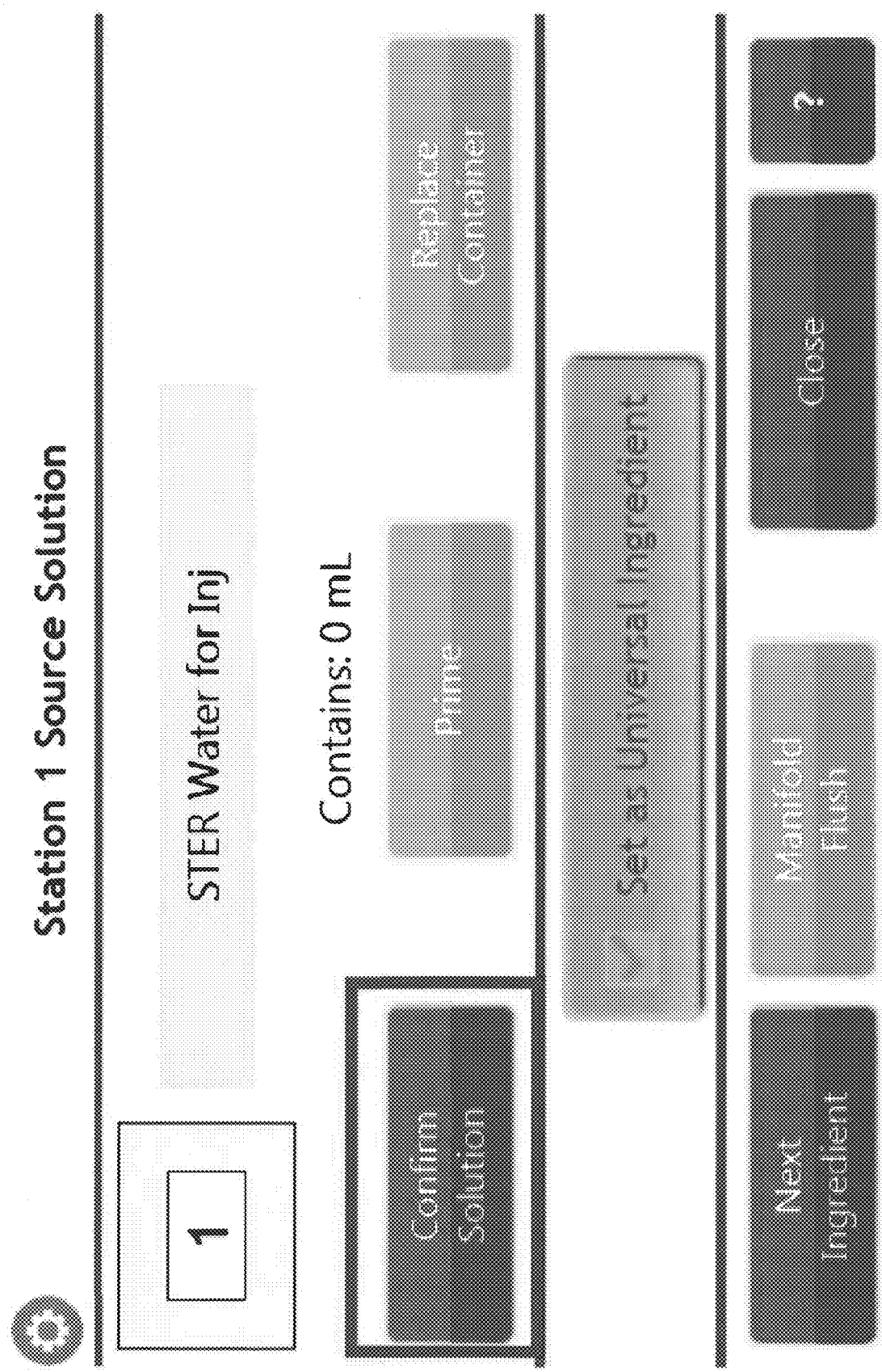
Figure 22:
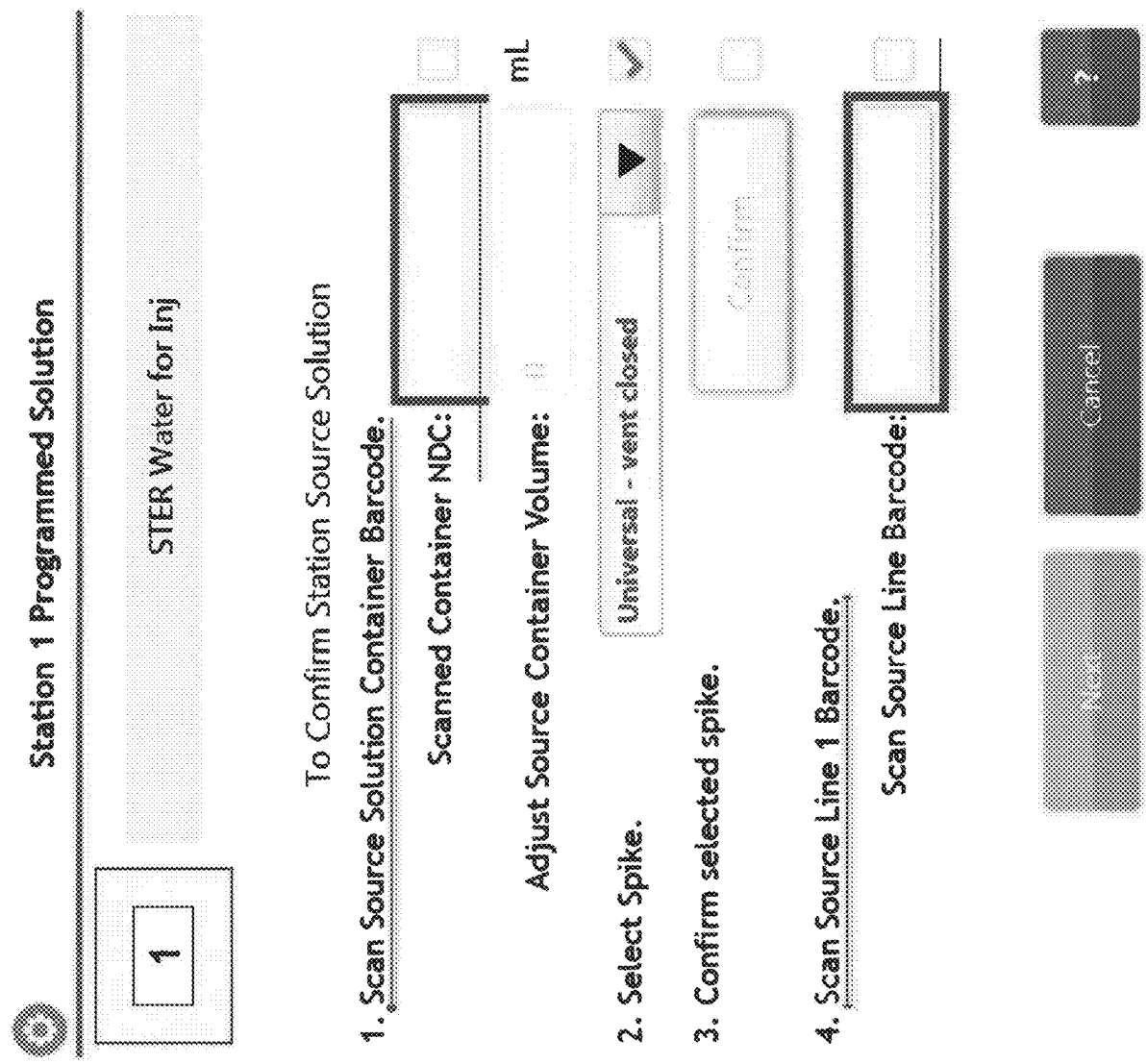
Figure 24:
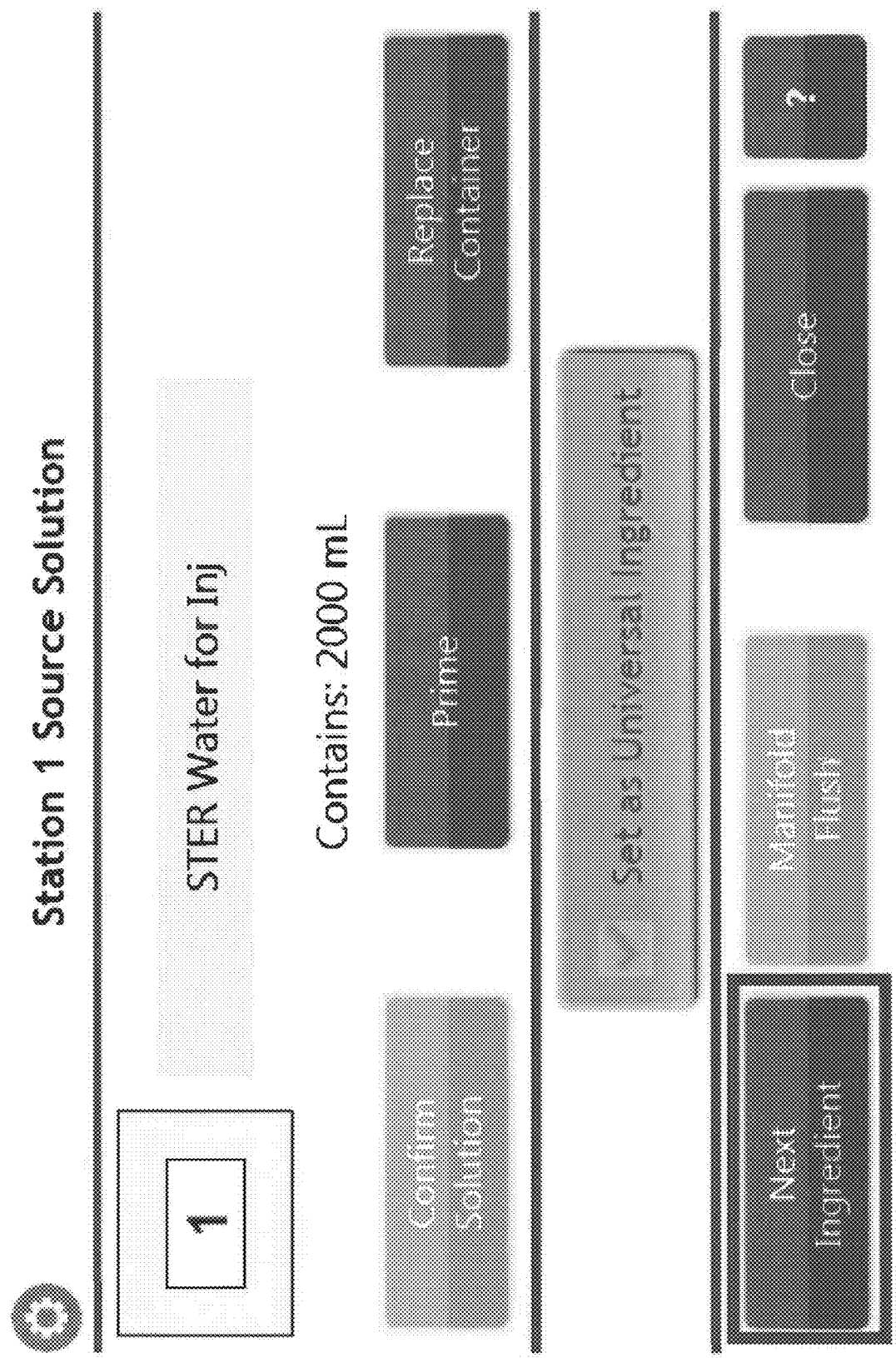
Figure 26:
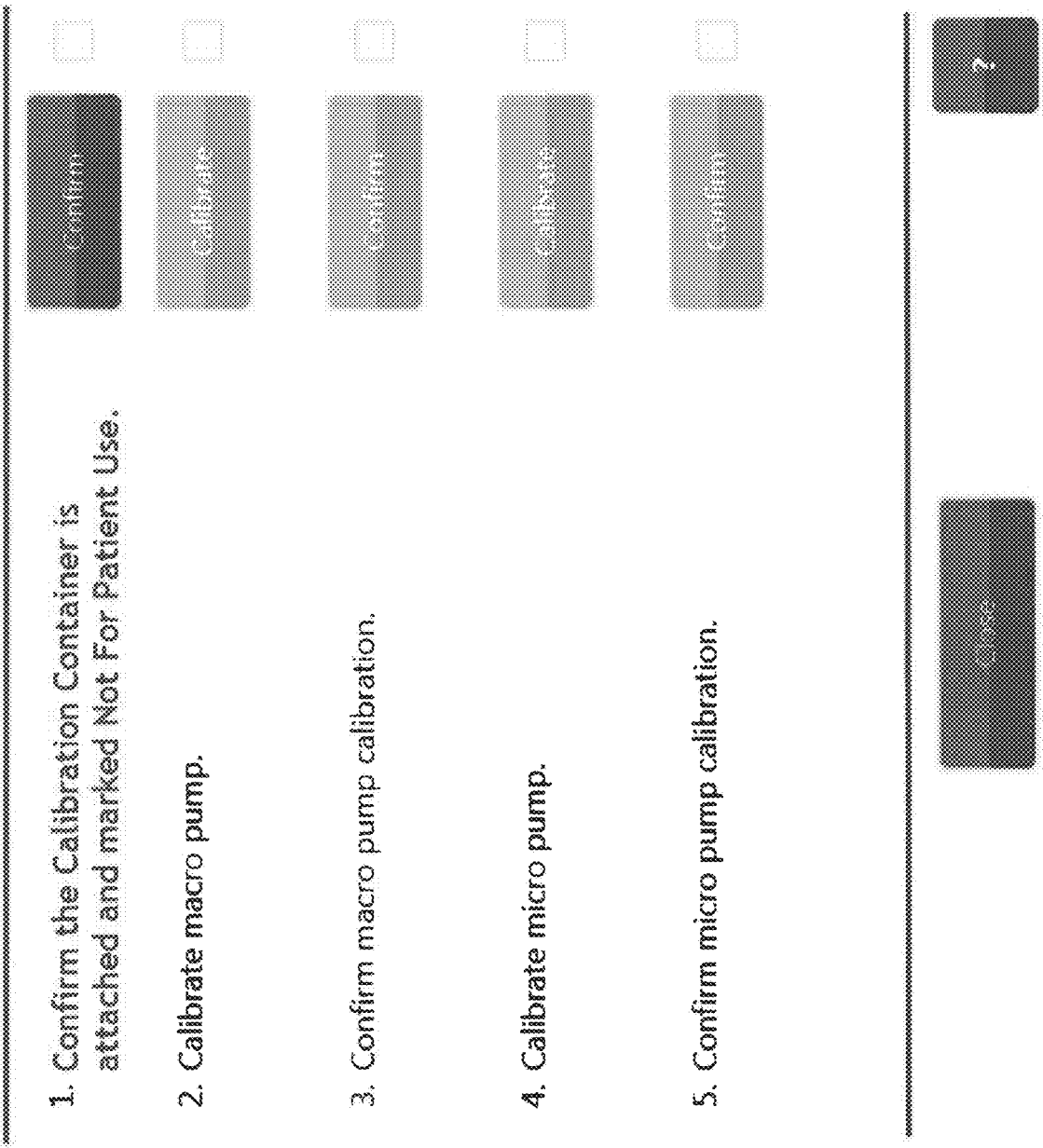
Figure 28:
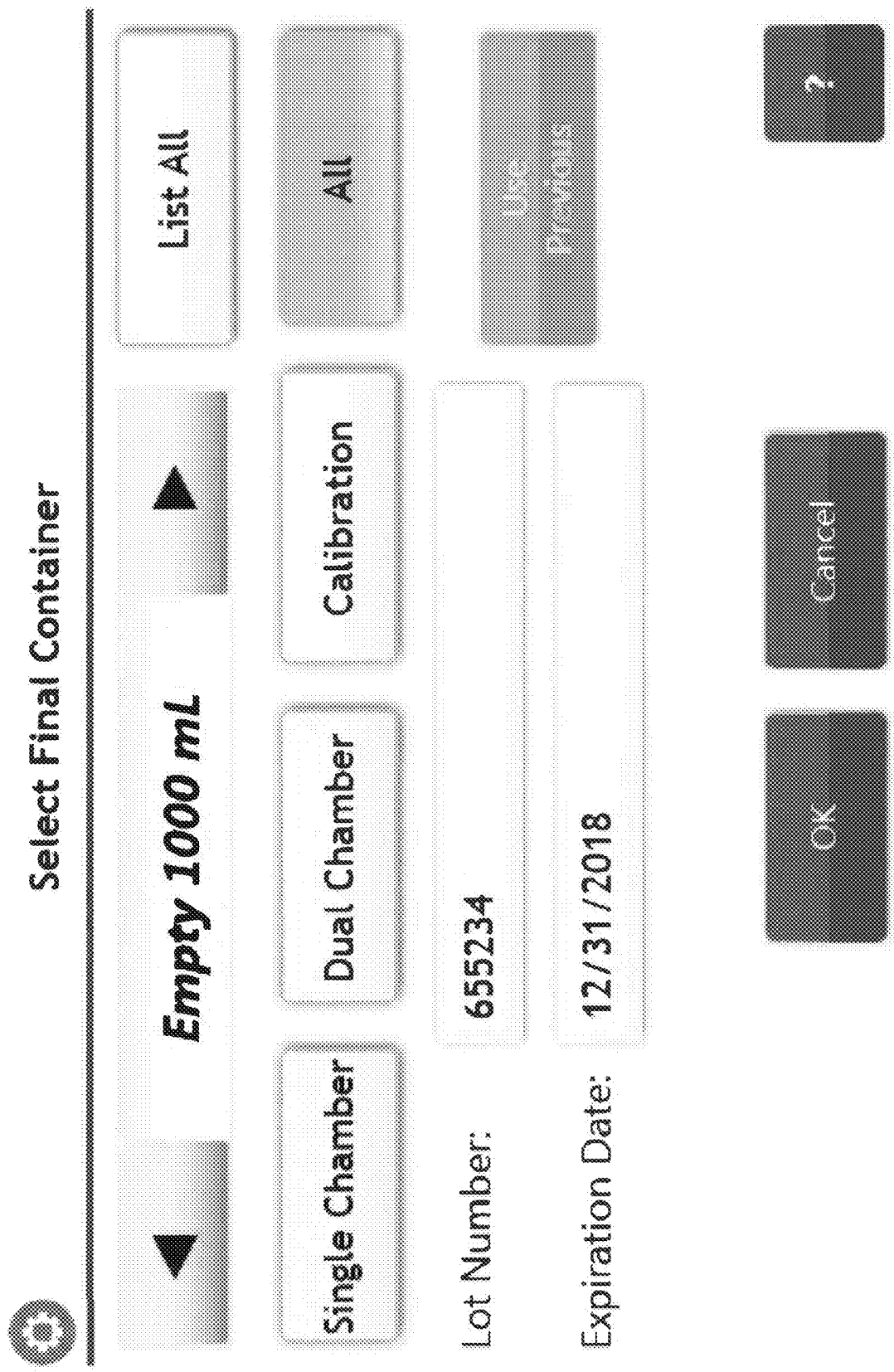

In the next step, the operator can select and confirm the fluid input stations to be used. This step can include, for example, selecting which ingredients/compounds are assigned to each fluid line (step 3614 in FIG. 36). FIG. 21 shows an interface that is presented to the user for confirming the source solutions. The user can select the button that reads "confirm solution." At this point, the user can select the tubing lead (i.e., micro line 2011 or macro line 2021) to be confirmed and can remove a protective cap that covers the lead. The user can then attach the appropriate spike. The user can then attach the source container to the tubing spike and hang the container on the rack or rail. The user is then presented with the interface of FIG. 22 whereby the user can scan the bar code flag 802 of the tubing lead for the solution to be confirmed. The user can then scan the source container bar code 801 for the solution attached to the tubing lead that is scanned. The lot number and expiration date bar can also be scanned (FIG. 23). The information from the bar code 801, as well as the lot number and expiration date could alternately be manually entered rather than scanned in. After completing confirmation of the first container, the user can select the "next ingredient" button shown on the interface of FIG. 24. This allows the user to repeat the steps of FIGS. 21-23 above that allows confirmation of all of the source solutions.

Once the source solutions have been confirmed, the user can initiate the priming of the solutions (step 3616 in FIG. 36). The user first attaches a receiving bag 80, i.e., calibration container, to the load cell 71. Then, after all of the solutions have been confirmed, the user taps the "prime" button shown in FIG. 25. After priming is completed, the user can select the "next ingredient" button in FIG. 24 and repeat this process for all stations. The user can initiate the manifold flush by selecting the "manifold flush" button in FIG. 24 once the stations have been primed (step 3618 in FIG. 36). Next, the user can initiate a pump calibration sequence via the interface of FIG. 26 (step 3620 in FIG. 36). The user can then follow steps 1-5 of FIG. 26 to calibrate the pump. These steps include confirming that that calibration final container is attached and marked "Not for Patient Use";

calibrate the macro pump; confirm that the macro pump is calibrated; calibrate the micro pump; and then confirm the micro pump calibration. The user can then remove and discard the calibration bag. The operator can then approve the setup of the fluid input stations (or decline and make further changes to the fluid input setup) (step 3622 in FIG. 36). The operator can then submit the pumping sequence for the fluid input stations (step 3624 in FIG. 36). Next, the operator inputs the admixture script (step 3626 in FIG. 36). The user can manually program an order for the solutions to be dispensed using the interface shown in FIG. 29. Alternatively, the user can scan in an order or select an order from a transaction pending buffer (TPB) manager or a .PAT file. Utilizing the interface of FIG. 29, the user can enter all of the solution volumes to be dispensed.

Next, the user can install the final container (e.g., receiving bag 80). The user may be presented with the interface of FIG. 27 that allows the user to select the final container (step 3628 in FIG. 36). The user may then be presented with the interface of FIG. 28 which allows the user to select the final container type, including whether a single chamber or a dual chamber receiving bag is desired, as well size of the bag (500 mL, 1 L, 2 L, etc.). The user can then scan or enter the lot number and expiration date. The user can then attach the final container by removing the protective caps and attach the receiving bag 80 to the transfer set connector. The user can then install or otherwise attach the receiving bag 80 by using the hanging holes formed in the container to connect to the load cell pins and then attach the tubing inlet to the tubing clip.

Figure 30:
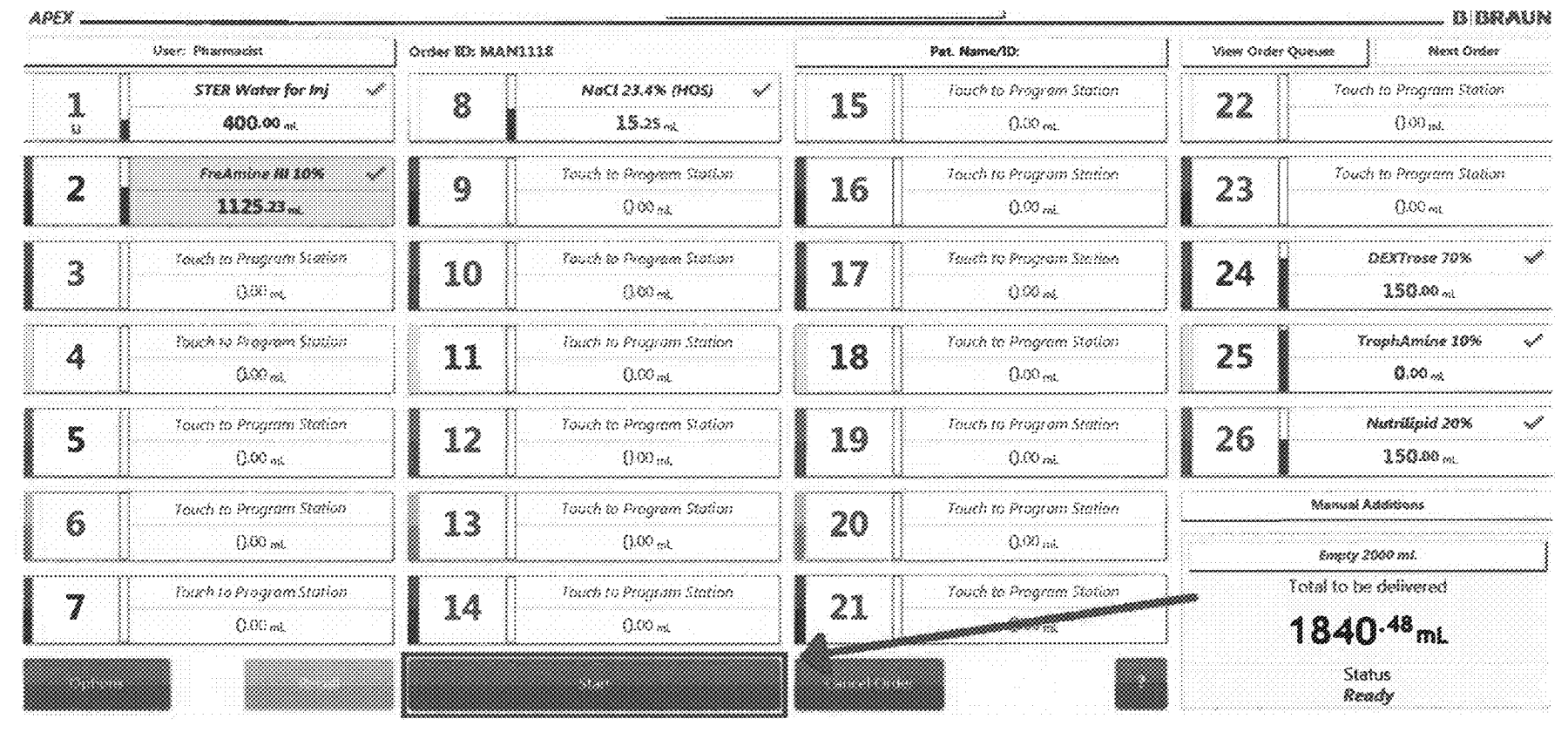

At this stage, the system has been calibrated, the solutions to be dispensed have been verified and the receiving bag 80 has been installed and is ready to be filled. As noted above, the solution volumes have all been programmed, so the user may now can select the "start" tab shown in FIG. 30 to activate the compounding process (step 3630 in 36). As shown in FIG. 30, if a solution requires a source container 4*a* or 4*b* change while compounding the next formulation, the station will display the solution requiring a change in yellow.

The controller 2900 can be configured to review the prescription and to require the user to either change the sequence of the script or to add a buffer to avoid incompatibility issues in either of the common channels 24*a, b* (micro/macro). The pump 40 will control deliveries from each of the common channels by stopping one or more of the pumps 40 if the incompatible fluids would meet in the union connector 60 after the pumps 40.

Figure 31:
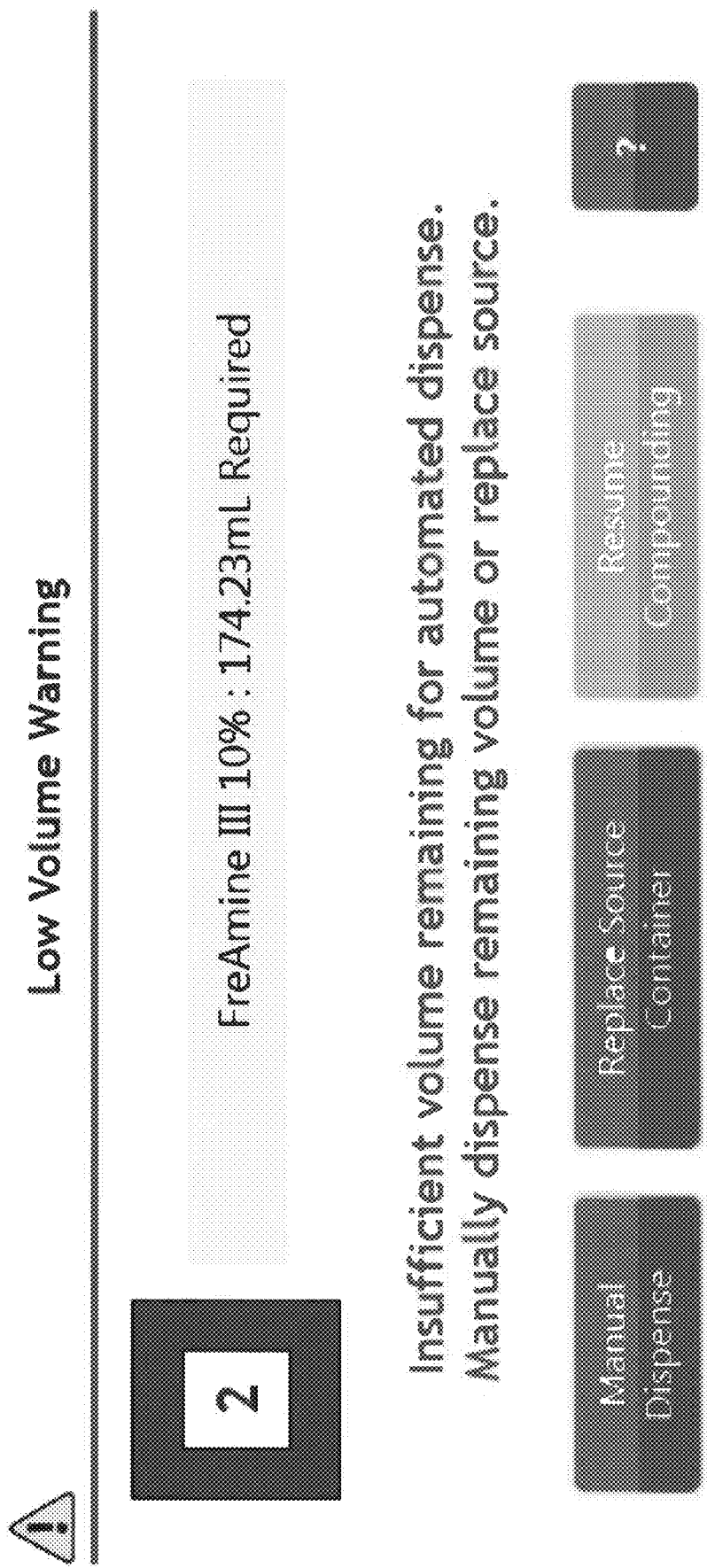
Figure 32:
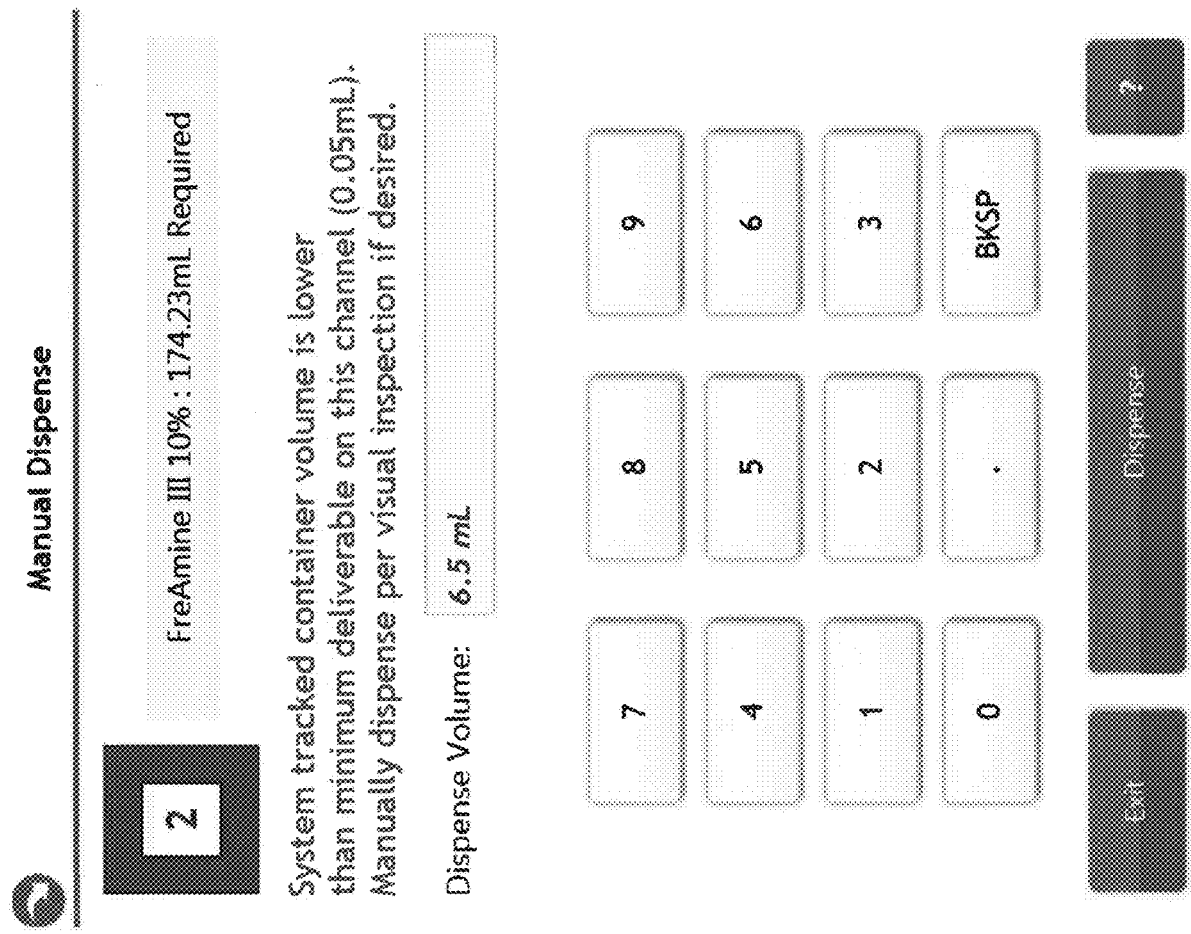
Figure 34:
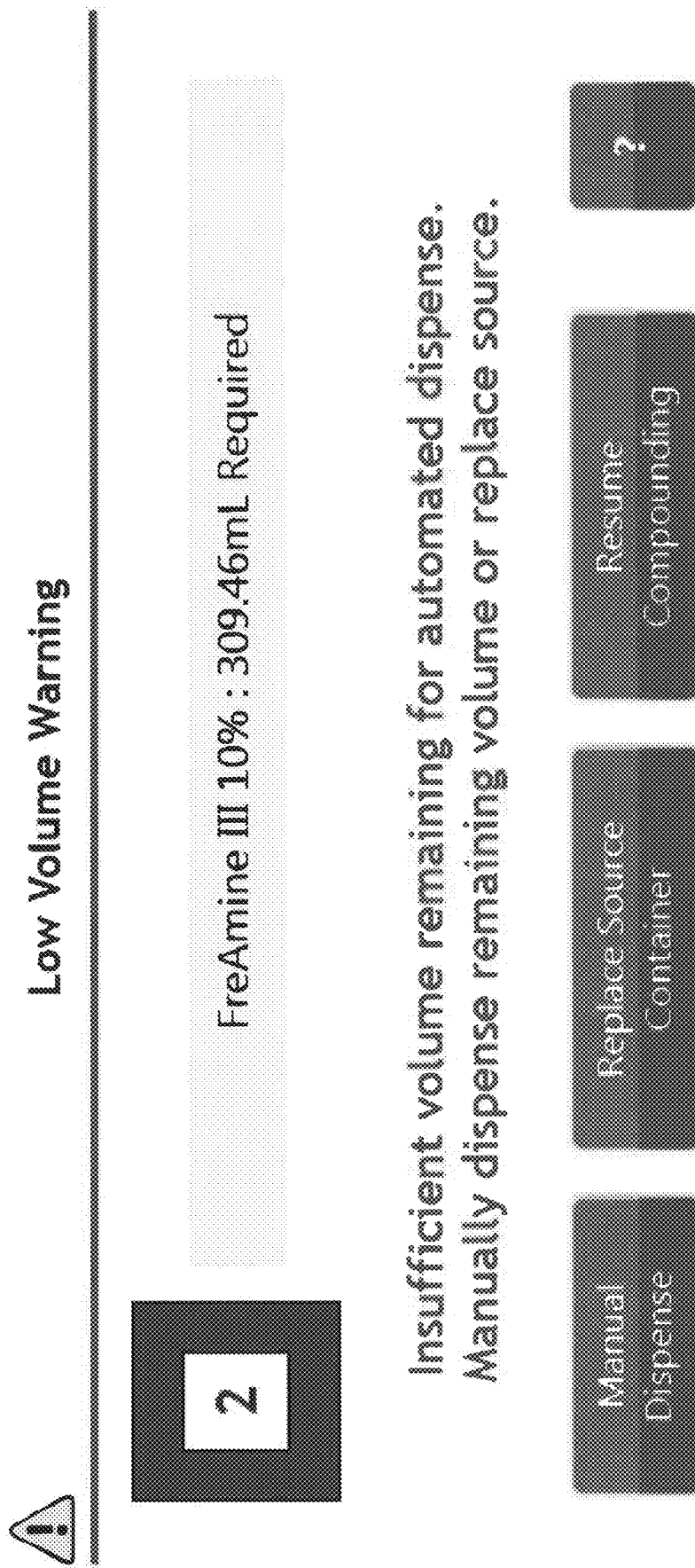

FIG. 31 shows a warning interface that is presented to the user when the software determines that the source solution container 4*a* or 4*b* has insufficient volume. The user can then replace the container or, if there is some solution remaining, a manual dispense can be performed. If the user chooses to perform a manual dispense, the user enters the estimated volume remaining in the pertinent source container using the interface of FIG. 32.

In order to replace the solution, the user can remove the empty container 4*a* or 4*b* and place a new container on the tubing lead and hang. The user can then access the interface of FIG. 33 to scan the bar code flag of the tubing lead for the new solution to be confirmed. The user can then scan the source container bar code for the solution attached to the tubing lead that is scanned. The lot number and expiration date bar codes can also be scanned. The user can then select the "confirm" button to complete this step. It should be noted that alternatively, the user may choose to manually enter this information instead of scanning the bar codes. The user can then resume compounding via the interface of FIG. 34.

Once the order is complete, the user can select the appropriate disposition for the receiving bag 80 (i.e., complete filling; scrap bag, etc.). Finally, the user can select the "apply disposition button." This completes the compounding process and the receiving bag 80 is ready for removal and can be used with a patient or other end user.

The fluid bag 80 resides on a gravimetric scale 71 that provides a final weight check back to the controller 2900 to verify that all compounded solutions were added. However, if a manual add of a particular component is necessary or desired during operation, the final check by the controller 2900 can be overridden. The load cell 71 can also be used to assist the pump calibration process, if desired. The controller 2900 can include hardware or software that performs calibration of the load cell 71 and pump 40. For example, the system can be configured to allow up to 6 verification weights to ensure the load cell is within required accuracy. The load cell can also check for instrument vibration to ensure that accurate measurements can be obtained. Furthermore, when dispensing an order, software is checking that the load cell value is always increasing to ensure that the operator remembered to connect the bag.

Pump calibration and in process calibrations ensure accuracy over the life of the disposable manifold 20.

The controller 2900 can also include a fluid line degradation algorithm such that degradation is accounted for during the life of the manifold 20. In other words, the number of motor rotations required to dispense a given volume of fluid increases as the tubing wears.

The controller 2900 can also include software and/or hardware to track and possibly mark bags such that manual adds can be added to a particular bag after automatic compounding. Use of a separate (possibly networked) control panel at a manual add station will open the compounding event and allow the user to manually add ingredients while tracking the fact that such ingredients were added before approving the bag for distribution to a patient or other user.

An algorithm can be incorporated into the software and/or hardware of the controller 2900 to determine if any bubble event requires the pump 40 to stop and for the user to verify if they accept the bubble that was sensed. A flow algorithm can also be incorporated in coordination with the use of pressure sensors to detect occlusions and/or flow pressures. Furthermore, it is conceivable that intelligent bubble handling technology can be incorporated into either the controller 2900 or the occlusion or bubble sensor(s) 33*o*, 33*s*, 33*o/b* that monitors what has been delivered into the common volume (and attempts to determine a worse case bubble event). The technology can include hardware and/or software that causes the system to stop and require a user to accept or reject the operation depending on the presence (or lack thereof) of bubbles or an occlusion, etc. Software and/or hardware can also be provided that determines whether any occlusion or bubble event, when weighed against the size/volume of delivery, was large enough to effect accuracy, and provide a user with an automated or user defined option to accept or reject delivery of the end product.

The interface for the controller 2900 can include dual display of stations that uses colors and/or numbers to identify each station. The screen for the controller 2900 can include a first column that represents flex lines, a second and third column that represent micro lines, and a fourth or last column that represents macro lines. The screen can group the different (in this case, three) types of stations in order to present a clear picture of what fluids are at what station and what type of station it is. Of course, the number and arrangement of micro, macro and flex lines can change depending on a particular application for a different embodiment of the compounding system 1.

The controller 2900 can also be configured to require a username/password or bar coded badges to sign in/out. In addition, access can be further controlled to require username/password or bar coded badges for confirmation of required steps (e.g., addition of an ingredient that requires a prescription or that is in another way regulated).

The controller 2900 can also be configured to display a real time status of the compounding event. For example, the controller 2900 can display which solution(s) are currently being pumped from which station as well as how much solution is left in each source container 4a, b.

Templates can also be stored in the controller 2900 to quickly and efficiently determine the set-up and sequence of ingredients for a particular application or a particular patient or user. A database located in or accessible by the controller 2900 can include data related to storage, additions, removals of all drugs allowed for compounding and their associated data. The controller 2900 can be configured to include multiple interfaces for the user and can be networked such that a plurality of compounding devices can be controlled and/or monitored by a separate entity or controller. In addition, a print wizard can be incorporated into the controller 2900 software and/or hardware that automatically prints certain items when certain actions take place using the compounding device.

While certain embodiments of the invention are described above, it should be understood that the invention can be embodied and configured in many different ways without departing from the spirit and scope of the invention.

In another alternate exemplary embodiment, the occlusion sensor and bubble sensor can be positioned under the manifold common volume. Although locating the sensor area in the common volume in the manifold may make the flushing act slightly more difficult, the location of the bubble sensor in the common volume can allow a user to better discriminate which source line generated the bubble. For example, an array of bubble sensors could be located along the length of a common volume in the manifold to accomplish this feature.

In yet another exemplary embodiment, the filler 200 could be removed from the micro common volume (e.g., first channel 24a) and the inner diameter of the common volume could be reduced as compared to the volume depicted in, for example, FIG. 6B. This modification comes with certain complications in that manufacturing and design of the valves would be more complicated to affect the volumetric flow rates desired in the modified first channel 24a of the compounding device.

In another embodiment, the filler 200 could be configured with vanes on its outer diameter (OD) surface that induce turbulence and/or swirl to promote better flushing. Additionally, the filler 200 could be removable from the channel in order to provide an alternate flushing port. Likewise, the filler 200 could be removable such that different style fillers (e.g., fillers having different cross-sectional shapes, sizes, number and shape of vanes, etc.) could be used in the manifold 20.

In yet another embodiment, a cross connect channel can be located between the downstream end of the micro and macro common volumes (e.g., the first channel 24a and second channel 24b). A valve could be provided to close this channel, allowing dispensing to occur as usual, and then the valve could be opened to allow the micro common volume to be flushed by the macro pump, which operates at higher flowrates and provide more efficient flushing.

As described above, the platen/lock arm design has springs in the lock arms that press the platens against the rotors 41, 42 when the lock arms 44a, b are closed. An alternate approach would locate torsional springs at the platen hinge points (potentially inside the instrument) such that the platens are always spring loaded against the rotors. The platen lock arms 44a, b could be replaced by "platen disengagement arms" configured to pull the platens 43a, b away from the rotors 41, 42 during transfer set installation and removal.

The pump output is a function of upstream suction pressure. To provide better volumetric accuracy, the occlusion sensor could be used to compensate for variations in upstream suction pressure and prevent alarms due to partial occlusions. In this approach, the number of commanded pump rotations and rotor speed could be adjusted based on the measured suction pressure during pumping.

In yet another embodiment, LEDs or other types of lights or light sources can be located in the top surface of the pump under each ingredient source line. The molded manifold would guide light into the source tubing line, possibly all the way up to the spike where a visual indication could be provided if a source container or line needs attention. The light or light source would be connected to the electronic control unit for the compounding device, which would dictate when and how to provide light to a particular location, depending on error codes, programming desires, reminder notices, etc.

While it has been disclosed that a plurality of different sizes and shapes of tubings/lines and containers can be connected to the compounding device, in yet another alternative configuration of the disclosed subject matter, the compounding device can be configured for use with only a single type of container and tubing, such as only macro lines and macro containers, or only micro lines and micro containers. In this manner, the compounding device can be an effective replacement for current compounding systems and applications that include only single types of containers and lines.

The number of channels can also vary and remain within the scope of the presently disclosed subject matter. For example, three, four or more different sized channels could be incorporated into the manifold. Similarly, more than one same shaped and sized channel could be included in the manifold 20.

The strain relief clip 33 is disclosed as being pre-assembled to the lines 2011 and 2021. However, it should be understood that the strain relief clip 33 or similar structure could be attached during use or installation of the manifold. Moreover, the strain relief clip 33 could be attached only when its function is needed for a particular application. Similarly, the strain relief clip 33 can be configured in various different shapes and sizes and attached at different locations on the line or tubing. The strain relief clip 33 could also be configured as a two piece structure that can be attached at different locations on a respective one of the lines. It is also contemplated that the strain relief clip 33 can be integrated into the bubble occlusion sensor or vice versa. In addition, the strain relief clip 33 can be configured as a dampening material, adhesive or putty that can be located at a portion of the line(s) and attached to the housing to dampen movement of the lines where strain would otherwise be present.

The pump cover door could be mechanically interlocked with a specific position of platen locks (for example, a user can be prevented from closing the door if both platens are not locked into place). A lip can be provided on a lower portion of the platen to ensure that the user does not mislead a pumping segment of the tubing line to a position that is too low and that would possibly be captured between the platen and the base of the rotor (instead of being correctly placed on the roller).

The many variations and alternate structures described herein are contemplated for use in all various combinations and permutations with each other, and without certain features or components (for example, the filler can be provided without vanes 202, and the micro channel can be provided without flex ports 20bf, etc.)

The disclosed embodiments also provide a system and methods for controlling various operational characteristics of the compounding device. For example, the disclosed embodiments provide a system and methods for determining when the transfer tubes should be replaced due to excessive wear. The term "transfer tubes" refers to any of the lines used to transfer fluid, such as the input lines 2011, 2021 and the output line 2031. The transfer tubes are also referred to as "transfer lines," "fluid transfer lines" or "fluid lines." In one embodiment, an alert is issued so that an operator is notified that one or more transfer sets should be replaced. The determination of tube wear can be made based upon a variety of factors, including changes in the volume of fluid being transferred over time and/or changes in the weight of the filled IV bag as compared to a baseline IV bag weight. Furthermore, the pumping segments are characterized via testing and the data is utilized to determine tube wear profiles, which are used in the formula to determine a number of rotor turns per fluid volume during the life of the tube set.

In another embodiment, a system and methods are provided for controlling the transfer of fluid so that incompatible fluids are not transferred simultaneously. Thus, incompatible fluids are prevented from being combined at the union junction. The term "incompatible fluids" refers to two or more fluids that react in an adverse or otherwise undesirable manner when they are combined with one another.

The disclosed embodiments also include a system and methods for determining whether a fluid should be transferred through a macro or micro transfer tube. This determination results in control instructions for activating macro line and micro line pump motors that cause fluid to flow through the appropriate fluid transfer lines.

Figure 35:
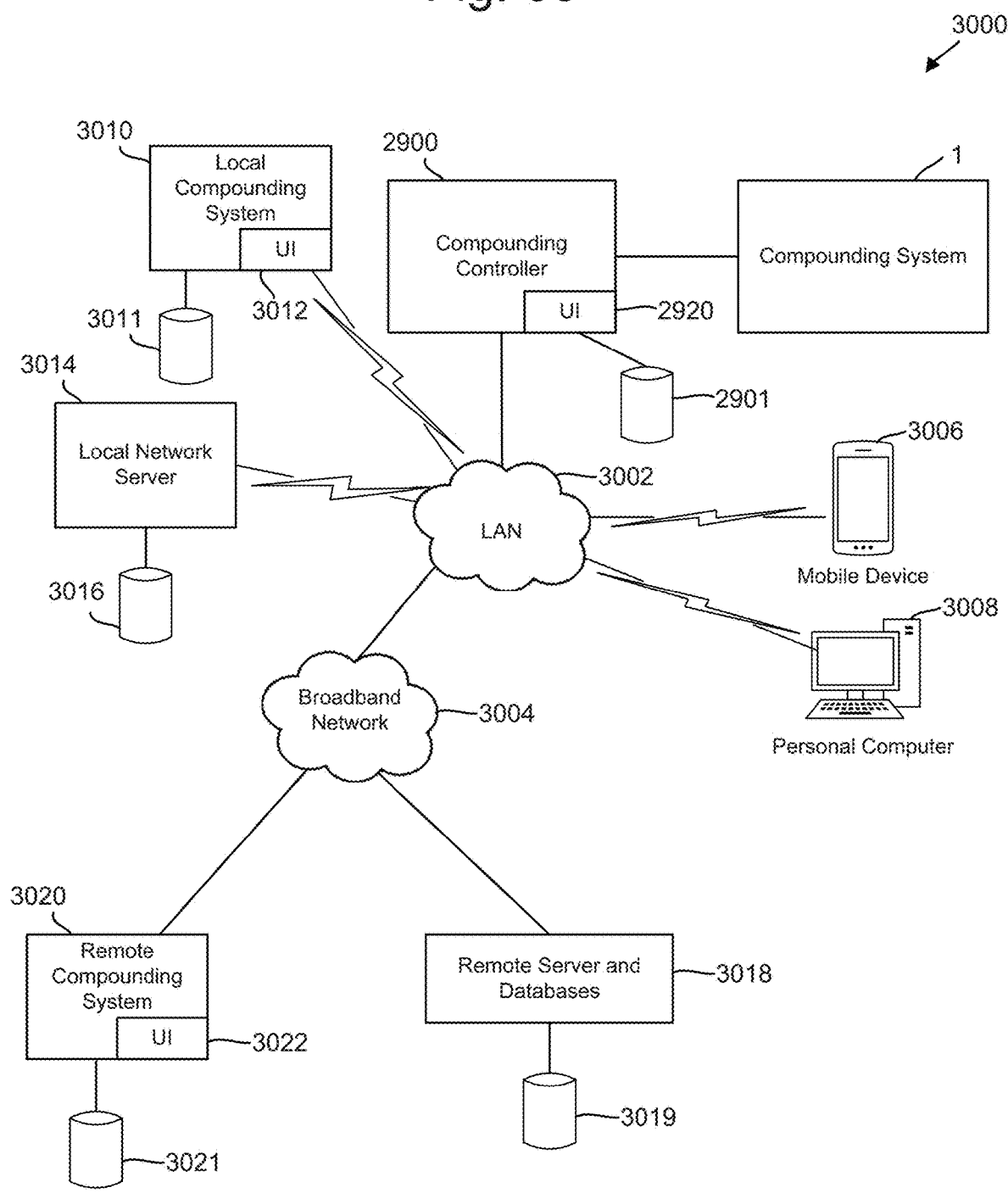
FIG. 35 is a diagram of an exemplary network environment of an exemplary compounding device controller in accordance with the principles of the disclosed subject matter.

FIG. 35 is a diagram of an exemplary network environment of the exemplary compounding controller 2900 for the compounding system 1 in accordance with embodiments of the disclosed subject matter. The environment 3000 could be any network that can access a broadband network 3004 (i.e., the Internet), and a local area network (LAN) 3002 (i.e., a hospital network), which is a managed network, such as an Internet Protocol, Asynchronous Transfer Mode (ATM), Ethernet, etc. The controller 2900 can operatively connect to a communication interface that can connect to the LAN 3002. The LAN 3002 can include an Internet gateway device that connects to the broadband network 3004 using any appropriate network access protocols. The controller 2900 may interconnect through the broadband network 3004 with a remote server 3018, having one or more databases 3019 of information relevant to the operation and methods of the controller 2900, or a remote compounding system 3020 having a user interface 3022 and one or more databases 3021 of information relevant to the operation and methods of the controller 2900. The controller 2900 may interconnect through the LAN 3002 on wired or wireless network links to one or more compounding system 3010 with user interface 3012 and one or more databases 3011 of information relevant to the operation and methods of the controller 2900. One or more mobile devices 3006 and one or more personal computers 3008 may connect to the controller 2900. The personal computer 3008 may have a keyboard, display, processor, and memory and can be a desktop or portable laptop computer. The mobile device 3006 can be any appropriate mobile computing device such as a tablet, smart pad, smart phone, or other hand-held device, etc. with a display, processor, memory, and user interface. The personal computer 3008 or mobile device 3006 may be configured to enter information, such as a script and input instructions to the controller 2900.

As shown in FIG. 35, the controller 2900 may also connect via the LAN 3002 with a local network server 3014 having a processor, memory, and a database 3016 with information relevant to the operation and methods of the controller 2900. In one embodiment, the compounding device 3010 and/or local network server 3014 may be located in different areas of a healthcare facility such as a hospital, or on different floors of a hospital or even different hospitals that are networked together over the LAN 3002. In some embodiments, compounding processes described herein may be performed simultaneously by multiple local or remote compounding systems with the compounding system 1. In other words, the controller 2900 can be configured to control other compounding systems 3010, 3020 over the network LAN 3002 or broadband network 3004. The controller 2900 can be interconnected with the personal computer 3008 through the LAN 3002 or through a direct wired connection. The personal computer 3008 can be a general hospital computer that can be used to access patient records and handle requests from medical facility staff or hospital software for compounding admixtures. In other embodiments, the compounding device 3010, local server 3014 and personal computer 3008 may all be located in the same area or room so that the local server 3014 and personal computer 3008 directly communicate with a single compounding device 3010.

The controller 2900 can have sufficient memory for storing pharmaceutical data in the form of a database, a processor for running operating software, and transmitting information to the user interface (UI) 2920 for use in displaying information to a user and receiving input from the user. In other embodiments, the controller 2900 may include a main controller and one or more additional controllers in a distributed network architecture. In such a configuration, the main controller may provide supervisory oversight and management of the compounding operations, and coordinate the performance of sub-operations by the other distributed controllers. The controller 2900 may include one or more processors that performs operations according to software that may be developed and compiled using one or more languages. The controller 2900, and in some embodiments one or more additional sub-controllers, may be in the form of embedded systems, having dedicated controllers, PLCs (programmable logic controllers), PC-based controllers with appropriate networking and I/O hardware and software, ASICs, or other implementation. For example, one controller can be dedicated to controlling stepper motors 102a, 102b for the micro valves 21a and macro valves 21b and stepper motors 41s, 42s, for the micro pump 41 and the macro pump 42. Motor actuation planning can involve the actuation of the micro valves 21a and macro valves 21b to optimize conveyance of fluids through the micro pump 41 and the macro pump 42. Data can be provided in firmware for the controller 2900 for purposes of handling various types and sizes of IV bags as final containers, as well as the expected locations and orientations for various inventory items throughout the stations on the system 1 including the ingredient frame 1, the transfer set 2, the sensor bridge 10, the pump 40, and the discharge tray 70. The controller 2900 can have access to the databases 2901, 3011, 3019, 3021 directly or through a network connection.

FIG. 37 is a flow chart of logical steps for an exemplary process for controlling a compounding system 1 in accordance with the principles of the disclosed subject matter. The process can initiate at step 3702 and proceed to step 3704 where the compound manager is activated. The process then moves to step 3706 where the controller 2900 can receive input from the user input and associate the user's level of security clearance with each input and command request. For example, in a medical center scenario, templates of various scripts may be available for admixture compounding. If a doctor or nurse requests a prescription such that a concentration of a controlled pharmaceutical ingredient exceeds the limits allowed by the template, then the controller 2900 can demand a higher security level than an administrative operator to login and make the prescription changes. In another embodiment, certain patient templates could require one or more specific doctors or nurses to personally login and override the template's pharmaceutical limits. In other embodiments, the controller 2900 may require further information from the authorized operator to exceed the pharmaceutical limits in the template and can save the information with the patient's data.

After receiving the login credentials of the user, the controller 2900 can receive setup information for the compounding process. In step 3706 the controller can receive instructions to initiate and complete daily checklist items, such as various maintenance tasks. The process then moves to step 3708 where the controller 2900 receives instructions to initiate and complete load cell calibration. In the next step 3710 the controller 2900 can receive identifying information relating to the transfer set 2 that should be used. This identifying transfer set information can include any appropriate data that identifies the transfer set 2, such as data from a bar code scan of the transfer set 2 or an input of a transfer set serial number received from the UI 2920. After the user verifies completion of the transfer set 2 installation, using, for example, UI 2920 in FIG. 18, the user can initiate calibration using, for example, UI 2920 of FIG. 19. The controller 2900 can receive calibration instruction input from the user's initiation of a pump calibration sequence via the UI of, for example, FIG. 26 and initiate the calibration process for the first (macro) pump 42 and the second (micro) pump 41. Although the process here is described in terms of the calibration of the micro pump being performed first, it should be understood that the disclosed embodiments contemplate that the order of calibration can be reversed and/or changed as may be required by a user.

Calibration can be performed independently by the controller 2900 or in other embodiments incorporated as part of a fluid line degradation algorithm described more fully below. In the next step 3712 the controller 2900 receives confirmation that the transfer set was installed and that a leak test will be initiated and completed.

In the next step 3714, the controller 2900 receives a selection for the number of stations of material source fluids that are to be used (also referred to as the fluid input station selections) as well as confirmation of those fluid input stations. The controller 2900 can then receive material source configurations for each bag of material sources confirmed in specific locations on the ingredient frame 3 and connected to the plurality of micro fluid lines 4*a* and macro fluid lines 4*b*

The controller 2900 then receives instructions for initiating and completing the priming of the fluid input stations in step 3716 followed by initiation and completion of the manifold flush procedure in step 3718. The controller 2900 receives instructions for the initiation and completion of the pump calibration process in step 3720. The controller 2900 receives instructions for the approval of the fluid input stations setup in step 3722 followed by receipt of the fluid input station pumping sequence in step 3724

Next, the controller 2900 can receive instructions for the script of ingredients (admixture script) in step 3726 and information describing solution volumes to be dispensed to the final container 80 (step 37328. Based on the data and information received and the volumes and types of script ingredients, the controller 2900 can determine a preparation order so that the system 1 prepares the script ingredients sequentially or simultaneously, using either the macro pump 41, the micro pump 42, or both. In the next step, the controller 2900 can control the compounding system 1 to prepare the admixture (step 3730.

As shown in FIG. 37, the process includes three different procedures which can be implemented by the controller 2900 and undertaken simultaneously in order to monitor or otherwise improve operations, actions, or aspects of the compounding system 1. The first procedure is a process for initiating the pump control algorithm (step 3732), the second procedure is a process for initiating an algorithm to determining whether incompatible fluids are being introduced into the system (step 3734 and the third procedure is a process for detecting and calculating degradation of the fluid lines (step 3736.

Pump Control Process

The process for initiating the pump control algorithm is now described in conjunction with FIGS. 38*a*-38*d*. The disclosed embodiments are directed towards the generation of instructions for controlling the operation of the pumps. As stated above, some compounding devices use a peristaltic pump mechanism driven by a stepper or servo type motor to turn the pump mechanism in precisely measurable increments. The system and methods according to the disclosed embodiments also determine whether a pharmaceutical or other source solution should be delivered using a micro fluid flow path or a macro fluid flow path to the final container 80. An examination of input data can result in a logical decision by the controller 2900 to activate the corresponding macro or micro pumps 41, 42. The software in the controller 2900 can also control the use of a flex line. This logical decision can be based upon the type of fluid to be delivered, the volume to be delivered, and other factors.

Thus, the disclosed systems and methods utilize the controller 2900 for storing in a memory instructions for activating the micro and macro fluid flow paths depending upon the ingredients to be dispensed. The processing method can include receiving setup data in the controller 2900, the setup data being indicative of a plurality of micro and macro source solutions connected to a plurality of macro fluid lines or a plurality of micro fluid lines. The setup data can also be indicative of a plurality of micro valves connecting the micro fluid lines to a micro pump, and a plurality of macro valves connecting the macro fluid lines to a macro pump. The setup data can also include a script that is to be dispensed using the micro and macro source solutions. The controller 2900 can prepare the system 1 for fulfilling the script grouping the source solutions into a micro group that is transferred by the micro pump and a macro group that is transferred by the macro pump. The controller 2900 can generate instructions for preparing the compounding system 1 to selectively transfer the micro group source solutions using the micro pump 41 and to selectively transfer the macro group source solutions using the macro pump 42. The controller 2900 can receive pump data from one or more sensors that sense actions of the micro pump 41 and the macro pump 42, the pump data being indicative of an amount of source solution displacement by the macro pump 42 or the micro pump 41. The controller 2900 can then operate the micro pump 41 and the macro pump 42 to selectively dispense the source solution amounts according to the preparation order.

In FIG. 38*a*, an algorithm can initiate the process in the controller 2900 and in step 38*a*02 the controller can receive information relating to the material source solutions located across all of the input stations (for example, in the micro and macro input containers 4*a*, 4*b*). The type of data relating to the material source solutions includes the identity of each fluid on each line. The process then moves to step 38*a*06 if the material source solutions require the use of a micro line or to step 38*a*10 if the material source solutions require a macro line. If the material source solutions require a flex line, then the process moves to step 38*a*04 where the controller 2900 can examine the scripted volumes associated with the flex line source solutions. Then, the process moves to step 38*a*08 whereby the controller 2900 associates the flex flow path components, including the input containers, the input lines and the valves. Steps 38*a*06 and 38*a*10 reflect a flex line algorithm that determines whether a fluid should flow to a micro or macro line. For example, the flex line logic would determine that a micro line should be used if a small spike is being used, while a macro line should be used when a larger spike is used. A determination is made as to the type of spike being used. In step 38*a*08, if the flex line algorithm determines that a micro line should be used (based upon volume dispensed), then the process moves to step 38*a*06 while if, in step 38*a*08, the flex line algorithm determines that a macro line should be used (based upon volume dispensed), then the process moves to step 38*a*10. In general, smaller volumes go to the micro channel for high precision, while larger volumes go the macro channel for higher speed.

In step 38*a*06 the controller 2900 associates the micro flow path components, including the input containers 4*a*, input lines 2011, valves 21*a*, manifold channel 20, output line and pump 41. In step 38*a*10 the controller 2900 associates the macro flow path components, including the input containers 4*b*, fluid lines 2021, valves 21*b*, manifold 20, channel 24*b*, and the macro pump 42.

As shown in step 38*a*08, the controller 2900 can also associate flex line flow path components including the input containers 4*b*, fluid lines 2011, 2021, valves 21*a*, 21*b*, manifold 20, channel 24*a*, 24*b*, and pumps 41, 42.

In the next step 38*a*12 the controller 2900 can create a logic table of associated flow paths, including operations for the micro flow path, the macro flow path, and the flex line flow path components. Next, in step 38*a*14, the controller 2900 can examine the scripted volumes and the dispensing sequence to prepare the operation instructions for the micro and macro pumps 41, 42.

The process then moves to step 38*a*16 whereby the controller 2900 receives user interface input to initiate compounding activity. The process then moves to FIG. 38*b* executing steps 38*b*02-38*b*14 (micro flow path) in parallel with steps 38*b*16-38*b*28 (macro flow path). In step 38*b*02, the controller 2900 determines the first or next solution to be dispensed along the micro flow path. The process then moves to step 38*b*04 where the controller 2900 applies flow rate factors pertinent to the source solution about to be dispensed. The flow rate factors refer to characteristics of each fluid and can be based upon various fluid characteristics such as viscosity, specific gravity, etc. The flow rate factors of a fluid can also be determinative of whether a particular fluid is more prone to forming an occlusion within a fluid line. The flow factors can also be a function of other factors, including the source container, the spike type, the line type and the pump speed.

The process then moves to step 38*b*06 where the controller determines the current location of the micro pump rotor as well as the location of the roller. In one embodiment, the location of the pump rotor and/or roller can be determined based upon a sensor that scans an initial position of the rotor and/or roller. Thus, a determination of rotor and/or roller position can be determined by observing a current position against a known starting position.

The process then moves to step 38*b*08 where the controller 2900 calculates an angular displacement of the micro pump rollers to dispense an accurate volume of the fluid. The process then moves to step 38*b*10 where the controller applies a micro pump roller correction factor and re-calculates a required angular displacement of the micro pump rollers. In one embodiment, this correction is performed by assuming that the rotor is in one of four positions and then resetting the baseline based upon the nearest quarter turn. The process then moves to step 38*b*12 where the controller 2900 commands the micro pump motor to rotate the rotor a corresponding distance, and then re-calculating the angular displacement distance. The process then moves to step 38*b*14 where the controller 2900 determines whether the micro pump motor has rotated a complete distance for the selected source solution to have been dispensed. If the system determines that the pump motor has rotated the complete distance for the fluid to be dispensed, then the process moves to step 38*c*02 shown in FIG. 38*c*. If the system determines that the pump motor has not rotated the complete distance for the fluid to be dispensed, then the process moves to step 38*d*02 in FIG. 38*d*. At this point, a warning may be initiated whereby the operator is notified if, for example, the selected fluid amounts exceed the IV bag capacity, if the selected fluids are incompatible in the quantities selected or if enough of a buffer solution is not selected or available. The warning will allow the operator to stop the process until the issue is addressed FIG. 38*b* also illustrates steps 38*b*16-38*b*28 that mirror steps 38*b*02-38*b*14 described above, except that steps 38*b*16-38*b*28 are related to dispensing a fluid along a macro fluid path.

Figure 38B:
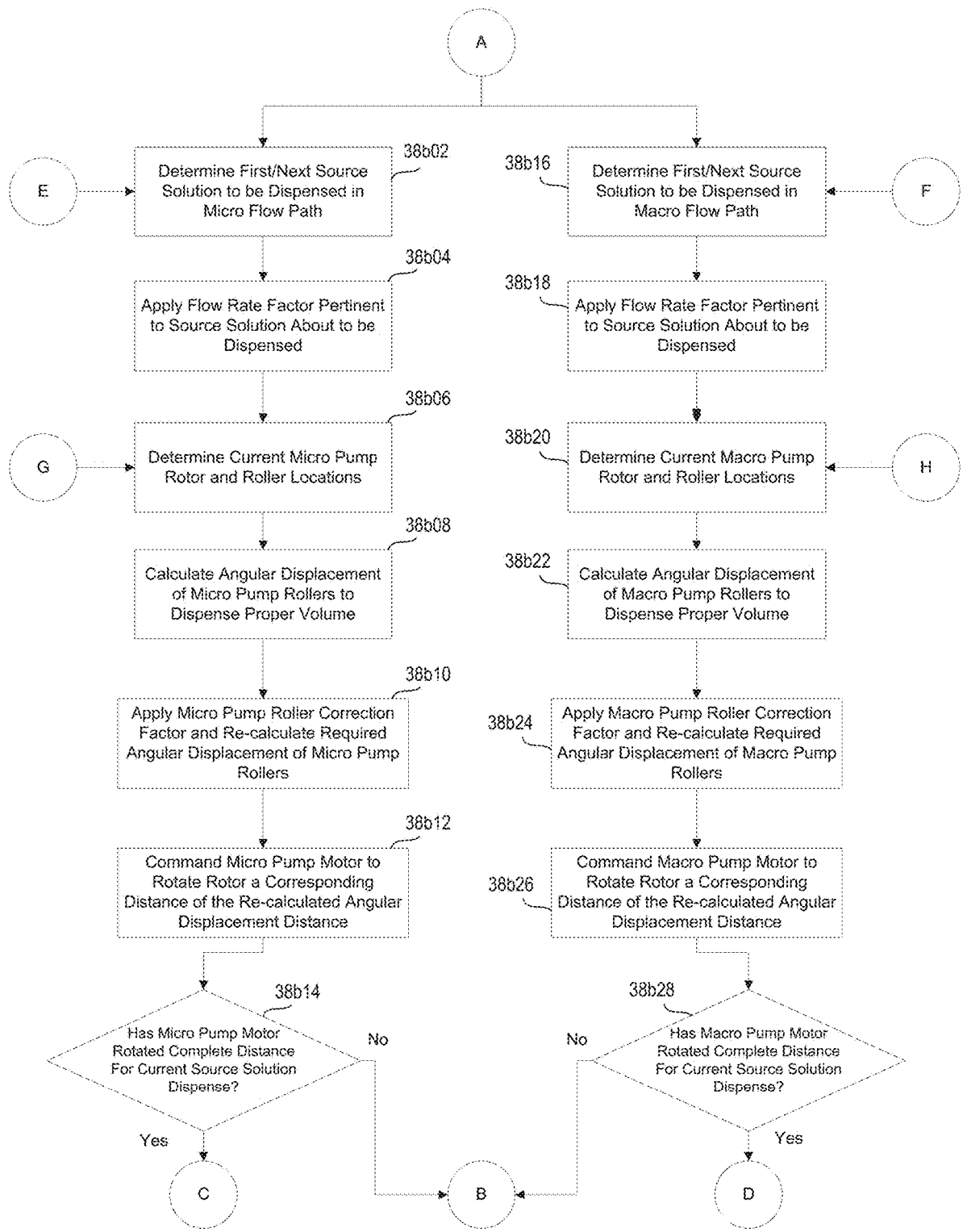
Figure 38C:
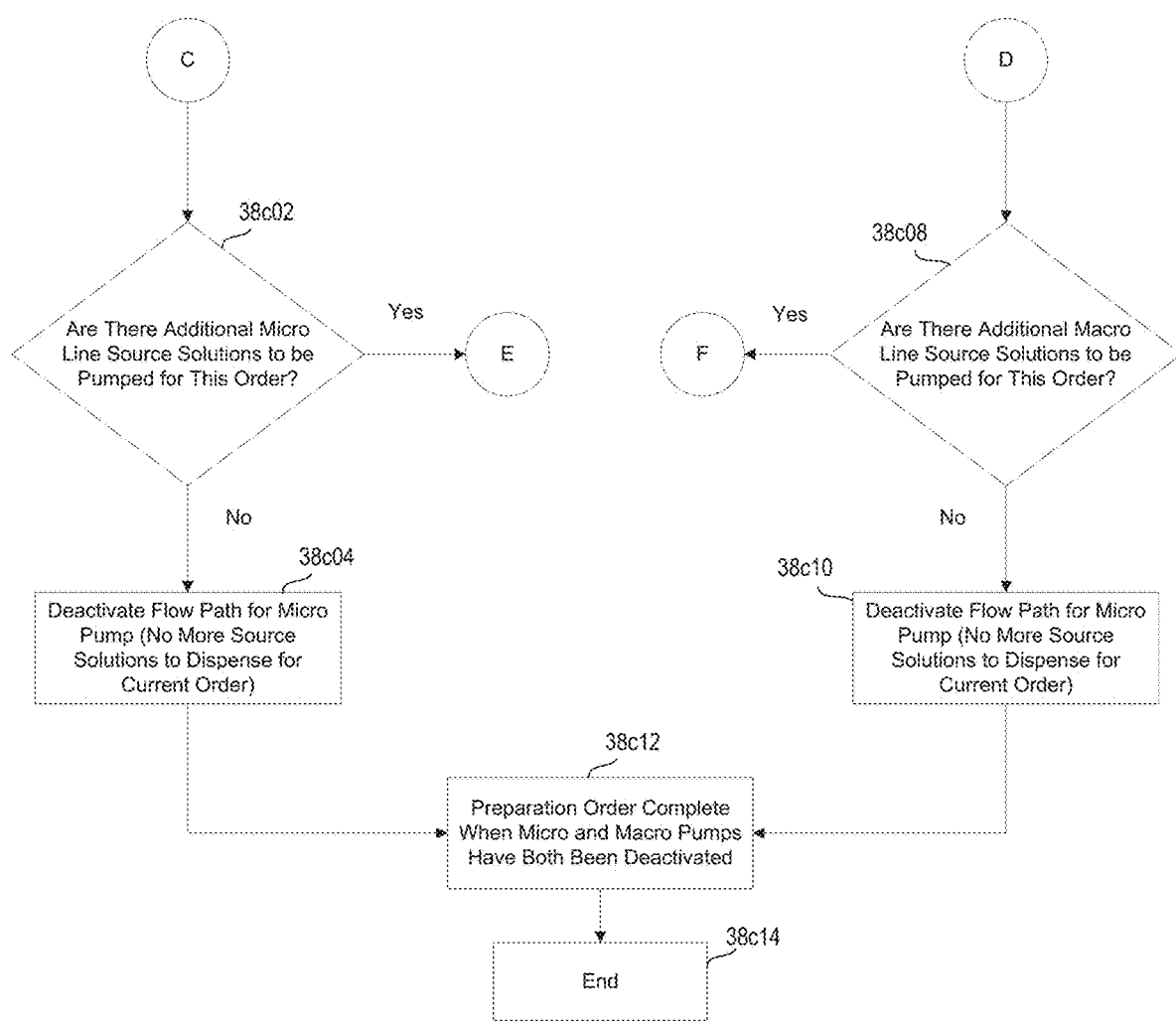

As described above, if the system determines that the pump motor has rotated the complete distance for the fluid to be dispensed, then the process moves to step 38*c*02 shown in FIG. 38*c* for the micro flow path or step 38*c*08 shown in FIG. 38*c* for the macro flow path. In step 38*c*02, the controller 2900 determines whether there are any additional micro line source solutions to be pumped for the current order. If there are additional micro line source solutions to be pumped, then the process returns to step 38*b*02 in FIG. 38*b*. In step 38*c*04, if there are not any additional micro line solutions to be pumped, then the controller 2900 deactivates the flow path for the micro pump so that no more source solutions are dispensed. The process then moves to step 38*c*12 where the controller 2900 receives confirmation that the order has been completed because both the micro and macro pumps are deactivated. The entire process then ends at step 38c14. Steps 38c08-38c10 parallels steps 38c02-38c04 except that in steps 38c08-38c10, the determinations are made for a macro pump.

Returning to FIG. 38d, the process continues at step 38d02 because there was a determination at step 38b14 that the micro pump motor had not rotated a complete distance for the current source solution to dispense. In step 38d02, the controller 2900 initiates a protocol to determine the reason for the incomplete micro pump motor rotation. The process then moves to step 38d04 where the controller 2900 determines whether there was a system error, such as a hard failure, or an instruction to abort the process, that should cause the order to end. If there is a reason to stop the process, then the process moves to step 38d08 where the controller provides feedback to the user interface and provides pertinent error handling procedures. The process then ends at step 38d10. In step 38d04, if the controller 2900 determined that there was no system error, then the process moves to step 38d12 where the controller 2900 determines whether there was a user initiated pause event. A user initiated pause event could be triggered by various events, such as if the operator depresses a pause button or if the compartment door is open which can cause the pumps to cease operation.

If the controller 2900 determines that there was a user initiated interrupt event, then the process moves to step 38d14 where the controller 2900 waits to receive a prompt from the operator to resume the process. The process then moves to step 38d16 where the controller 2900 calculates the volume of the current micro source solution that remains to be dispensed. The process then returns to step 38b06 in FIG. 38b where a determination of the current micro pump rotor and roller locations is made.

Figure 38D:
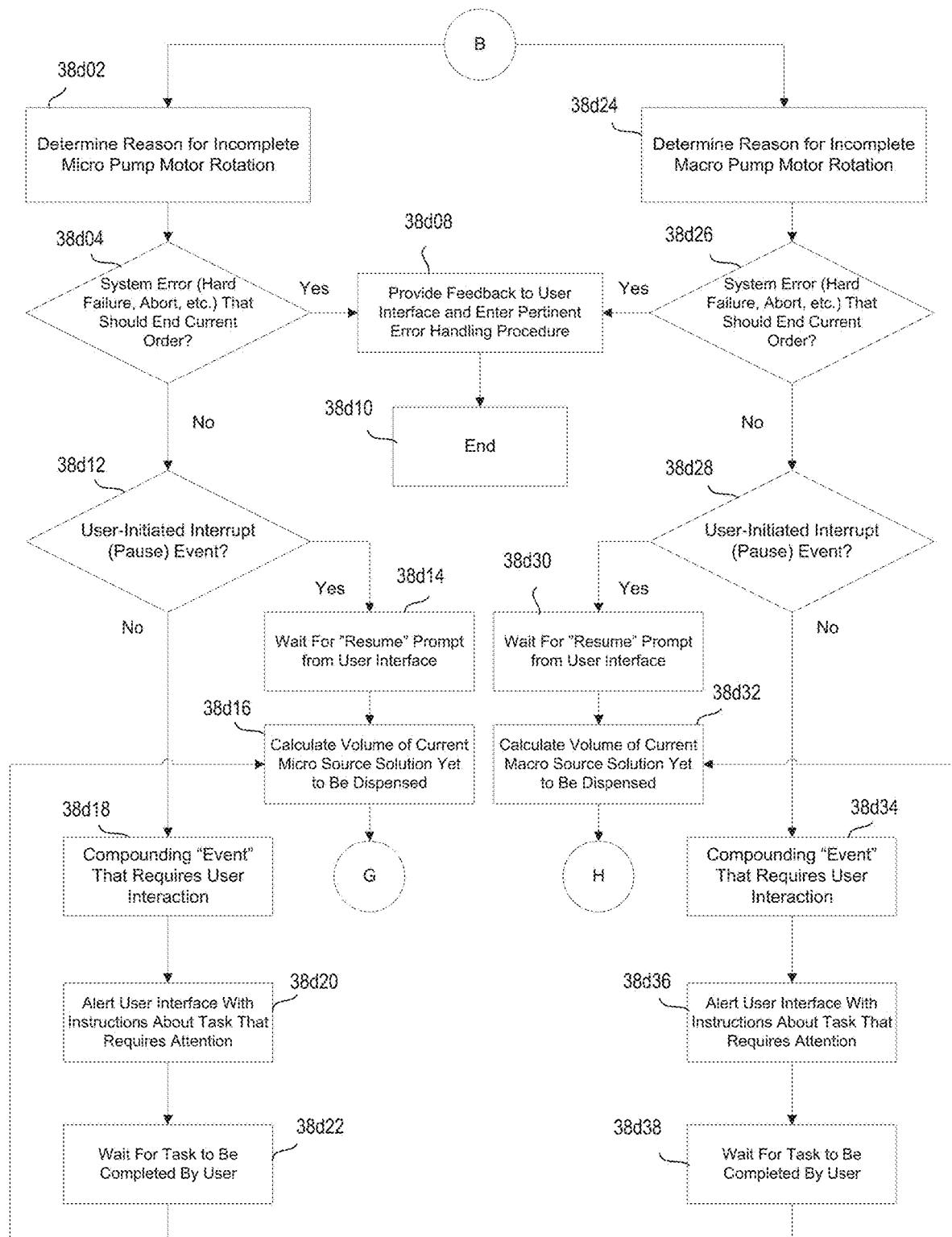

Returning to step 38d12, if the controller 2900 determines that there is no user initiated interrupt event, then the process moves to step 38d18 where the controller 2900 determines whether there was a compounding event that requires user interaction. The process then moves to step 38d20 where the controller 2900 alerts the user interface to provide the operator with instructions about an outstanding task that requires attention. The process then moves to step 38d22 where the controller 2900 waits for the task to be completed by the user. The process then goes to step 38d16 where the controller 2900 calculates the volume of the current micro source solution that remains to be dispensed. The process then returns to step 38b06 in FIG. 38b where a determination of the current micro pump rotor and roller locations is made. FIG. 38d also illustrates steps 38d24-38d38 which parallel steps 38d02-38d22 except that steps 38d24-38d38 relate to determinations for the macro pump motor. At this stage the algorithm for controlling the pumps has been completed.

Incompatible Fluid Detection

The controller 2900 also initiates an algorithm for pump control to prevent simultaneous drawing of incompatible liquids into a common flow path. In the compounding process, fluid solutions are drawn from small or large containers 4a, 4b into micro input lines 2011 or macro input lines 2021. The compounding system 1 can be configured to combine the input lines into a single output line 2031 at the union junction 60, and subsequently to the final collection point, such as the intravenous fluid bag 80. Much of the complexity of a pharmacy practice involves determining if different ingredients within solutions or materials of a prescription will have compatibility issues caused by the concentrations or preparation order of the script. Compatibility of material sources for a script can be defined as an interaction between a material source ingredient, such as a drug, and all other ingredients and components with which the drug comes into contact. "Compatibility" of a drug or other material ingredient in a compounding process refer to either a physical compatibility or a chemical compatibility. Physical compatibility can be an incompatibility that will alter the physical appearance of an ingredient, which can result in a visual change such as precipitation, gas evolution, or a change in color. Chemical incompatibilities may not always be visually observable but must be analytically tested. Chemical incompatibilities can occur as a result of changes in the active ingredient such as oxidation or photodegradation. Factors that can influence compatibility include, but are not limited to, the total diluent volume, concentration levels, the order of admixing, and the pH. However, it can be difficult to determine material source incompatibilities in a high-volume, automated compounding device that can implement custom scripts, custom preparation orders, and even manual fluid inputs.

In one example, the compatibility between a material source solution being added to the final container 80 or the common output line 2031 and the solution present in the final container 80 or the common output line 2031 can be evaluated. In some instances, material source solutions that are packaged at concentrations that are incompatible with other material source solutions must be diluted before they come into contact with each other in common fluid lines or containers. In an admixture process, the highest dilution will occur when the greatest amount of diluting fluids are already present in the container into which the solutions are being dispensed. Thus, these solutions can be transferred first to a final container as a diluent to concentrated material source ingredients that may be incompatible with each other at packaged concentrations. In the context of the compounding systems and methods disclosed herein, the mixing of incompatible fluids can occur when two fluids meet at the union junction 60. For example, in the system 1, material source solutions are drawn from either micro or macro fluid sources 4a, 4b into a plurality of micro tubing or macro tubing that are all joined together downstream of the pump rotors 41, 42 at the union junction 60 before being dispensed into the final IV bag 80. The sequence of fluid delivery can be based upon pre-programmed templates that provide a preparation order, which is a pumping sequence for fluid transfer. Incompatible fluids should not be delivered simultaneously because they may negatively react at the union junction 60 and/or downstream in the output line 2031, where the solutions may remain highly concentrated in the flow path.

Figure 39A:
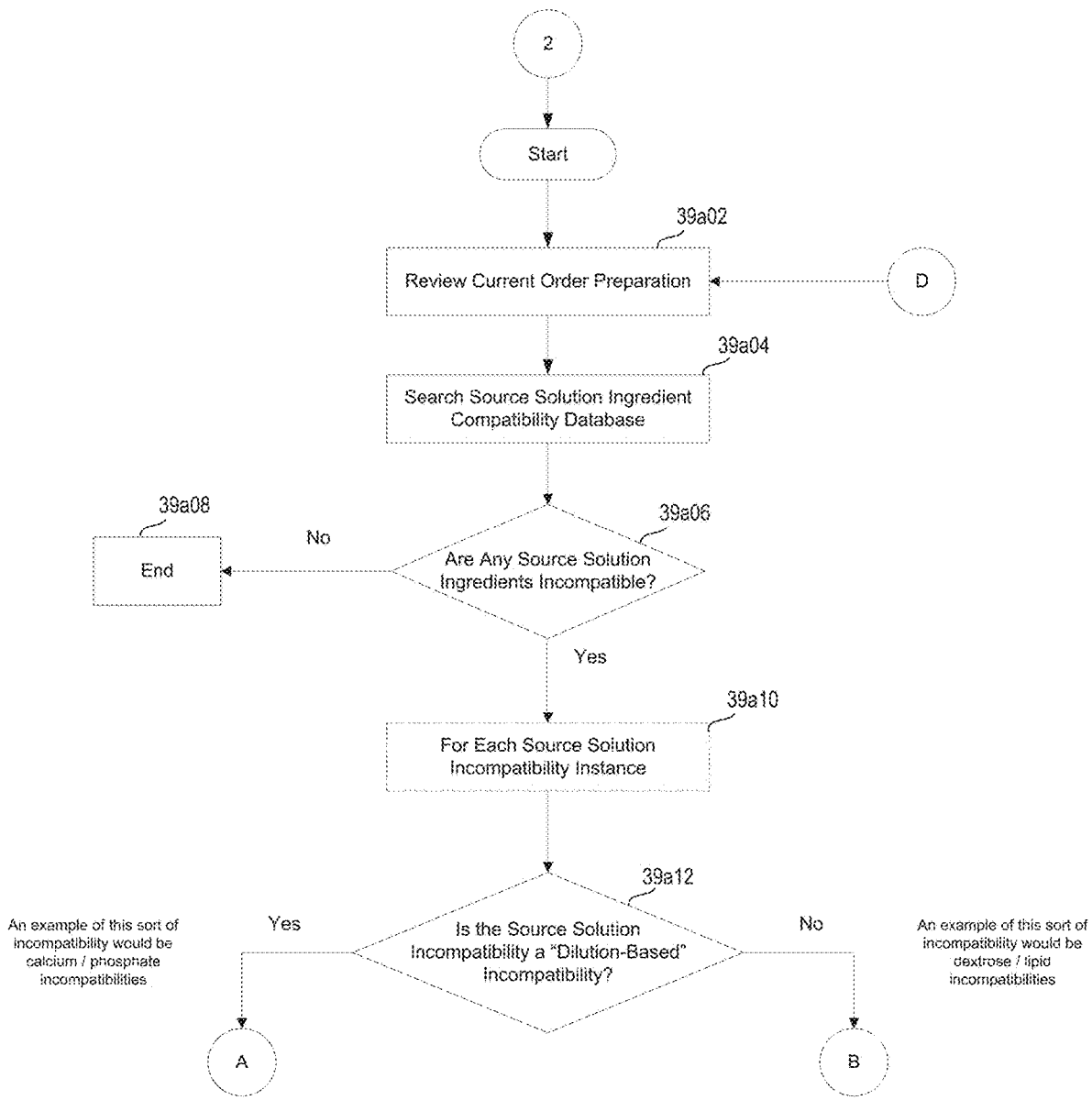
FIGS. 39a-39d together comprise a flow chart illustrating logic for controlling the compounding process to prevent simultaneous drawing of incompatible fluids in accordance with the principles of the disclosed subject matter.
Figure 39B:
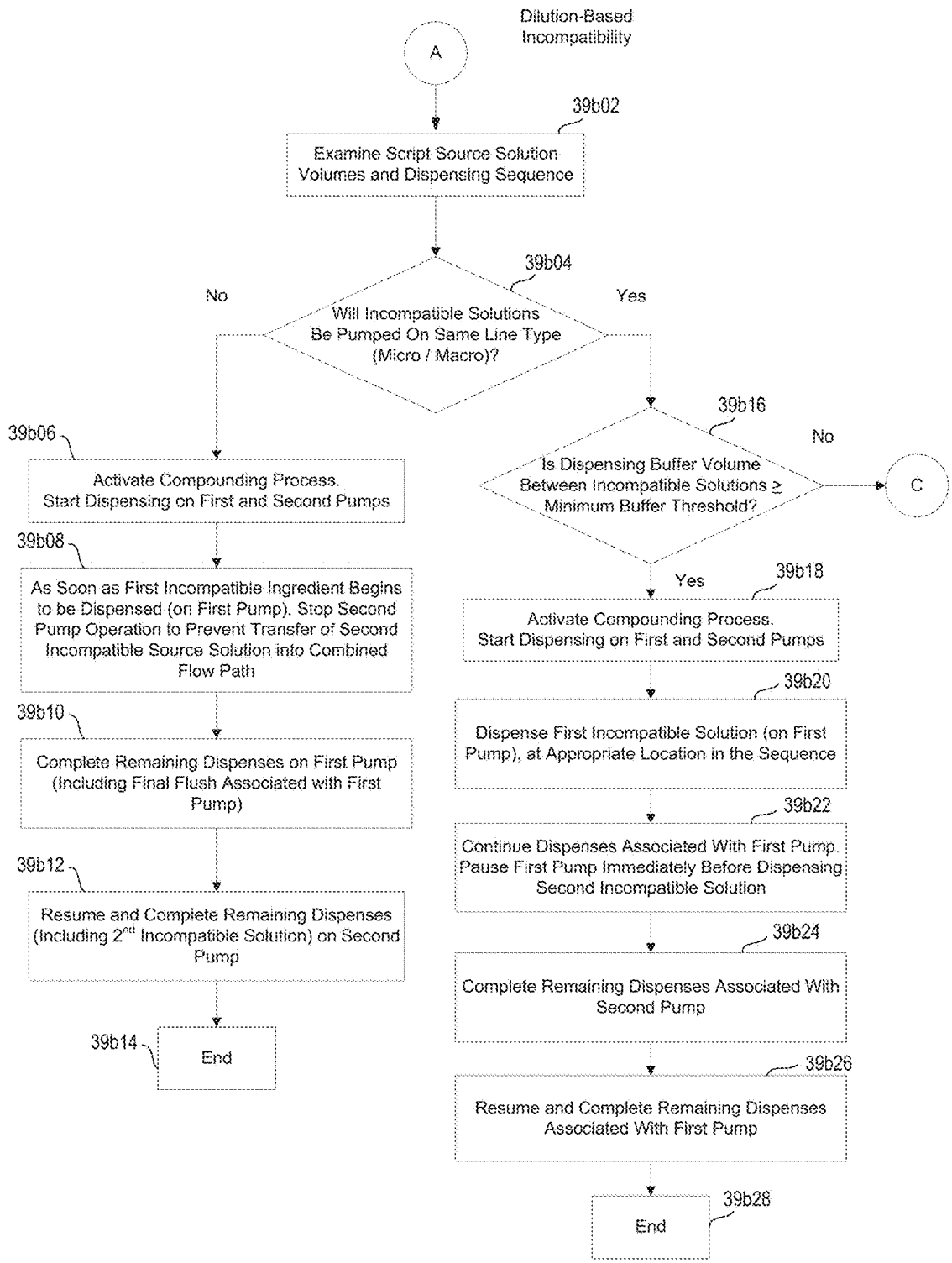

FIG. 39a illustrates the process for initiating an algorithm for preventing simultaneous drawing of incompatible liquids into a common flow path. The process begins at step 39a02 where the current order preparation is reviewed. The process then moves to step 39a04 where the controller 2900 searches the source solution ingredient compatibility database. The process then moves to step 39a06 where the system determines whether any of the source solutions are incompatible. If the system determines that the solutions are compatible, then the process ends at step 39a08. Otherwise, the process moves to step 39a10 where the controller 2900 determines each instance of a source solution incompatibility. The process then moves to step 39a12 where the controller 2900 determines whether the source solution incompatibility is a "dilution based" incompatibility. If the source solution incompatibility is a "dilution based" incompatibility, then the process moves to step 39b02 in FIG. 39b. If the source solution incompatibility is not "dilution based," then the process moves to step 39c02 shown in FIG. 39c.

In step 39b02, the script source solution volumes and dispensing sequences are examined. The process then moves to step 39b04 where the controller 2900 determines whether incompatible solutions will be pumped on the same line type (a micro or macro line). If the controller 2900 determines that incompatible solutions will be pumped along the same line, then the process moves to step 39b16. If the controller 2900 determines that incompatible solutions will not be pumped along the same line, then the process moves to step 39b06.

In step 39b06, the controller 2900 activates the compounding process and dispensing on the first and second pumps is commenced. The process then moves to step 39b08 where as soon as the first incompatible ingredient starts dispensing (via the first pump), the second pump stops operating to prevent the transfer of the second incompatible source solution into the combined flow path. The process then moves to step 39b10 where dispensing of all of the fluid along the first pump is completed, including a final fluid flush using the first pump. The process then moves to step 39b12 where the controller 2900 resumes and completes the remaining dispenses, including any and all remaining dispenses using the second pump. The process then moves to step 39b14 where the process ends.

Returning to step 39b16, the controller 2900 determines whether the dispensing buffer volume between incompatible solutions is greater than a minimum buffer threshold. If the dispensing buffer volume between incompatible solutions is not greater than a minimum buffer threshold, then the process moves to step 39d02 in FIG. 39d. Otherwise the process moves to step 39b18.

In step 39b18, the controller 2900 activates the compounding process so that the first and second pumps are both activated. The process then moves to step 39b20 where the first incompatible solution is dispensed using the first pump at an appropriate location in the dispensing sequence. The process then moves to step 39b22 where dispensing continues via the first pump and is then paused immediately before dispensing the second incompatible solution.

The process them moves to step 39b24 where the remaining dispenses associated with the second pump are completed. The process then moves to step 39b26 where the remaining dispenses associated with the first pump are resumed and then completed. The process then moves to step 39b28 where it ends.

Figure 39C:
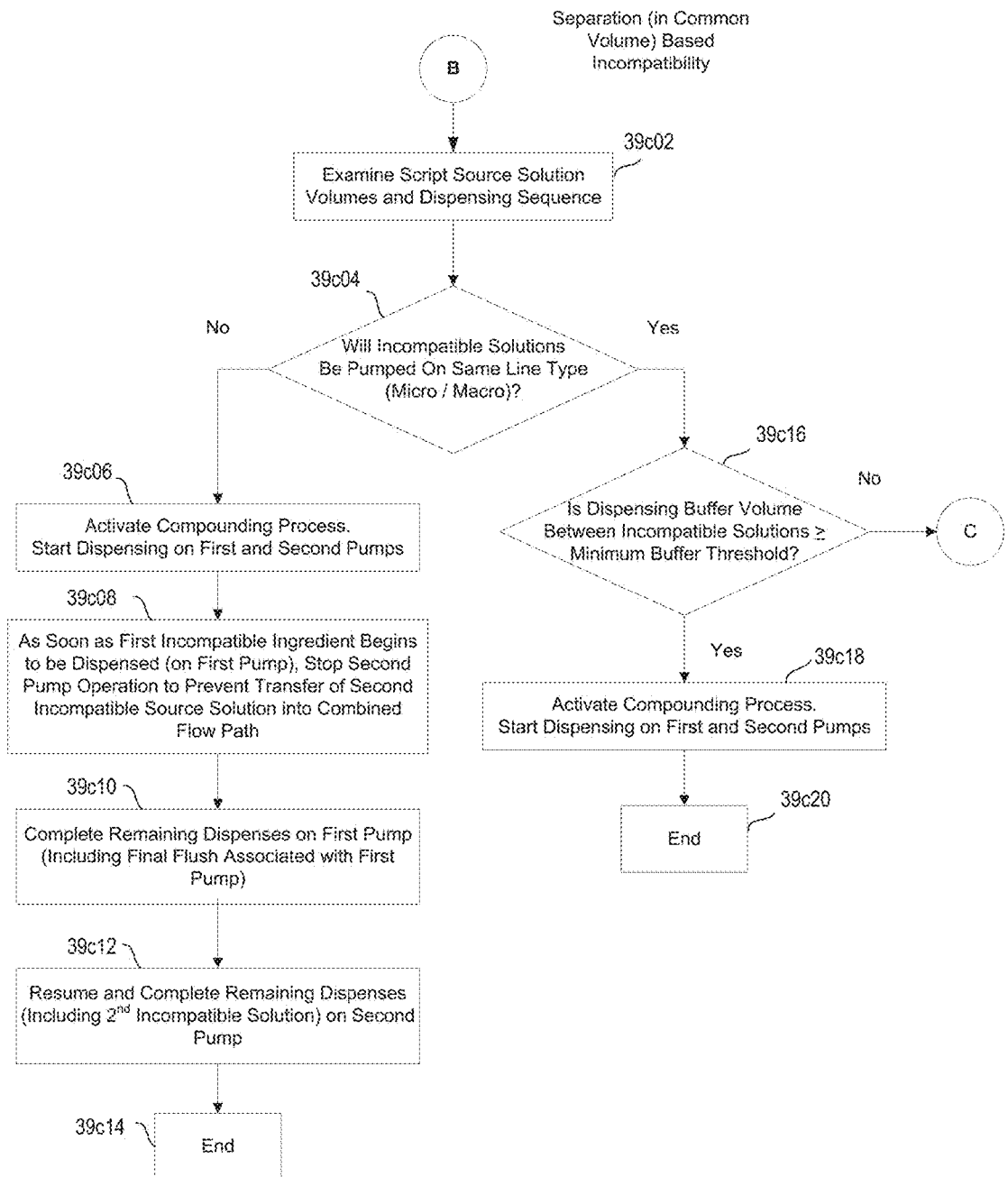

FIG. 39c illustrates the process that occurs when a determination has been made that the source solution incompatibility is not a "dilution based" incompatibility. FIG. 39c shows step 39c02 whereby the controller 2900 examines the script source solution volumes and the dispensing sequence. The process then moves to step 39c04 where the controller 2900 determines whether the incompatible solutions will be pumped on the same line. If the controller 2900 determines that the incompatible solutions will not be pumped on the same line, then the process moves to step 39c06. Otherwise, the process moves to step 39c16. In step 39c06, the controller 2900 activates the compounding process and dispensing starts using the first and second pumps. The process then moves to step 39c08 where the system stops the second pump operation as soon as the first incompatible ingredient begins to be dispensed (via the first pump). This step prevents the transfer of an second incompatible source solution into the combined flow path. The process then moves to step 39c10 where the controller 2900 completes the remaining dispenses on the first pump, including a final flush. The process then moves to step 39c12 whereby the remaining dispenses are resumed on the second pump. The process then moves to step 39c14 and ends.

In step 39c16, the controller determines whether the dispensing buffer volume between incompatible solutions is greater than the minimum buffer threshold. If the dispensing buffer volume between incompatible solutions is greater than the minimum buffer threshold, then the process moves to step 39c18 where the controller 2900 activates the compounding process and starts dispensing on the first and second pumps. The process then ends at step 39c20.

Figure 39D:
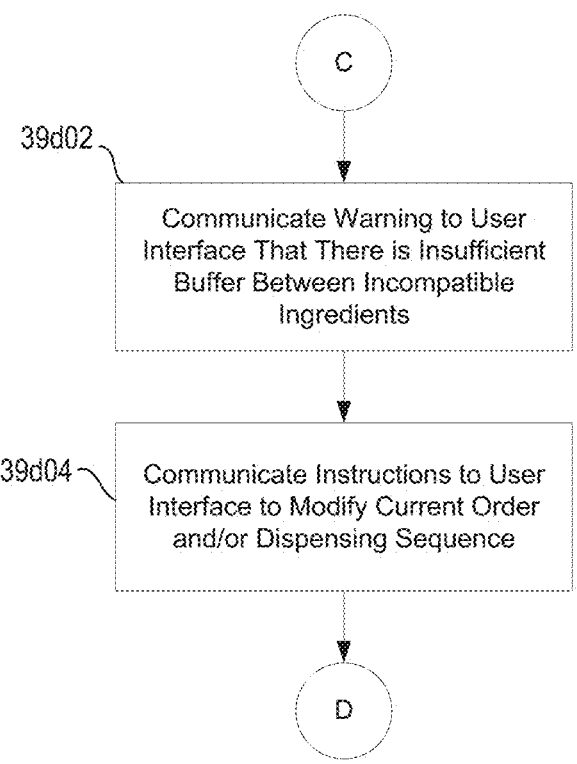

In step 39c16, if the controller 2900 determines that the dispensing buffer volume between incompatible solutions is not greater than the minimum buffer threshold, then the process moves to step 39d02 shown in FIG. 39d. In step 39d02, the controller 2900 communicates a warning to the user interface that there is an insufficient buffer between incompatible ingredients. The process then moves to step 39d04 where the controller 2900 communicates instructions to the user interface to modify the current order and/or dispensing sequence. The process then moves to step 39a02 (FIG. 39a) where the process begins again.

The process for managing the dispensing of incompatible fluids is now complete.

Fluid Line Degradation

The controller 2900 can initiate a fluid line degradation detection process that evaluates different aspects of the system 1 that would be indicative of a fluid line being worn out. The fluid line degradation detection process can be executed by the controller 2900 according to a software algorithm.

As described above, compounding systems typically use flexible tubing as fluid transfer lines through the pump. Use of a worn and/or degraded fluid line can result in the dispensing of an inaccurate amount of fluid. However, it can be difficult to determine when a fluid line should be replaced due to wear. Typically, a new tube has a circular cross-section that becomes oval within a few minutes of use. Furthermore, if the pump is a peristaltic pump, a rotor of the pump can roll or squeeze the fluid line between rollers and the platen. The compression of the flexible tubing displaces fluid ahead of the rollers in the tubing section downstream of the pump. Peristaltic pumps exert a great deal of force on the fluid line to effectuate pumping. After repeated squeezing, a fluid line can lose its round cross-sectional shape and take on an oval or oblong shape from the pinching force of the peristaltic pump. Such a misshapen fluid line can restrict fluid flow. In these cases, the pumps may not deliver the required amount of fluid due because the volume of fluid being dispensed differs as the tubing has changed its shape.

Fluid lines can also become worn over time to the point of being compromised by a crack or split in the fluid line wall. Worn fluid lines can cause inaccurate transfer of fluids from the material source solutions. Without knowing the exact change in volume of a fluid being dispensed through a worn fluid line, it may be difficult to determine the exact volume or concentration delivered to a final container.

Thus, the controller 2900 can be configured to execute an algorithm to track the usage and/or the fluid transfer rate of the transfer lines during the compounding processes. The monitoring and analysis of such data can be used to determine when a fluid line is showing signs of degradation, and thus requires replacement. One of the exemplary methods can include, but is not limited to, logical steps and system commands for calibrating the pump at an initial state, transferring a small amount of calibration solution so that the flow tube forms a substantially oval shape and then measuring changes in the flow rate delivery volume as the pump motor operates over time. In one embodiment, the pump motor can be adjusted for a calibration error factor based on changes in the delivery volume.

Figure 40A:
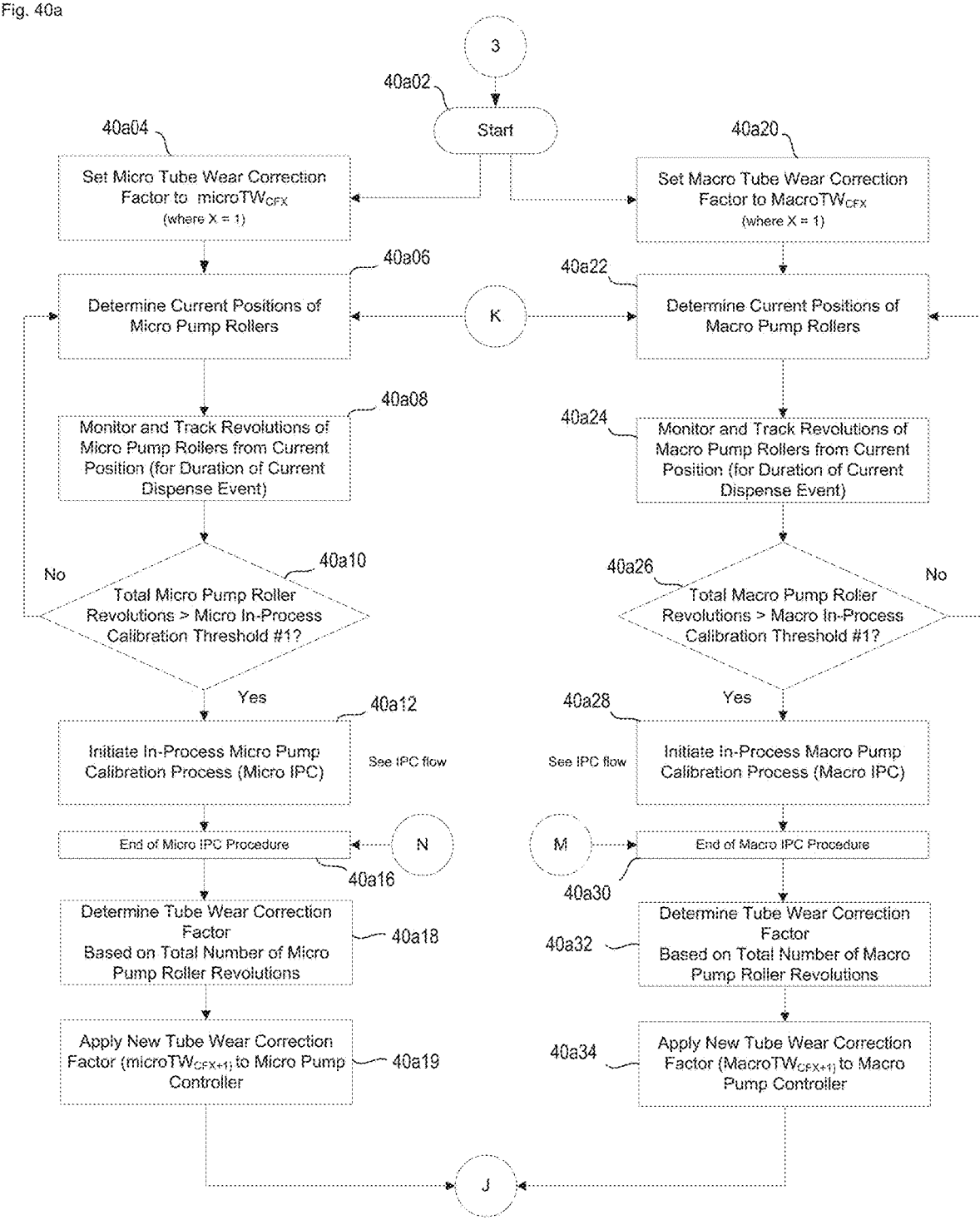
Figure 40B:
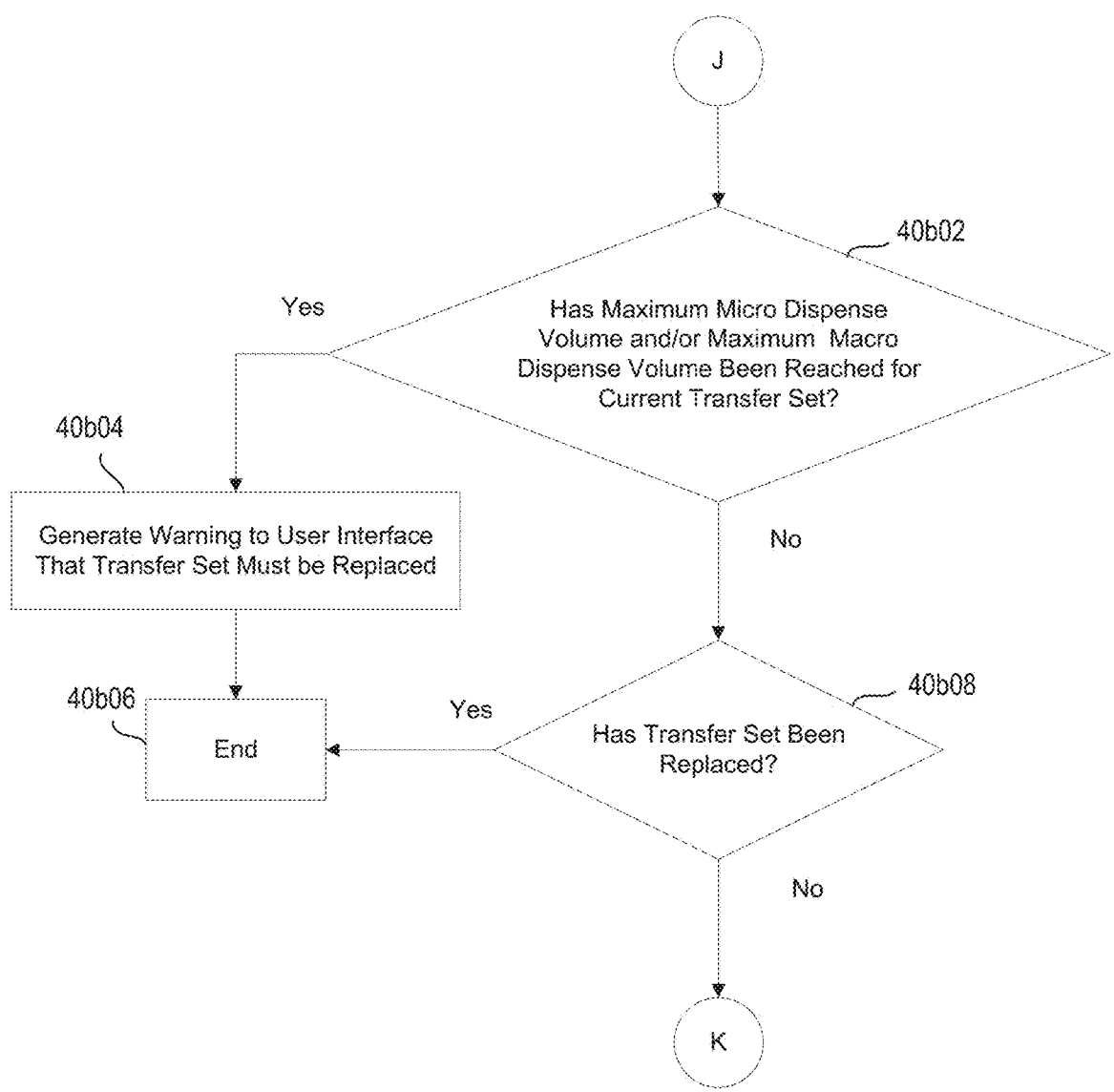

FIG. 40a illustrates the process for determining fluid line degradation that starts at step 40a02. The process then begins at step 40a04 for micro tubes and step 40a20 for macro tubes. In step 40a04, the controller 2900 sets a micro tube wear correction factor to "microTW$_{CFX}$." This correction factor is based upon a volume of fluid that passes through the micro tube over time. The process then moves to step 40a06 where the controller 2900 determines the current positions of the micro pump rollers. The process then moves to step 40a08 where the controller 2900 monitors and tracks revolutions of the micro pump rollers from their current positions for the duration of the dispensing event. The process then moves to step 40a10. In step 40a10, the controller 2900 determines whether the total micro pump roller revolutions are greater than the micro in-process calibration threshold. If the total micro pump roller revolutions are not greater than the micro in-process calibration threshold, then the process returns to step 40a06. Otherwise, the process continues to step 40a12. In step 40a12 the controller 2900 initiates an in-process micro pump calibration process. The methodology of the in-process micro pump calibration process is set forth in greater detail in FIG. 40c. Once the in-process micro pump calibration process is completed (step 40a16), then the process moves to step 40a18 where the controller 2900 determines a tube wear correction factor based upon a total number of micro pump roller revolutions. The process then moves to step 40a19 where the controller 2900 applies a new tube wear correction factor to the micro pump controller. The process then moves to step 40b02 shown in FIG. 40b whereby the controller 2900 determines whether a maximum micro dispense volume and/or a minimum macro dispense volume has been reached by the current transfer set. If the maximum dispense volume has been reached, then the process moves to step 40b04 and a warning is generated to the user interface indicating that the transfer set must be replaced.

In step 40b02, if the controller 2900 determines that the maximum micro dispense volume and/or a minimum macro dispense volume has not been reached by the current transfer set, then the process moves to step 40b08. In step 40b08, the controller determines if the transfer set has been replaced. If the transfer set has been replaced, then the process moves to step 40b06 and ends. Otherwise, the process returns to step 40a06 to determine the position of the pump rollers.

The process described above in connection with steps 40a04-40b06 is similarly carried out in steps 40a20-40b06 except that steps 40a04-40b06 relate to micro pumps and steps 40a20-40b06 relate to macro pumps.

FIG. 40c described in greater detail the in-process pump calibration step 40a12 for the micro pumps and step 40a28 for the macro pumps. The in-process pump calibration process of FIG. 40c is described with respect to both micro pump calibration and macro pump calibration.

In FIG. 40c, step 40c02 shows initiation of the in-process micro pump calibration process. The process then moves to step 40c04 where the controller 2900 determines whether the current compounding order contains the proper conditions to perform an in-process calibration for the micro pump. If the controller 2900 determines that the current compounding order contains the proper conditions to perform an in-process calibration for the micro pump, then the process moves to step 40c18, otherwise, the process moves to step 40c06.

In step 40c18, the controller 2900 performs a micro side in-process calibration during compounding of the current order and the order is completed. The process then moves to step 40c20 where the controller 2900 determines whether the micro side calibration was successful. If the calibration was successful, then the process moves to step 40a16 (end of calibration). If the calibration was not successful, then the process moves to step 40a06 where the current position of the roller is determined.

In step 40c06, the controller 2900 performs processes to initiate and complete the compounding of the current order. The process then moves to step 40c12 where the controller 2900 determines whether the total micro pump roller revolutions exceeds the micro in-process calibration threshold. If it is determined in step 40c16 that the total micro pump roller revolutions do not exceed the micro in-process calibration threshold, the process returns to step 40a06 (determining the position of the pump rollers). In contrast, if the total micro pump roller revolutions exceed the micro in-process calibration threshold, the process moves to step 40c22. In step 40c22, a message is generated to the user interface notifying the operator that pump calibration must be performed before the next compounding order. The process then moves to step 40c24 where the micro and macro calibration has been performed. The process then moves to step 40c26 where the controller 2900 applies new tube wear correction factors to the micro and macro pump controllers. The process then returns to step 40a06 where the controller 2900 determines the current position of the micro pump rollers.

The process for determining tube wear is now complete.

Figure 41:
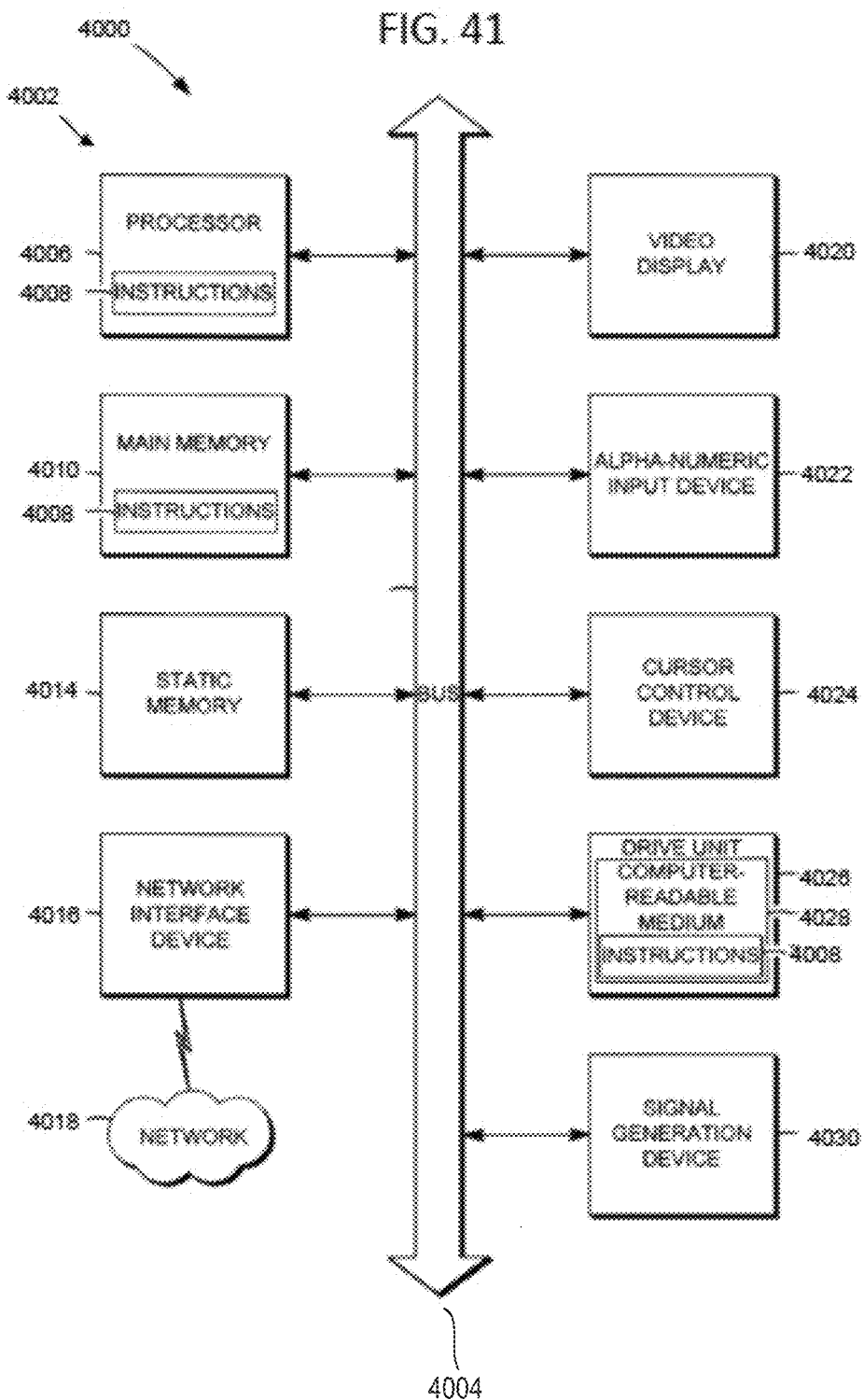
FIG. 41 is a block diagram of a processing system of the exemplary compounding device controller in the example form of a computer system within which a set of instructions for causing the controller to perform any one or more of the methodologies discussed herein may be executed.

FIG. 41 is a block diagram of an exemplary processing system 4000 of the controller 2900 in the example form of a computer system 4002 within which a set of instructions for causing the processing system 4000 to perform any one or more of the methodologies discussed for the embodiments may be executed. The controller 2900 and any other sub-controller of the compounding system 1 may include functionality of the one or more computer systems 4002. In an exemplary embodiment, the processing system 4000 operates as an integrated device, a standalone device, or may be connected (e.g., networked) to other computer systems, machines, or processing systems. In a networked deployment, the processing system 4000 may operate in the capacity of a server or a client machine in a server-client network environment, or as a peer machine in a peer-to-peer (or distributed) network environment. The processing system may be a server computer, a client computer, a personal computer (PC), a tablet PC, a set-top box (STB), a personal digital assistant PDA), a cellular telephone, a smart phone, a Web appliance, a network router, switch, or bridge, or any machine capable of executing a set of instructions (sequential or otherwise) that specify actions to be taken by that machine. Further, while only a single processing system is illustrated, the term "processing system" or "machine" or "computer system" shall also be taken to include any collection of machines that can individually or jointly execute a set (or multiple sets) of instructions to perform any one or more of the methodologies discussed herein.

The exemplary computer system 4002 can include a processor 4006 (e.g., a central processing unit (CPU) a graphics processing unit (GPU) or both), a main memory 4010 and a static memory 4014, which can communicate with each other via a bus 4004. The computer system 4002 can further include a video display unit 4020 (e.g., a liquid crystal display (LCD) or a cathode ray tube (CRT)). The computer system 4002 also can include an alphanumeric input device 4022 (e.g., a keyboard), a cursor control device 4024 (e.g., a mouse), a drive unit 4026, a signal generation device 4030 (e.g., a speaker) and a network interface device 4016 (e.g., a network interface card (NIC)).

The drive unit 4026 can include a non-transitory computer-readable medium 4028 on which can be stored one or more sets of instructions 4008 (e.g., software) embodying any one or more of the methodologies or functions described herein. The software 4008 may also reside, completely or at least partially, within the main memory 4010 and/or within the processor 4006 during executing thereof by the computer system 4002, the main memory 4010 and the processor 4006 also constituting non-transitory computer readable media.

The software 4008 may be further transmitted or received over a network 4018 that may include a peer-to-peer network with other processing systems 4000 or over one or more of the broadband network 3004 and the LAN 3002 (shown in FIG. 35) via the network interface device 4016 with the interconnected devices described above. While the non-transitory computer readable medium 4028 is shown in an exemplary embodiment to a single medium, the term "non-transitory computer readable medium" should be understood to include a single medium or multiple media (e.g., a centralized or distributed database, and/or associated caches and servers) that store the one or more sets of instructions. The term "non-transitory computer readable medium" should also be understood to include any medium that is capable of storing or encoding a set of instructions for execution by the computer system 4002 and that cause the computer system 4002 to perform any one or more of the methodologies of the embodiments. The term "non-transitory computer readable medium" should further be understood to include, but not be limited to, solid-state memories, and optical media, and magnetic media.

Certain systems, devices, apparatus, applications, methods, processes, or controls are described herein as including a number of modules or component parts. A component part may be a unit of distinct functionality that may be presented in software, hardware, or combinations thereof. When the functionality of a component part is performed in any part through software, the component part includes a non-transitory computer-readable medium. The component parts may be regarded as being communicatively coupled. The embodiments according to the disclosed subject matter may be represented in a variety of different embodiments of which there are many possible permutations.

In one embodiment, small or large containers 4a, 4b may be in fluidic communication with a plurality of valves. The valves may have valve actuators with valve stepper motors that may be operatively connected to the controller 2900 to facilitate opening and closing of the valves. The valves may be fluidly connected to a micro or macro flow paths that are fluidly connected to a micro or macro pumps 41, 42, respectively. The motors for the micro or macro pumps 41, 42 of are operatively connected to the computer system 4000 of the controller 2900, which is also operationally connected to one or more of the valve stepper motors 102a, 102b.

While the subject matter has been described in detail with reference to exemplary embodiments thereof, it will be apparent to one skilled in the art that various changes can be made, and equivalents employed, without departing from the scope of the invention. All related art references discussed in the above Description of the Related Art section are hereby incorporated by reference in their entirety.

The methods described herein do not have to be executed in the order described, or in any particular order. Moreover, various activities described with respect to the methods identified herein can be executed in serial or parallel fashion. In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, the claimed subject matter may lie in less than all features of a single disclosed embodiment.

What is claimed is:

1. A compounding apparatus for facilitating formation of an admixture by mixing at least three materials selected among multiple distinct materials, the compounding apparatus being usable with an admixture container that is configured to contain the admixture, and also being usable with multiple material containers that are each configured to contain one of the at least three materials, the compounding apparatus comprising:

a delivery device that is configured to deliver the at least three selected materials from the material containers to the admixture container to facilitate formation of the admixture, the delivery device including a first pump and a second pump as well as a first line and a second line, the first pump being configured such that actuation thereof delivers a selected first of the at least three materials from its associated material container to the admixture container via the first line, the second pump being configured such that actuation thereof delivers a selected second material and third material of the at least three materials from a second material container and a third material container, respectively, to the admixture container via the second line; and a processor including a memory that is configured to store admixture data representing amounts of the at least three selected materials required to form the admixture, and line supply data that identifies either the first line or the second line as being appropriate to supply each of the at least three selected materials, the processor also including a controller that is configured to selectively actuate the first pump and second pump to supply the amounts of the at least three selected materials to the admixture container so as to facilitate formation of the admixture, the controller also being configured to selectively actuate the first pump and second pump so as to supply each of the at least three selected materials via the identified first line or second line, wherein the memory includes flow rate factor data associated with each of the distinct materials, and the processor is configured to apply a flow rate factor to calculate angular displacement required by one of the first pump and second pump for delivering an appropriate amount of a selected one of the at least three materials to the admixture container.

2. The compounding apparatus of claim 1, wherein the controller is configured to identify either the first line or the second line as being appropriate to supply one material of the at least three selected materials based on a volume of the one material to be supplied.

3. The compounding apparatus of claim 1, wherein the controller is configured to identify either the first line or the second line as being appropriate to supply one material of the at least three selected materials based on type of material to be supplied.

4. The compounding apparatus of claim 1, wherein the controller is configured to identify either the first line or the second line as being appropriate to supply one material of the at least three selected materials based on availability of the one material to be supplied.

5. The compounding apparatus of claim 1, wherein the first line is a macro line and includes at least one macro tube, and the second line is a micro line and includes at least one micro tube having a cross-sectional diameter that is smaller than a cross-sectional diameter of the at least one macro tube.

6. The compounding apparatus of claim 5, wherein the micro line includes at least one macro tube and at least one micro tube.

7. The compounding apparatus of claim 1, wherein the controller is configured to actuate the second pump to sequentially deliver the second material and third material to the admixture container via the second line.

8. A compounding apparatus for facilitating formation of an admixture that involves mixing at least two materials selected among multiple distinct materials, one material of the multiple distinct materials being incompatible with another material of the multiple distinct materials, the compounding apparatus being usable with an admixture container that is configured to contain the admixture, and also being usable with multiple material containers that are each configured to contain one of the materials, the compounding apparatus comprising:
a delivery device that is configured to deliver the at least two selected materials from the material containers to the admixture container to facilitate formation of the admixture, the delivery device including first and second pumps, the first pump being configured such that actuation thereof delivers a selected one of the at least two materials from its associated material container to the admixture container, the second pump being configured such that actuation thereof delivers a selected other of the at least two materials from its associated material container to the admixture container; and
a processor including a memory that is configured to store admixture data representing amounts of the at least two selected materials required to form the admixture, and incompatibility data identifying the one material that is incompatible with the other material, the processor also including a controller that is configured to selectively actuate the first and second pumps to supply the amounts of the at least two selected materials to the admixture container pursuant to the stored admixture data so as to facilitate formation of the admixture, the controller also being configured to prevent delivery of the at least two selected materials if the one material and other material that are incompatible with each other are both included in the at least two selected materials, wherein the controller prevents delivery of the at least two selected materials by causing one of the first pump and the second pump to deliver a third material of the multiple distinct materials to the admixture container.

9. The compounding apparatus of claim 8, wherein the processor is configured to prevent simultaneous or immediately sequential delivery of the one material and the other material that are incompatible with each other to the admixture container.

10. The compounding apparatus of claim 8, wherein, if the one material and other material that are incompatible with each other are both included in the at least two selected materials, the processor is configured to select the third material for the one material or the other material, and to selectively actuate one of the first and second pumps to supply the third material to the admixture container.

11. The compounding apparatus of claim 8, wherein, if the one material and the other material that are incompatible with each other are both included in the at least two selected materials, the processor is configured to selectively actuate one of the first and second pumps to supply a selected one diluting material that is the third material to the admixture container so as to dilute the one material or the other material.

12. The compounding apparatus of claim 11, wherein the processor is configured to supply the selected one diluting material to the admixture container after the one incompatible material has been supplied to the admixture container, and prior to the other incompatible material is supplied to the admixture container.

13. The compounding apparatus of claim 8, wherein the first pump is configured for attachment to a first line, and the second pump is configured for attachment to a second line, the first line in fluid isolation from the second line, and
the controller is configured to reference the memory to determine whether the one material and the other material that are incompatible with each other are incompatible due to a dilution based incompatibility, and if it is determined that a dilution based incompatibility exists, the controller is configured to determine whether the one material and the other material that are incompatible with each other are to both be pumped on a same line of the first line and the second line.

14. The compounding apparatus of claim 13, wherein the controller is configured such that if the controller determines that the one material and the other material are to both be pumped on the same line, the controller further determines whether a minimum amount of buffer solution is to be pumped on the same line between the one material and the other material.

15. The compounding apparatus of claim 14, wherein if the controller determines that a minimum amount of buffer solution is to be pumped, the controller causes the first pump and second pump to begin operation and to continue operations while the one material and the buffer solution are dispensed via the first pump, the controller is further configured to pause the first pump immediately before dispensing the other material and to complete dispenses associated with the second pump while the first pump is paused, the controller further configured to resume operation of the first pump after the second pump completes dispenses.

16. The compounding apparatus of claim 13, wherein the controller is configured such that if the controller determines that the one material is to be pumped on the first line and the other material is to be pumped on the second line, the controller ceases operation of the second pump when the one material begins pumping on the first line.

17. The compounding apparatus of claim 16, wherein the controller is configured such that operation of the second pump is resumed after first pump has completed delivery of all materials.

18. The compounding apparatus of claim 8, wherein the first pump is configured for attachment to a first line, and the second pump is configured for attachment to a second line, the first line in fluid isolation from the second line, and
the controller is configured to reference the memory to determine whether the one material and the other material that are incompatible with each other are incompatible due to a dilution based incompatibility, and if it is determined that a dilution based incompatibility does not exist, the controller is configured to determine whether the one material and the other material that are incompatible with each other are to both be pumped on a same line of the first line and the second line.

19. The compounding apparatus of claim 18, wherein the controller is configured such that if the controller determines that the one material and the other material are to both be pumped on the same line, the controller further determines whether a minimum amount of buffer solution is to be pumped on the same line between the one material and the other material.

20. The compounding apparatus of claim 19, wherein if the controller determines that a minimum amount of buffer solution is to be pumped, the controller causes the first pump and second pump to begin operation and to continue operations until dispenses are complete.

21. The compounding apparatus of claim 19, wherein if the controller determines that a minimum amount of buffer solution is not scheduled to be pumped, the controller ceases operations of the first and second pumps and causes communication of a warning to a user of the compounding apparatus.

22. The compounding apparatus of claim 18, wherein the controller is configured such that if the controller determines that the one material is to be pumped on the first line and the other material is to be pumped on the second line, the controller ceases operation of the second pump when the one material begins pumping on the first line.

23. The compounding apparatus of claim 22, wherein the controller is configured such that operation of the second pump is resumed after first pump has completed delivery of all materials.

24. A method for facilitating formation of an admixture using a compounding apparatus, wherein the admixture involves mixing at least two materials selected among multiple distinct materials, one material of the multiple distinct materials being incompatible with another material of the multiple distinct materials, the compounding apparatus including a processor and being usable with an admixture container that is configured to contain the admixture, and the compounding apparatus also being usable with multiple material containers that are each configured to contain one of the materials, the method comprising:

causing a delivery device to deliver the at least two selected materials from the material containers to the admixture container to facilitate formation of the admixture, the delivery device including first and second pumps, the first pump being configured such that actuation thereof delivers a selected one of the at least two materials from its associated material container to the admixture container, the second pump being configured such that actuation thereof delivers a selected other of the at least two materials from its associated material container to the admixture container, wherein the processor includes a memory that stores admixture data representing amounts of the at least two selected materials required to form the admixture, and incompatibility data identifying the one material that is incompatible with the other material;

selectively actuating the first and second pumps to supply the amounts of the at least two selected materials to the admixture container pursuant to the stored admixture data so as to facilitate formation of the admixture;

preventing delivery of the at least two selected materials if the one material and other material that are incompatible with each other are both included in the at least two selected materials, wherein preventing delivery of the at least two selected materials includes causing one of the first pump and the second pump to deliver a third material of the multiple distinct materials to the admixture container.

* * * * *